(12) United States Patent
Wimpenny et al.

(10) Patent No.: US 9,339,605 B2
(45) Date of Patent: May 17, 2016

(54) ELECTRO-MECHANICAL DRUG DELIVERY DEVICE

(75) Inventors: Steven Wimpenny, Leamington Spa (GB); Aidan Michael O'Hare, Conventry (GB); Barry Yates, Kenilworth (GB); Shane Alistair Day, Warwick (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 798 days.

(21) Appl. No.: 13/582,012

(22) PCT Filed: Mar. 25, 2011

(86) PCT No.: PCT/EP2011/054649
§ 371 (c)(1),
(2), (4) Date: Dec. 4, 2012

(87) PCT Pub. No.: WO2011/117404
PCT Pub. Date: Sep. 29, 2011

(65) Prior Publication Data
US 2013/0079708 A1    Mar. 28, 2013

Related U.S. Application Data

(60) Provisional application No. 61/318,118, filed on Mar. 26, 2010.

(30) Foreign Application Priority Data

Jul. 8, 2010    (EP) .................................... 10168936

(51) Int. Cl.
*A61M 5/20* (2006.01)
*A61M 5/00* (2006.01)
(Continued)

(52) U.S. Cl.
CPC ................. *A61M 5/20* (2013.01); *A61M 5/002* (2013.01); *A61M 5/19* (2013.01); *A61M 5/24* (2013.01);
(Continued)

(58) Field of Classification Search
CPC ............... A61M 2209/086; A61M 2205/8237; A61M 2205/8256; A61M 2205/8262
See application file for complete search history.

(56) References Cited

U.S. PATENT DOCUMENTS 7,111,756 B2 *  9/2006  Grey et al. ....................... 222/21
8,641,672 B2 *  2/2014  Yodfat et al. ................... 604/151

(Continued)

FOREIGN PATENT DOCUMENTS

WO    2008/045203    4/2008
WO    2009/113060    9/2009

OTHER PUBLICATIONS

International Preliminary Report on Patetnability for Int. App. No. PCT/EP2011/054649, mailed Oct. 11, 2012.
(Continued)

*Primary Examiner* — Aarti B Berdichevsky
(74) *Attorney, Agent, or Firm* — McDonnell Boehnen Hulbert & Berghoff LLP

(57) ABSTRACT

An electro-mechanical drug delivery device comprises a main body having a distal end and a proximal end. The distal end is configured to attach to a dispense interface. A separable housing that can prevent an administration of a drug by the drug delivery device, the housing configured to cover at least a portion of the distal end of the main body when the separable housing is coupled to the main body of the drug delivery device. A conduction element is provided by the main body and configured for establishing an electrical connection with an electrical connector. Establishment of the electrical connection is prevented when the housing does not cover at least a portion of the distal end of the main body. The electrical connection may be established when the housing covers at least a portion of the distal end of the main body of the drug delivery device.

15 Claims, 33 Drawing Sheets

(51) Int. Cl.
*A61M 5/19* (2006.01)
*A61M 5/24* (2006.01)
A61M 5/31 (2006.01)
A61M 5/315 (2006.01)
A61M 5/34 (2006.01)
A61M 39/10 (2006.01)
H02J 7/00 (2006.01)

(52) U.S. Cl.
CPC ........... *A61M 5/2448* (2013.01); *A61M 5/3146* (2013.01); *A61M 5/31546* (2013.01); *A61M 5/345* (2013.01); *A61M 2005/2496* (2013.01); *A61M 2005/3104* (2013.01); *A61M 2005/3125* (2013.01); *A61M 2005/3126* (2013.01); *A61M 2005/3128* (2013.01); *A61M 2005/31588* (2013.01); *A61M 2039/1083* (2013.01); *A61M 2039/1088* (2013.01); *A61M 2205/3584* (2013.01); *A61M 2205/50* (2013.01); *A61M 2205/505* (2013.01); *A61M 2205/52* (2013.01); *A61M 2205/6072* (2013.01); *A61M 2205/8206* (2013.01); *A61M 2205/8212* (2013.01); *A61M 2205/8256* (2013.01); *A61M 2209/086* (2013.01); *H02J 7/0047* (2013.01)

(56) References Cited

U.S. PATENT DOCUMENTS

| | | | |
|---|---|---|---|
| 8,657,787 B2* | 2/2014 | Neer | 604/156 |
| 2002/0193679 A1* | 12/2002 | Malave et al. | 600/407 |
| 2004/0069798 A1* | 4/2004 | Grey et al. | 222/52 |
| 2010/0263665 A1* | 10/2010 | Brown et al. | 128/203.12 |
| 2011/0009824 A1* | 1/2011 | Yodfat et al. | 604/151 |

OTHER PUBLICATIONS

International Search Report for Int. App. No. PCT/EP2011/054649, completed Sep. 9, 2011.

* cited by examiner

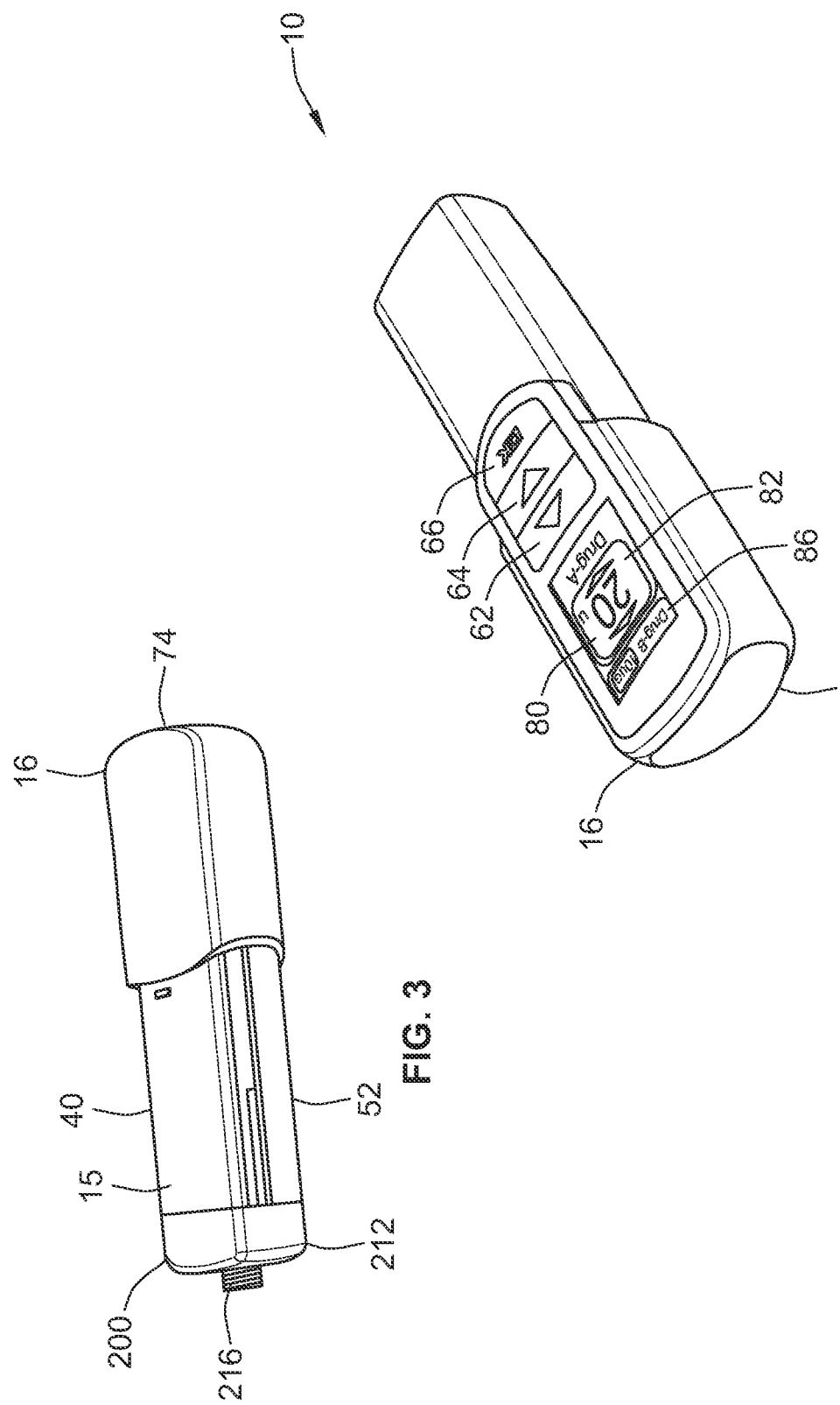

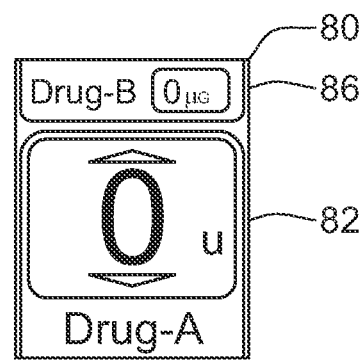
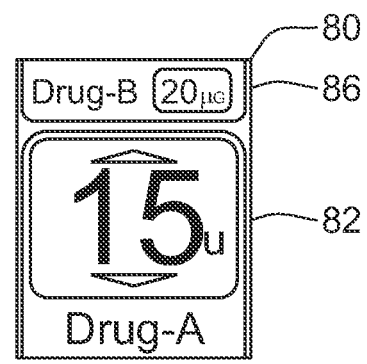
FIG. 5A  FIG. 5B
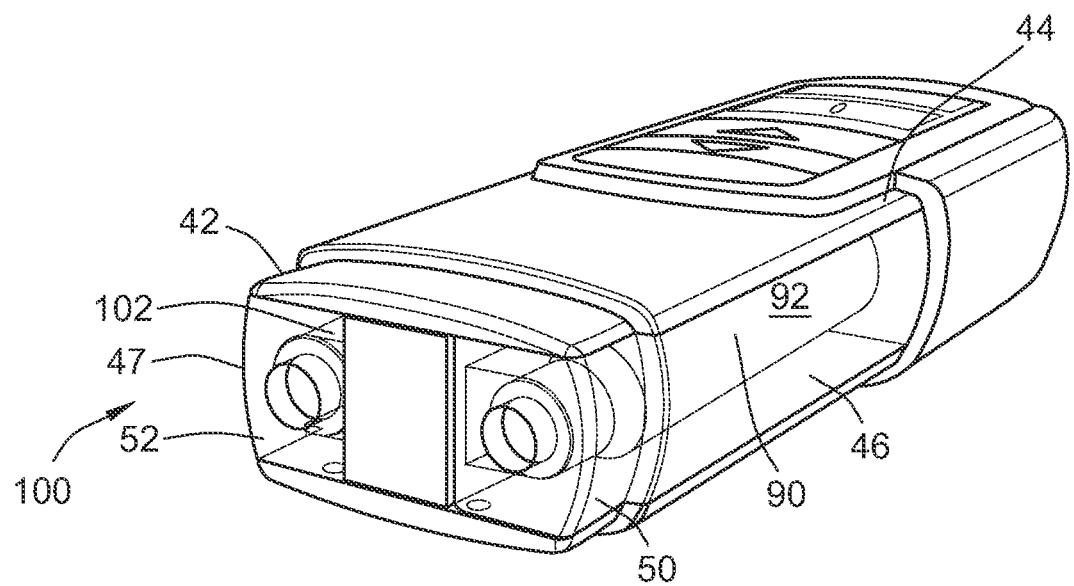
FIG. 6

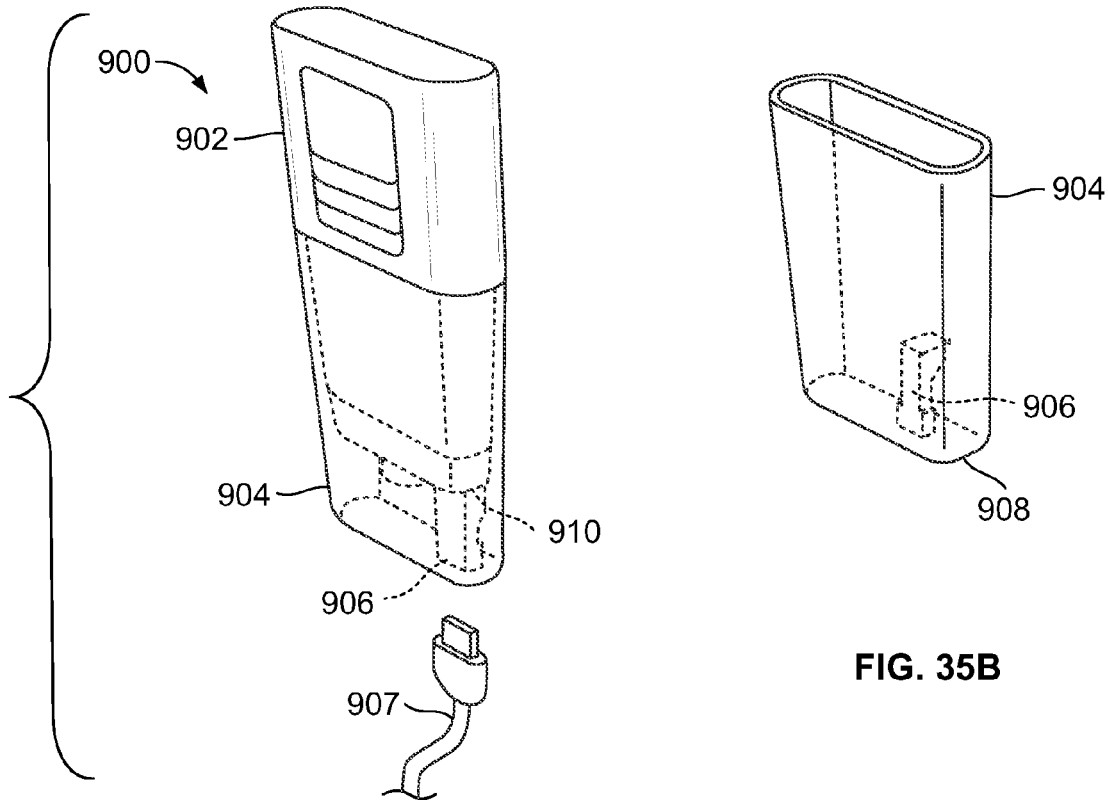
FIG. 35A
FIG. 35B
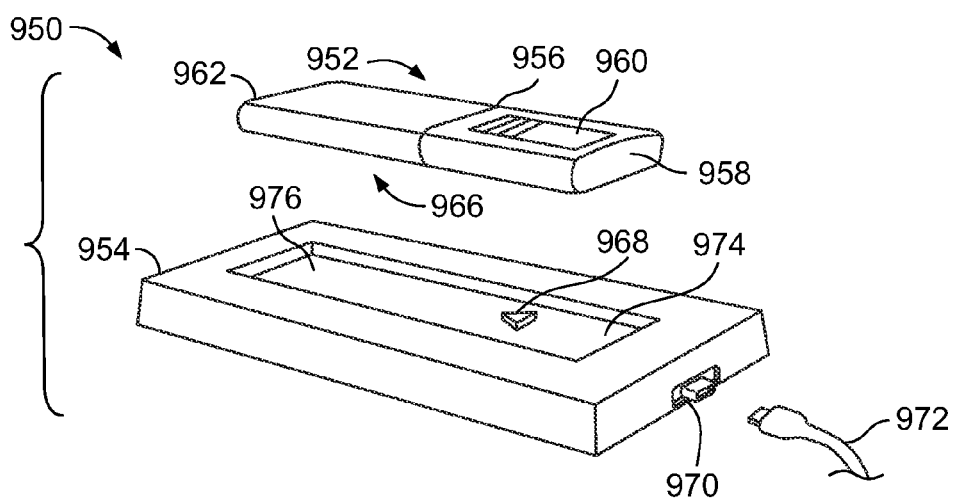
FIG. 36A

ELECTRO-MECHANICAL DRUG DELIVERY DEVICE

CROSS REFERENCE TO RELATED APPLICATIONS

The present application is a U.S. National Phase Application pursuant to 35 U.S.C. §371 of International Application No. PCT/EP2011/054649 filed Mar. 25, 2011, which claims priority to U.S. Provisional Patent Application No. 61/318,118 filed Mar. 26, 2010 and European Patent Application No. 10168936.2 filed Jul. 8, 2010. The entire disclosure contents of these applications are herewith incorporated by reference into the present application.

FIELD OF THE INVENTION

According to one aspect, the present disclosure relates to a drug delivery device configured for establishing an electrical connection to an electrical connector. As an example, the drug delivery device may be an electro-mechanical device. The electrical connector may be an external connector.

According to further aspects, the present disclosure relates to medical devices and methods of delivering at least two drug agents from separate reservoirs using a device having a programmable dose setting mechanism and a single dispense interface. Such drug agents may comprise a first and a second medicament. A single dose setting procedure initiated by the user causes the drug delivery device to compute a dose of a second drug agent based on a selected therapeutic dose algorithm. This single dose setting procedure initiated by the user may also cause the drug delivery device to compute a dose of a third drug agent based on a (potentially) different selected therapeutic dose algorithm. Such algorithms may either be previously selected prior to dose setting or at the time that the dose is set.

The drug agents may be contained in two or more multiple dose reservoirs, containers or packages, each containing independent (single drug compound) or pre-mixed (co-formulated multiple drug compounds) drug agents. The electro-mechanical dose setting mechanism is of particular benefit where a targeted therapeutic response can be optimized for a specific target patient group. This may be achieved by a microprocessor based drug delivery device that is programmed to control, define, and/or optimize a therapeutic dose profile. A plurality of potential dose profiles may be stored in a memory device operatively coupled to the microprocessor. For example, such stored therapeutic dose profiles may include, but are not limited to, a linear dose profile; a non-linear dose profile; a fixed ratio—fixed dose profile; a fixed dose—variable dose profile; a delayed fixed dose—variable dose profile; or a multi-level, fixed dose variable dose profile as discussed and described in greater detail below. Alternatively, only one dose profile would be stored in a memory device operatively coupled to the microprocessor.

BACKGROUND

Certain disease states may require treatment using one or more different medicaments. Some drug compounds need to be delivered in a specific relationship with each other in order to deliver the optimum therapeutic dose. Specific aspects of the present disclosure may be of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin (also may be referred to as the first or primary medicament) along with a glucagon-like peptide-1 such as GLP-1 or GLP-1 analog (also may be referred to as the second drug or secondary medicament). GLP-1 is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it is advantageous to store the active components separately and only combine them at the point of delivery, e.g., injection, needle-less injection, pumps, or inhalation. However, the process for combining the two agents and then administering this combination therapy needs to be simple and convenient for the user to perform reliably, repeatedly and safely.

A further problem that may often arise is that the quantities and/or proportions of each active agent making up the combination therapy may need to be varied for each user or at different stages of their therapy. For example, one or more active agents may require a titration period to gradually introduce a patient to a "maintenance" dose. A further example would be if one active agent requires a non-adjustable fixed dose while the other active agent is varied. This other active agent may need to be varied in response to a patient's symptoms or physical condition. Because of such a potential problem, certain pre-mixed formulations comprising two or more active agents may not be suitable as these pre-mixed formulations would have a fixed ratio of the active components, which could not be varied by the healthcare professional or user.

Additional problems can arise where a multi-drug compound therapy is required, because many users cannot cope with having to use more than one drug delivery system or make the necessary accurate calculation of the required dose combination. Other problems arise where a drug delivery system requires the user to physically manipulate the drug delivery device or a component of the drug delivery device (e.g., a dose dialing button) so as to set and/or inject a dose. This may be especially true for certain users who are challenged with dexterity or computational difficulties.

Accordingly, there exists a need to provide devices and/or methods for the delivery of two or more medicaments in a single injection or delivery step that is simple for the user to perform without complicated physical manipulations of the drug delivery device. According to certain embodiments of the disclosed programmable electro-mechanical drug delivery device, the above-mentioned problems may be overcome. For example, the proposed drug delivery device provides separate storage containers or cartridge retainers for two or more active drug agents. These active drug agents are then only combined and/or delivered to the patient during a single delivery procedure. These active agents may be administered together in a combined dose or alternatively, these active agents may be combined in a sequential manner, one after the other. This may be just one programmable feature of the disclosed electro-mechanical drug delivery device.

In addition, when a user sets a dose of the first or primary medicament, the disclosed electro-mechanical micro-processor based drug delivery device may automatically calculate the dose of the second medicament (i.e., non-user settable) based at least in part on a programmed therapeutic dose profile or programmed algorithm. In an alternative arrangement, the disclosed electro-mechanical micro-processor based drug delivery device automatically calculates the dose of the second medicament and/or a third medicament based on a programmed therapeutic dose profile or programmed algorithm. The profile used to compute the dose of the third medicament may or may not be the same type of profile used to compute the dose of the secondary medicament.

The disclosed drug delivery device may also allow for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent. The user, for example a patient, a healthcare professional or any other person using the device, would then select the most appropriate secondary package or series or combination of series of different packages for a particular treatment regime.

One problem to be solved by the present invention is to provide a drug delivery device, wherein the safety for a user is increased.

SUMMARY

In one aspect, a drug delivery device having a main body and a separable housing is disclosed. The separable housing may be configured to couple and decouple from the main body. The main body may have a distal end and a proximal end, wherein the distal end may be configured to attach to a dispense interface. As an example, the device may be an injection device, wherein the dispense interface may comprise a needle assembly. The main body of the drug delivery device may comprise a conduction element, wherein the device may be configured for establishing an electrical connection between the conduction element and an electrical connector.

The conduction element may serve to electrically connect the main body of the drug delivery device to an external device in order to facilitate various operational needs. As examples, the external device may be part of the separable housing or may be provided as a separate device, additionally to the separable housing. The external device could be any external device arranged to connect to the main body of the drug delivery device, such as a charger or a computer. In one embodiment, the electrical connector for establishing an electrical connection to the conduction element may be part of the external device. As examples, the electrical connector may be provided by the separable housing or a separate device provided additionally to the separable housing. In this case, the separable housing may further comprise a conduction element configured for establishing an electrical connection to a corresponding electrical connector of the external device. In particular, here, the main body of the drug delivery device may be configured to be electrically connected via the separable housing to the external device.

As examples, the conduction element of the main body or the conduction element of the separable housing may comprise a Universal Serial Bus (USB) port, a Firewire port, a RS232 port, or a proprietary port. Accordingly, the corresponding connector may comprise a USB plug, a Firewire plug, a RS232 plug or a proprietary plug. Instead, in each of the examples above, the conduction element may comprise the plug and the connector may comprise the port. In this case, the plug may be understood as a conduction element and the port may be understood as the electrical connector.

The drug delivery device may need to be connected to an external device for various reasons. These various reasons may include, for example, to facilitate data transfer, e.g., from the external device to the drug delivery device or vice versa, to charge a battery of the drug delivery device, e.g., if the drug delivery device includes a rechargeable battery, or to provide software updates to an on-board electronic control unit. As an example, the drug delivery device may be an electro-mechanical device. The drug delivery device may comprise an electronic control unit which may have controlling or monitoring functions. For example, the electronic control unit may control dose setting or dose delivery operations or store data related to these operations. The connector member may be communicatively linked to the electronic control unit when the separable housing is coupled to the main body. Thereby, a transfer of power or of data may be enabled.

The drug delivery device may be configured such that when the separable housing is coupled to the main body the administration of a drug by the drug delivery device is prevented. Moreover, the device may be configured such that when the separable housing is decoupled from the main body the establishment of the electrical connection between the conduction element and the electrical connector is prevented. If the connection to an external device is done via a wired connection, there may be a potential risk of electrocution to a user if the user were to attempt to use the device while the device was still connected to the external device. For instance, an internal fault or fluid leakage within the drug delivery device could bypass the electrical insulation measures of the device and allow direct connection between the power source and the user. Therefore, the device may be configured such that an administration of the drug is prevented while the device is connected to the external device.

The separable housing may be configured to cover at least a portion of the distal end of the main body when the separable housing is coupled to the drug delivery device. In particular, the separable housing may cover a part of the main body where a dispense interface is attached. Thereby, the attachment of the main body to a dispense interface may be prevented. Alternatively or additionally, a coupling of the separable housing to the main body may be prevented when the dispense interface is attached to the main body. As an example, the separable housing may be configured as a cap, which may be attachable to the distal end of the main body. In another embodiment, the separable housing may be configured as a docking station, wherein the main body can be seated.

Moreover, an establishment of the electrical connection between the conduction element of the main body and a corresponding electrical connector may be prevented when the separable housing does not cover at least a portion of the main body, for example a portion of the distal end of the main body. As an example, the main body may comprise a member covering the conduction element when the separable housing is not coupled to the main body. The member may not cover the conduction element when the separable housing is coupled to the main body. As an example, the covering member may comprise a sliding door or a pivoting member. The covering member may mechanically interact with the separable housing when the separable housing is coupled to the main body such that conduction element gets uncovered and, thus, gets accessible for a corresponding electrical connector. Accordingly, the establishment of the electrical connection may be allowed when the separable housing is coupled to the main body.

According to a specific embodiment, an electro-mechanical drug delivery device comprises a main body having a distal end and a proximal end, wherein the distal end is configured to attach to a dispense interface; a separable housing that can prevent an administration of a drug by the drug delivery device, wherein the separable housing is configured to cover at least a portion of the distal end of the main body when the separable housing is coupled to the main body of the drug delivery device; and a conduction element provided by the main body, wherein the conduction element is configured for establishing an electrical connection with an electrical connector; wherein establishment of the electrical connection is prevented when the separable housing does not cover at least a portion of the distal end of the main body.

According to a further specific embodiment, an electro-mechanical drug delivery device is disclosed, the device having a main body, a separable housing, and a conduction element disposed in the separable housing. The main body has a distal end and a proximal end, where the distal end is configured to attach to a dispense interface. The separable housing that can prevent an administration of a drug contained within the drug delivery device, and the separable housing is configured to cover at least a portion of the distal end of the main body when the separable housing is coupled to the drug delivery device. Further, the conduction element disposed in the separable housing is configured for establishing a first electrical connection with a corresponding electrical connector and a second electrical connection with a conduction element of the main body.

According to a further embodiment, a drug delivery system is disclosed, comprising any of the drug delivery devices as described above and a docking station. The docking station may be configured such that the device can be seated in the docking station.

According to a specific embodiment, a drug delivery system including a drug delivery device and a docking station is described. The drug delivery device includes a main body having a distal end and a proximal end, where the distal end is configured to attach to a dispense interface. The drug delivery device also includes a first conduction element. The docking station comprises a first electrical connector and a second conduction element. The first conduction element is configured for connecting to the first electrical connector. Further, the second conduction element is configured for connecting to a second electrical connector, wherein the second electrical connector is an external electrical connector. Still further, when the drug delivery device is attached to the dispense interface, the drug delivery device is prevented from connecting to the docking station. When seated into the docking station, the drug delivery device may reside in either a horizontal position or in an upright position.

According to further aspects, the present disclosure allows for a combination of multiple drug compounds within a single electro-mechanical device to achieve a therapeutic dose profile. Such therapeutic dose profile may be a pre-selected profile and may be one of a plurality of dose profiles stored in a memory device contained within the drug delivery device. The electro-mechanical device may comprise two or more such medicaments. The device allows the user to set a multi-drug compound device through one single dose setting mechanism (such as a digital display, a soft-touch operable panel, and/or graphical user interface (GUI)). The device then allows the dispense of at least a plurality of medicaments through a single dispense interface (such as a double-ended needle assembly). This single dose setter can control the electro-mechanical drive unit of the device such that a predefined combination of the individual drug compounds may be administered when a single dose of one of the medicaments is set and dispensed through the single dispense interface. Although principally described in this disclosure as an injection device, the basic principle could be applicable to other forms of drug delivery, such as, but not limited to, inhalation, nasal, ophthalmic, oral, topical, and like forms of drug delivery.

By defining the therapeutic relationship between at least a plurality of drug compounds, the proposed microprocessor based drug delivery device helps to ensure that a patient/user receives the optimum therapeutic combination dose from a multi-drug compound device. This microprocessor may comprise a microcontroller. This combination dose may be set and administered without the potential inherent risks that may be associated with multiple inputs, where the user is often called upon to calculate and set the correct dose combination each time that the device is used to administer a dose. The medicaments can be fluids, defined herein as liquids, gases or powders that are capable of flowing and that change shape when acted upon by a force tending to change its shape. Alternatively, one of the medicaments may be a solid where such a solid may be carried, solubilized or otherwise dispensed with another fluid, for example a fluid medicament or a liquid.

The proposed electro-mechanical device is of particular benefit to users with dexterity or computational difficulties as the single input and associated predefined therapeutic profile removes the need for a user to calculate a prescribed dose every time they use the device. In addition, the single input allows easier dose setting and dose administration of the combined compounds. The electro-mechanical nature of the preferred drug delivery device also benefits users with dexterity and visual challenges since the proposed drug delivery device may be operated and/or controlled by way of a microprocessor based operator panel.

In a preferred embodiment a master drug compound, such as insulin, contained within a multiple dose device could be used with at least a secondary medicament contained within the same device. A third medicament contained within the same device may also be provided. For example, this third medicament could be a long or a short acting insulin.

In a preferred arrangement, a computerized electro-mechanical drug delivery device delivers at least one dose of two or more medicaments. This dose may be a combined dose. The device comprises a main body comprising a microprocessor based control unit. An electro-mechanical drive unit is operably coupled to the control unit. The electro-mechanical drive unit is coupled to a primary reservoir and a secondary reservoir. Preferably, the electro-mechanical drive unit is coupled to the primary reservoir and the secondary reservoir by way of a first and second drive trains. The first and the second drive trains may be similar in operation.

An operator interface is in communication with the control unit. A single dispense assembly (such as a dispense interface and/or a needle assembly) may be configured for fluid communication with the primary and the secondary reservoir. Activation of the operator panel sets a dose of the primary medicament from the primary reservoir. Based on at least the selected dose of the primary medicament, the control unit computes a dose of the secondary medicament based at least in part on a therapeutic dose profile. In an alternative arrangement, based on at least the selected dose of the primary medicament, the control unit computes a range of a dose of the secondary medicament based at least in part on a therapeutic dose profile. A user may then select a dose of the secondary medicament within the determined range. Based on at least the selected dose of the primary medicament, the control unit may also compute a dose or a range of a dose of the third medicament based at least in part on a therapeutic dose profile. The primary medicament may or may not be administered to an injection site simultaneously with the secondary medicament.

In one arrangement, the selected profile may be determined when a cartridge of medicament is inserted into a cartridge retainer of the drug delivery device. A cartridge may comprise one or more reservoirs for storing and releasing one or more medicaments. Separate cartridges for each medicament may be used in a device, or a single cartridge with multiple reservoirs may be used. For example, the cartridge retainer of the device may contain a cartridge identification circuit that when or if the device 'reads' a cartridge identifier provided on the inserted cartridge, logic contained in the device could determine which of the plurality of stored profiles is the appropriate profile to select for the particular medicament contained within the cartridge. In one such arrangement, this selection process might therefore be fully automatic. That is, no user intervention is required to select the proper profile. In an alternative embodiment, cartridge identification information may be used to request a profile through a wired or wireless connection, for example a universal serial bus (USB) connection, a Bluetooth™ connection, a cellular connection and/or the like. The profile may be requested from an internet page. The profile may be received by the device through the same wired or wireless connection. The profile may then be stored and applied in the apparatus without any user intervention or after confirmation by a user.

Alternatively, this therapeutic profile selection process might be semi-automatic. For example, this therapeutic profile may be suggested and selected via a graphical user interface provided on a digital display. For example, the GUI may prompt the user to confirm which profile they want from a limited range of options or fully configurable by the user, for example by a patient or health care provider.

Although the present disclosure specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used.

For the purposes of the present disclosure, the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

The term "drug" or "medicament", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp- Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group-Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In one preferred arrangement, the proposed electro-mechanical drug delivery device has a single dispense interface. This interface may be configured for fluid communication with the primary reservoir and with a secondary reservoir of medicament containing at least one drug agent. The drug dispense interface can be a type of outlet that allows the two or more medicaments to exit the system and be delivered to the patient.

In one preferred arrangement, the secondary reservoir contains multiple doses of medicament. The system may be designed such that a single activation of a dose button causes the user set dose of medicament to be expelled from the primary reservoir. As a result, a dose of medicament from the second reservoir is determined based on a preprogrammed therapeutic profile and this combination of medicaments will be expelled through the single dispense interface. By user settable dose it is meant that the user (e.g., patient or health care provider) can enter the dose of the primary medicament by way of the device so as to set a desired dose. Additionally, the user settable dose can be set remotely through a communications port such as a wireless communication port (e.g., Bluetooth, WiFi, satellite, etc.). Alternatively, the user settable dose can be set through a wired communications port such as a Universal Serial Bus (USB) communications port. Additionally, the dose may be set by another device, such as a blood glucose monitor after performing a therapeutic treatment algorithm.

By calculated dose, it is meant that the user (or any other input) cannot independently set or select a dose of medicament from the secondary reservoir but rather it is computed to achieve a predefined therapeutic profile of a combination of both primary and secondary medicaments. In other words, when the user (or another input as described above) sets the dose of the primary medicament in the primary reservoir, the dose of the second medicament is determined by the microprocessor control unit. This combination of medicaments is then administered via a single interface.

The combination of compounds as discrete units or as a mixed unit can be delivered to the body via a double-ended needle assembly. This would provide a combination drug injection system that, from a user's perspective, would be achieved in a manner that closely matches the currently available injection devices that use standard needle assemblies. One possible delivery procedure may involve the following steps:

1. Attach a dispense interface to a distal end of the electromechanical injection device. The dispense interface comprises a first and a second proximal needle. The first and second needles pierce a first reservoir containing a primary compound and a second reservoir containing a secondary compound, respectively.
2. Attach a dose dispenser, such as a double-ended needle assembly, to a distal end of the dispense interface. In this manner, a proximal end of the needle assembly is in fluidic communication with both the primary compound and secondary compound.
3. Dial up/set a desired dose of the primary compound from the injection device, for example, via a graphical user interface (GUI).
4. After the user sets the dose of the primary compound, the micro-processor controlled control unit determines or computes a dose of the secondary compound and preferably determines or computes this second dose based on a previously stored therapeutic dose profile. Where the drug delivery device includes a third medicament, the micro-processor controlled control unit computes a dose of the third medicament based on the same or a different therapeutic dose profile. It is this computed combination of medicaments that will then be injected by the user. The therapeutic dose profile may be user selectable.
5. Optionally, after the second dose has been computed, the device may be placed in an armed condition. In such an optional armed condition, this may be achieved by pressing and/or holding an "OK" button on a control panel. This condition may provide for greater than a predefined period of time before the device can be used to dispense the combined dose.
6. Then, the user will insert or apply the distal end of the dose dispenser (e.g., a double ended needle assembly) into the desired injection site. The dose of the combination of the primary compound and the secondary compound (and potentially a third medicament) is administered by activating an injection user interface (e.g., an injection button).

The proposed drug delivery system may be designed in such a way as to limit its use to exclusive primary and secondary reservoirs through employment of dedicated or coded cartridge features. In some situations, it may be beneficial from a therapeutic and safety point of view to ensure that the primary reservoir can be a standard drug containing vial or cartridge. This would allow the user to deliver a combined therapy when a secondary reservoir is included in the device. It would also allow delivery of the primary compound independently through a standard dose dispenser in situations where the combined therapy is not required. This could include situations, such as, but not limited to, dose splitting (i.e., delivering the complete dose of the primary therapy in two separate injections) or top-up of the primary compound in a way that would prevent the potential risk of double dosing of the secondary compound that such scenarios might otherwise present.

A particular benefit of the proposed drug delivery device is that the use of two or more multi-dose reservoirs makes it possible to tailor dose regimes when required, for example where a titration period is necessary for a particular drug. The secondary reservoir, third reservoir, and/or other reservoirs may be supplied in a number of titration levels with certain differentiation features such as, but not limited to, aesthetic design of features or graphics, numbering or the like symbols, so that a user could be instructed to use the supplied secondary reservoirs in a specific order to facilitate titration. Alternatively, a prescribing physician or health care provider may provide the patient with a number of "level one" titration secondary reservoirs and then when these were finished, the physician could then prescribe the next level. Alternatively, a single strength formulation could be provided and the device could be designed to deliver a pre-defined fraction of the full intended dose during the titration period. Such a fraction could be gradually increasing, stepped or any therapeutically beneficial or desirable variant thereof. One advantage of such a titration program is that the primary device remains constant throughout the administration process.

In a preferred arrangement, the drug delivery device is used more than once and therefore is multi-use. Such a device may or may not have a replaceable reservoir of the primary drug compound, but the presently disclosed arrangements are equally applicable to both scenarios. It is possible to have a suite of different secondary reservoirs for various conditions that could be prescribed as one-off extra medication to patients already using a standard drug delivery device.

A further feature of a preferred arrangement is that both medicaments are delivered via one injection needle or dose dispenser and in one injection step. This offers a convenient benefit to the user in terms of reduced user steps compared to administering two separate injections. This convenience benefit may also result in improved compliance with the prescribed therapy, particularly for users who find injections unpleasant, or who have dexterity or computational difficulties. The use of one injection instead of two reduces the possibility for user errors and so may increase patient safety.

In a further aspect, an apparatus is described comprising a control unit configured to receive information on a dose of a primary medicament. The control unit is further configured to determine a dose of a fluid agent based at least in part on said dose of said primary medicament and a therapeutic dose profile. The fluid agent may be a medicament, for example a liquid medicament or a liquid solution of a medicament.

In a further aspect, a method is disclosed comprising receiving at a control unit information on a therapeutic dose profile. The method further comprises receiving at the control unit information on a dose of a primary medicament, determining at the control unit a dose of a fluid agent based at least in part on said information on said dose of said primary medicament and the therapeutic dose profile, and initiating administration of said dose of said primary medicament and said dose of said fluid agent in accordance with the therapeutic dose profile.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 3 illustrates a perspective view of a cartridge holder and a back side of the delivery device illustrated in FIG. 1b;

FIG. 4 illustrates a perspective view of a proximal end of the delivery device illustrated in FIG. 1b;

FIG. 5a illustrates a plan view of a digital display of the delivery device after the device has been turned on but before a dose is set;

FIG. 5b illustrates a plan view of the digital display illustrated in FIG. 5a after a dose has been set;

FIG. 6 illustrates a perspective view of the delivery device distal end showing the cartridge;

FIGS. 35a and 35b illustrate a perspective view of yet another exemplary drug delivery device;

FIGS. 36a and 36b illustrate a perspective view of yet another exemplary drug delivery system.

DETAILED DESCRIPTION

Figure 1A:
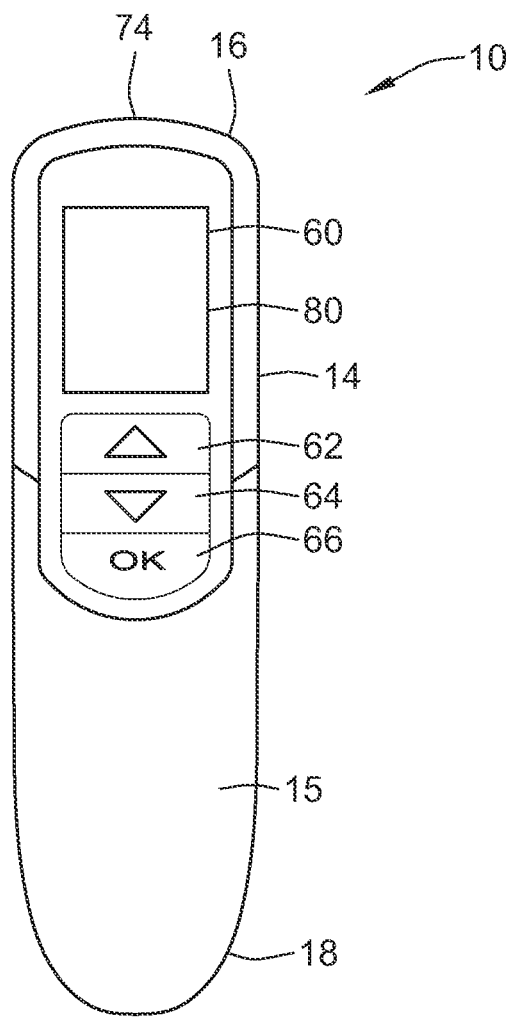
FIG. 1a illustrates a plan view of a programmable drug delivery device in accordance with one aspect of the present disclosure and FIG. 1b illustrates a plan view of a programmable drug delivery device with an end cap removed in accordance with one aspect of the present disclosure.
Figure 1B:
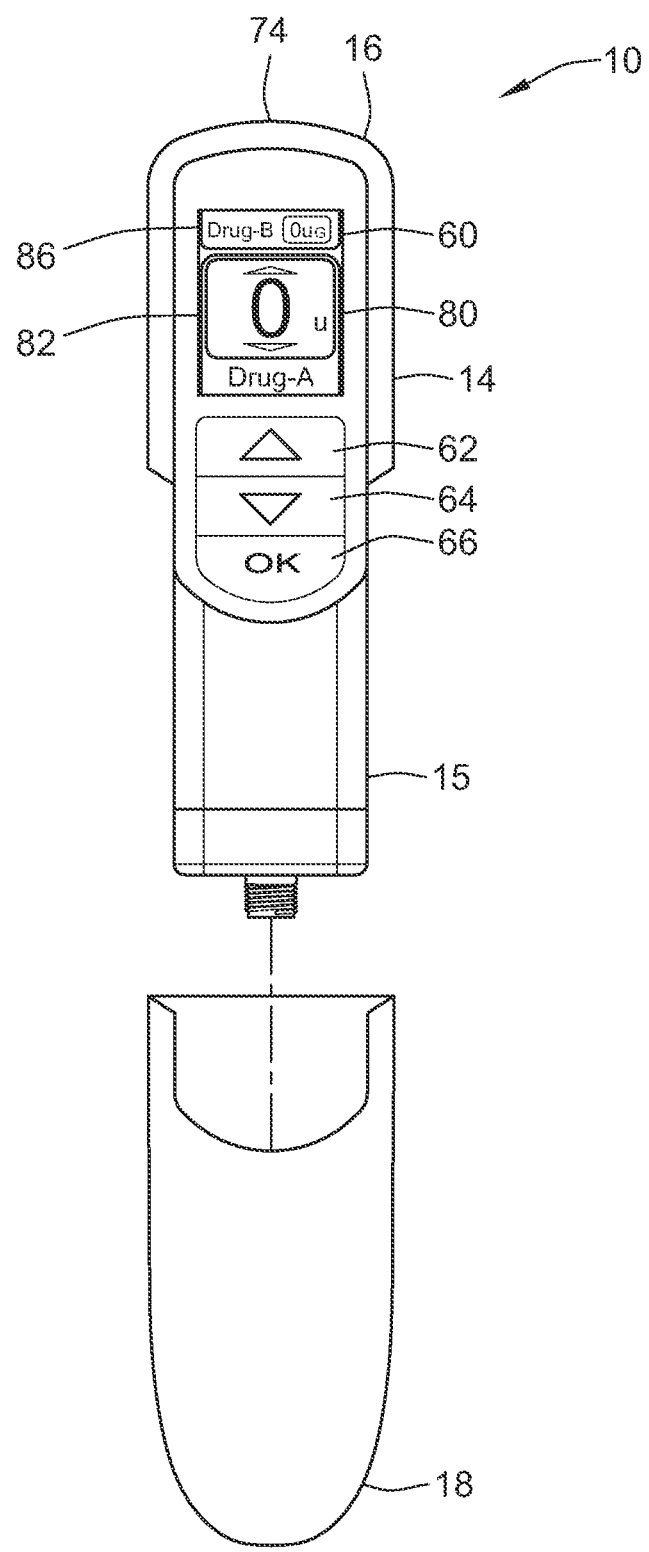
Figure 2:
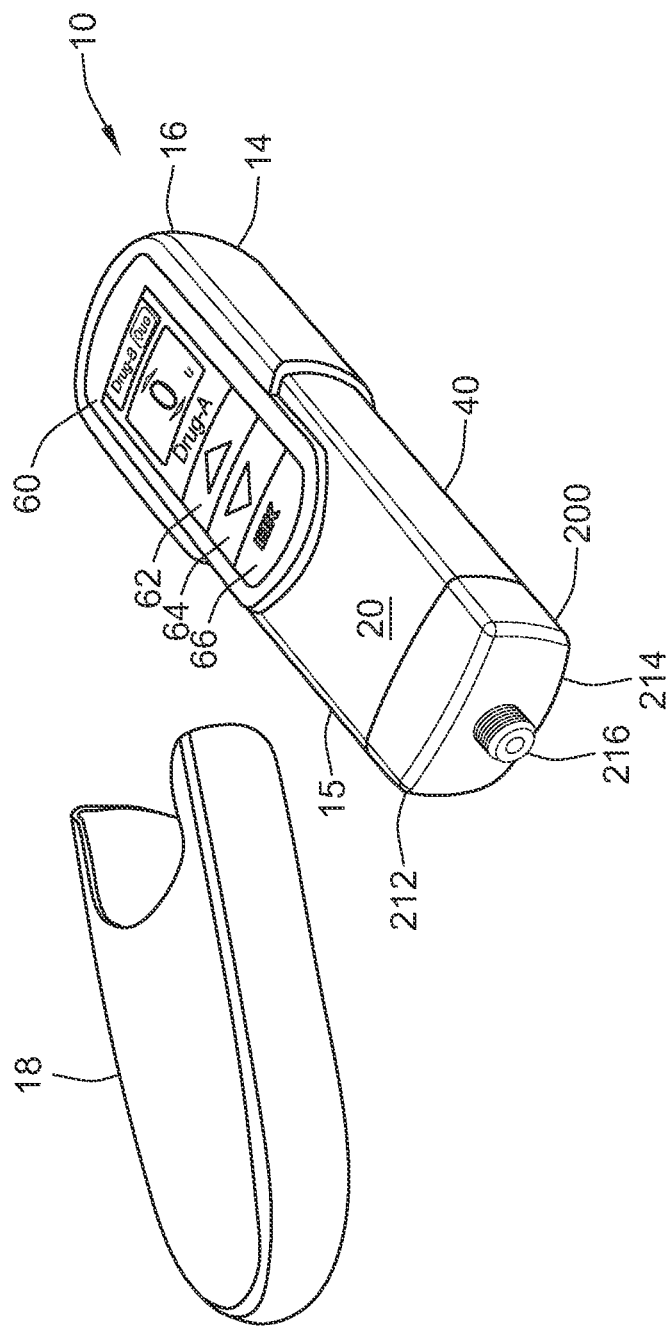
FIG. 2 illustrates a perspective view of the delivery device illustrated in FIGS. 1a and 1b with an end cap of the device removed.

FIGS. 1a and 1b illustrate plan views of a programmable drug delivery device 10 in accordance with one aspect of the present disclosure. FIG. 1a illustrates the device 10 when an end cap 18 is on the device 10. In FIG. 1b, the device 10 is illustrated in a ready mode in that the end cap 18 is off and the device 10 has been turned on so that the digital display 80 is illuminated. When the device is activated with the cap on only cartridge contents, battery status and last dose information will be available for display. When the cover is removed the dose setting screen will be available. FIG. 2 illustrates a perspective view of the delivery device 10 illustrated in FIGS. 1a and 1b with the end cap 18 of the device 10 removed. In FIG. 2, the device is turned on so that the digital display is illuminated. FIG. 3 illustrates a perspective view of a cartridge holder and the back side of the delivery device illustrated in FIGS. 1a and 1b. FIG. 4 illustrates a perspective view of a proximal end of the delivery device 10.

Referring now to FIGS. 1 through 4, there can be seen a micro-processor controlled electro-mechanical drug delivery device 10 in accordance with the present disclosure. Preferably, this drug delivery device 10 is generally rectangular in shape comprising generally rounded ends so as to easily fit in a user's shirt pocket and is also compact enough to fit in a hand bag.

As will be described in greater detail below, the drug delivery device 10 contains a micro-processor control unit that operates an electro-mechanical drive that is used to deliver at least two drugs (a first or primary medicament and a second or secondary medicament) during a single dosing operation. This enables the drug delivery device 10 to provide, for example, a primary medicament such as a long acting insulin along with a secondary medicament such as a GLP1 as a combination therapy. Such combination therapy may be defined by one of a plurality of therapeutic profiles stored in a memory device that is coupled to the micro-processor contained within the device 10.

The drug delivery device illustrated in FIGS. 1 through 4 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body. Other types of connection mechanisms may also be used such as frictional fits or snap fits provided by way of a clip feature.

As will be described in greater detail below, the main body 14 contains a micro-processor control unit, an electro-mechanical drive train, and at least two medicament reservoirs. When the end cap or cover 18 is removed from the device 10 (as illustrated in FIGS. 1b, 2, 3, and 4), a dispense interface 200 (see FIG. 3) is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." As illustrated, the first dose setting button 62 resides above the second dose button 64 which is positioned above the OK button 66. Alternative button arrangements may also be used. As just one example, the first buttons 62 and a second button 64 may, as a pair, be rotated through 90 degrees and sit underneath the screen, with each button being adjacent to a screen area. In such an arrangement, the first and second buttons could be used as soft keys to interact with icons on the user digital display 80. In addition, along the most proximal end of the main body, an injection button 74 is also provided (see e.g., FIG. 4).

Utilizing micro-processor controlled human interface elements such as an operator panel (e.g., hard keys, buttons or soft keys with the key legend appearing on the display screen), setting the dose of the primary medicament allows the control unit to compute or determine the fixed dose of the second medicament. In one preferred arrangement, a computerized electronic control unit computes the dose of the second medicament. Most preferably, the computerized electronic control unit computes the dose of the second medicament based at least in part on a therapeutic dose profile that is stored in a memory device coupled to the micro-processor. Such a therapeutic profile may or may not be user or caregiver selectable. Alternatively, this profile may not be user selectable. As will be explained in greater detail below, a plurality of different such dose profiles may be stored on a memory storage device in the drug delivery device. In one arrangement, the preferred memory storage device comprises Flash memory of the micro-processor. An optional storage device could comprise an EEPROM that is coupled via a serial communication bus to the micro-processor of the control unit.

FIG. 2 illustrates a perspective view of the drug delivery device 10 of FIGS. 1a and 1b with the cover 18 removed so as to illustrate the main body 14 and a cartridge holder 40. By removing the cover 18 from the device, a user is provided access to the cartridge holder 40 and also the dispense interface 200. In one preferred arrangement, this cartridge holder 40 can be removably attached to the main body 14. In this arrangement, and as illustrated in FIG. 6, the cartridge holder 40 may contain at least two cartridge retainers 50 and 52. Each retainer is configured so as to contain one medicament reservoir, such as a glass cartridge. Preferably, each cartridge contains a different medicament. However, in alternative drug delivery device arrangements, more than two cartridge retainers may be contained within the cartridge housing.

Figure 10:
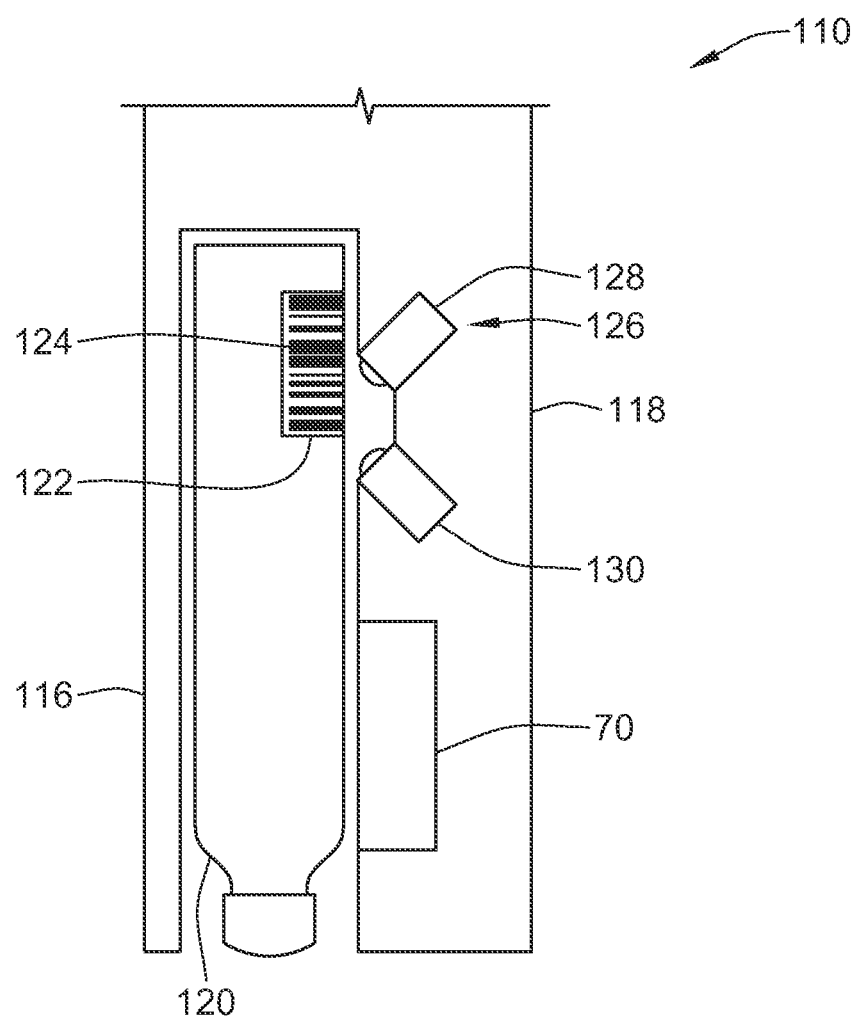
FIG. 10 illustrates one type of cartridge dedication system that may be used with the cartridge holder.

In one preferred arrangement, each cartridge retainer 50, 52 may be provided with a cartridge detecting system, such as the cartridge detecting system illustrated and described with respect to FIG. 10. Such a cartridge detecting system may comprise a mechanical or electrical switch that can be used to determine if a cartridge has been correctly inserted into the retainers 50 and 52. Ideally, such a detection system can determine if the correct size cartridge has been properly inserted into the retainer.

In addition, at the distal end of the cartridge holder 40, the drug delivery device illustrated in FIG. 2 includes a dispense interface 200. As will be described in relation to FIG. 11, this dispense interface 200 includes a main outer body 212 that is removably attached to a distal end 42 of the cartridge housing 40. As can be seen in FIGS. 2 and 3, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

At a first end or a proximal end 16 of the main housing 14, there is provided a control panel region 60. This control panel region 60 comprises a digital display, preferably an Organic Light Emitting Diode (OLED) display 80 along with a plurality of user interface keys such as push buttons. Alternatively, this region could comprise a touch screen and icons on the display. A further option would be a display screen with a joystick, a control wheel and/or possibly push buttons. In addition, the control panel region may also comprise a swipe section so as to either increase or decrease the dose size or provide other means by which a user could operate the device 10. Preferably, the human interface controls may be configured to provide tactile, audible and/or visual feedback.

The digital display 80 may be part of a user interface that allows the user to interact with the device 10. As explained in greater detail below, this display provides a visual indication of device operation such as dose setting, dose administration, injection history, device errors, etc. The digital display 80 can also display various drug delivery device parameters. For example, the display can be programmed to display an identified medicament contained in either medicament containers and also provide a visual confirmation that the correct cartridge and therefore medicament is being used. In addition, the display can also provide dose history information such as the time since the last dose has been administered, battery level, dose size set, device status, dose dispense status, dose history information, warnings, and errors.

In addition, the display 80 may also provide the time and date and be used to set a current time and date. The display may also be used to provide the user with training information as to how the device should be used and operated. Alternatively, the display may be used to educate the user on diabetes or other therapy information via instructional videos. The display may also be used to communicate with, or receive feedback from a health care professional via the wireless or wired communication link such as USB to a PC and then potentially via the internet, or via a mobile phone coupled to the device using a wired or wireless link such as a Bluetooth™ link, a WLAN link, and/or the like. The display may also be used to configure a device communication link: that is, used for device set up and enter passwords for a data link, such as a Bluetooth data link. In addition, the display may be used to provide drug delivery device priming information or possibly an indication of the orientation and/or relative position of the device. For example, a micro-electro-mechanical accelerometer could be provided within the device so that the device will have the intelligence to know if the user is using the device to perform a safety or priming shot (i.e., having the distal end of the device pointing upwards) or using the device to perform a dose administration step (i.e., having the distal end of the device pointing downwards).

The display may also potentially be used as a diary or life style calendar and perhaps communicate with a patient's BGM and perhaps store and display blood glucose data. The display could also indicate a dwell period, possibly proportional to a dose size, following the delivery of a dose. The display could indicate if the device is armed i.e., ready to deliver a dose and also be used to provide an indication if the dose is outside of expected limits.

In addition, by manipulating certain other buttons, the display can be used to display information stored in the control unit. For example, such stored information could include user or patient information. Such user or patient information could include their name, their address, their health number, contact details, their prescribed medication or dosage regime.

In addition, there is also the opportunity to include calendar information, which could include blood glucose readings, the size of last dose taken, exercise taken, state of health, the time these events occurred including meal times, etc. Certain key events can also be stored and viewed. For example, such key events could include device failures that could potentially result in an over or under dose, cartridge changes, priming shots, reading the dose history, removing the cap, removing the dose dispenser, removing the dispense interface, time since manufacture, time since first use along with other similar types of information and data.

The digital display could also allow the user access to a time reference maintained by the device. Such a time reference could keep track of the current time and date. This clock may be set by the user via the interface or alternatively, via a data link (e.g., USB or IRDA) provided on the device. In addition, the time reference may be provided with a permanently connected battery backup so as to maintain the passage of time if and when the main battery has been removed or is flat. This time reference may be used to determine when the last dose was taken, which can then be displayed on the display. This time reference may also be used to store certain key events. Such events could include the time and date of the following: the last dose; whether any drug delivery device errors occurred; cartridge changes; any parameter changes, any changes in therapeutic profiles; dispense interface changes; and time since manufacture.

As previously mentioned, FIG. 1*b* illustrates one arrangement of the drug delivery device 10 after the user has turned the device on. One way in which a user may turn the device on is for the user to press the "OK" button 66 provided on the control panel region 60. Alternatively, the device 10 can be programmed to be turned on by removing the end cap 18. The OK button 66 may then be used when the device 10 has gone into a sleep mode after a certain period of inactivity. The sleep mode may be indicated by a possibly blank display screen. Preferably, when the cap 18 is placed back upon the device, it may be possible to review via the display 80 certain dose or dosing history data by pressing one of the human interface elements, such as the OK button 66.

Once the device is turned on, the digital display 80 illuminates and provides the user certain device information, preferably information relating to the medicaments contained within the cartridge holder 40. For example, as illustrated in FIGS. 1 and 5, the user is provided with certain information relating to both the primary medicament (Drug A) and the secondary medicament (Drug B). Preferably, the display comprises at least two display regions 82, 86 containing medicament information. The first display region 82 provides the user information relating to the primary medicament: the type of medicamen—"Drug A" and the amount of Drug A that has been selected by the user—"0 Units." In addition, the second display region 86 provides the user with information relating to the secondary medicament: the type of medicament—"Drug B" and the amount of Drug B that has been calculated by the device based on the amount of Drug A selected by the user and on the particular therapeutic profile—"0 μ Grams." As those of ordinary skill in the art will recognize, if in an alternative arrangement the drug delivery device 10 contained three medicaments and then used to administer a combination therapy of these three medicaments, the digital display 80 would be modified so as to comprise at least three display regions containing information for at least these three medicaments.

Where the size of the second dose is determined from the size of the first it may not be necessary to indicate the size of the second dose and hence an alternative embodiment of the display graphics may be used, for example an "O.k." indication, such as a green dot, a green check mark, or the letters "O.k.".

Aside from the digital display 80, the control panel region 60 further comprises various user interface keys. For example, as illustrated in FIGS. 1*a* 1*b*, 2 and 4, the control panel region 60 of the drug delivery device 10 further provides the following user interface keys:

a. first dose setting button 62,
b. a second dose setting button 64, and
c. an OK or Enter button 66.

The first and second dose buttons 62, 64 may be manipulated so as to allow a user of the device 10 to either increase or decrease a selected dose of the primary medicament "Drug A" to be delivered. For example, to set or increase a primary medicament dose amount, a user could toggle the first dose setting button 62. The first display region 82 would provide a visual indication to the user of the amount he or she is setting.

In the event that a user wants to decrease a previously set dose, the second dose setting button 64 may be toggled or pushed so as to decrease the set dose. Once the user has selected the amount of the primary medicament, the user may then push the "OK" button 66. Pushing the OK button 66 may instruct the device 10 to compute the corresponding dose of the secondary medicament "Drug B". Alternatively, the dose of the secondary medicament may be determined when the dose of the first medicament is set or changed.

In an alternative display arrangement, the display 80 can display the calculated amount of the secondary medicament Drug B for every incremental change of Drug A. Thereafter, the OK button 66 could then be used. For example, pressing and holding this OK button 66 for a certain period of (e.g., 2 seconds) could be used by the user to confirm the set and calculated dose and thereby arming the device 10 ready for delivery. The combined dose could then be dispensed through a single dose dispenser by pressing the injection button 74. In one preferred arrangement, the device armed condition may be available for a limited period, for example, 20 seconds or so. In an alternative arrangement, the arm feature may not be included.

FIG. 5*a* illustrates the display 80 of device 10 illustrated in FIG. 1*b* after the device has been turned on but before a user sets a first dose of the primary medicament Drug A. FIG. 5*b* illustrates this display 80 after a user has set a first dose of the primary medicament Drug A and after the device has computed the corresponding amount of the secondary medicament Drug B. As illustrated in FIG. 5*b*, the user has set a 15 Unit dose of the primary medicament Drug A and this is confirmed by what is displayed in the first display region 82. After the device 10 computes the secondary dose of the second medicament Drug B, this is also indicated by what is displayed in the second region 86. For example, in this situation, the device 10 calculated a dose of 20 μ Grams for Drug B based in part on a 15 Unit dose of the primary medicament Drug A and based in part on one of the algorithms stored within the device.

This combined dose, 15 Units of the primary medicament Drug A and 20 μ Grams of the secondary medicament Drug B, can then be injected. As may be seen from FIG. 4, at a proximal end of the main body 14 of the device 10, an injection button 74 is provided for injecting this combined dose. Alternatively, this dose inject button 74 could be provided elsewhere on the main housing 14 such as on the control panel region 60.

Other information that may be taken into account when calculating the amount of the second medicament may be the time interval since the previous dose of either the first or the second medicament. For example, the following description provides an example algorithm and process that may be used in the calculation of the size of the dose to be dispensed from the second medicament. This algorithm maybe illustrated in a flowchart 150 provided as FIG. 7.

Figure 7:
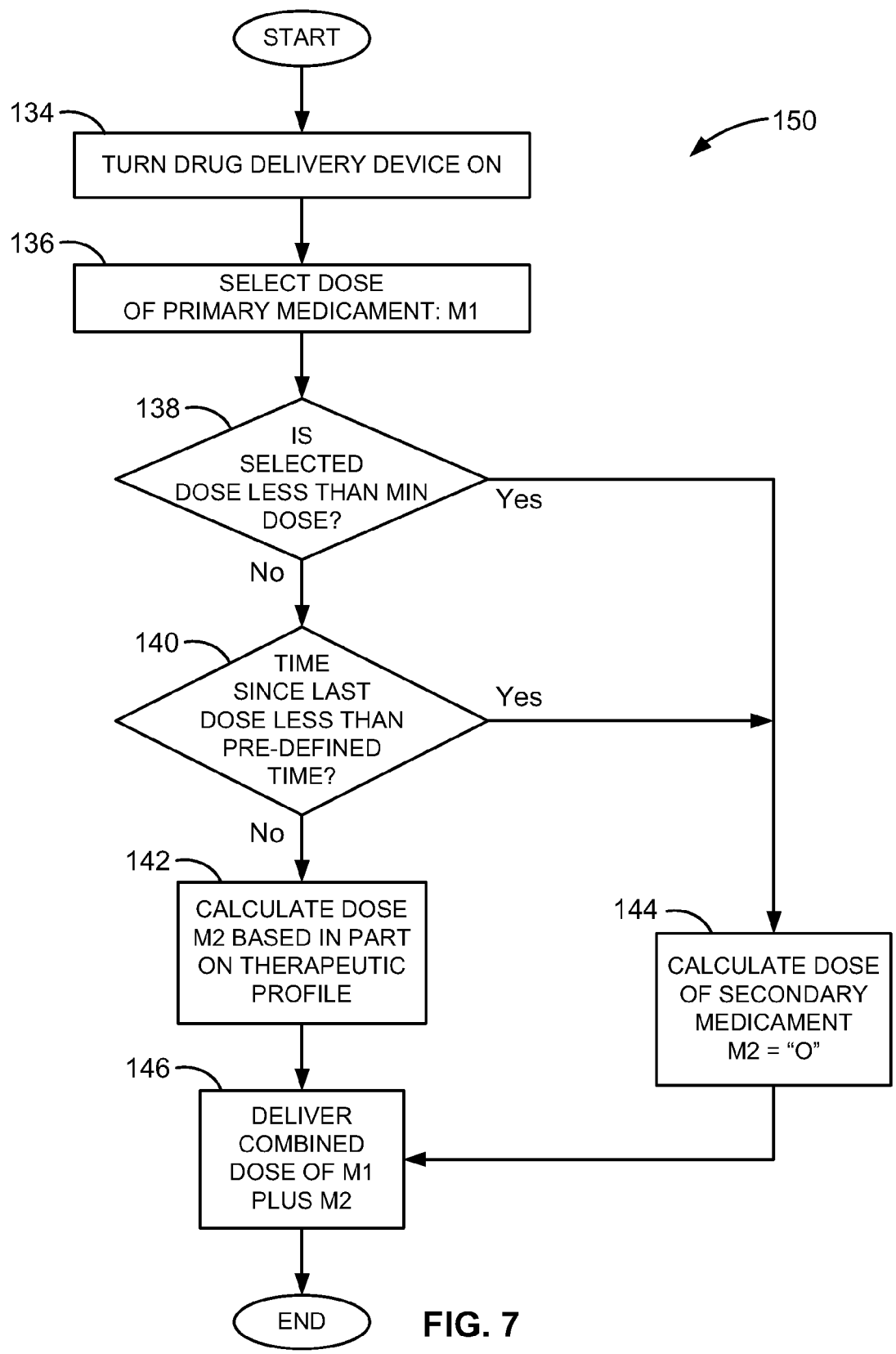
FIG. 7 illustrates a flowchart of one algorithm that can be programmed into the drug delivery device illustrated in FIGS. 1a and 1b.

As may be seen from the flowchart 150 provided in FIG. 7, first a user begins the dose selection process by turning the device on at step 134. Then, at step 136, the user selects the size of the dose to be delivered from the first medicament M1 in the first cartridge and then presses the OK button to confirm. At step 138, the microcontroller determines if the selected dose size of the first medicament M1 is less than a minimum dose threshold for the first medicament (e.g., 5 units). If it is determined that the selected dose size is indeed less than the minimum dose threshold, the process proceeds to step 144 where the calculated dose of the second medicament M2 is then computed as a zero dose. Then, the process moves to step 146 where the dose (comprising only a selected dose of the primary medicament) is administered.

If the selected dose size is determined to be greater than or equal to this minimum dose threshold, the process 150 proceeds to step 140. At step 140, the microcontroller determines if the time interval since the previous injection is less than, or equal to the predefined threshold (e.g., 18 hours). If the answer to this inquiry is yes, the process 150 proceeds to step 144 where the size of the dose from the second medicament M2 would be calculated as equal to a zero ("0") dose. Then, the process moves to step 146 where the dose (comprising only a selected dose of the primary medicament) is administered.

Alternatively, if the answer to both inquiries at steps 138 and 140 are no, then process 150 would proceed to the step 142. At step 142, the microcontroller would compute the dose of the secondary medicament M2 based at least in part on a stored therapeutic profile. If a third medicament would be provided in the drug delivery device, the microcontroller would compute a dose of a third medicament based at least in part on a stored therapeutic profile as well. This later profile may or may not be the same profile that is used to calculate the dose of the secondary medicament.

Therefore, if a user selects a dose size of the primary medicament M1 at step 136 that is equal to, or greater than, a certain minimum dose threshold for the first medicament (e.g., 5 units), and the time interval since the previous injections is greater than the predefined threshold (e.g., 18 hours) then the predefined dose of the secondary medicament from the second cartridge (e.g., 0.5 units) will be delivered when the injection is administered at step 146.

Figure 8:
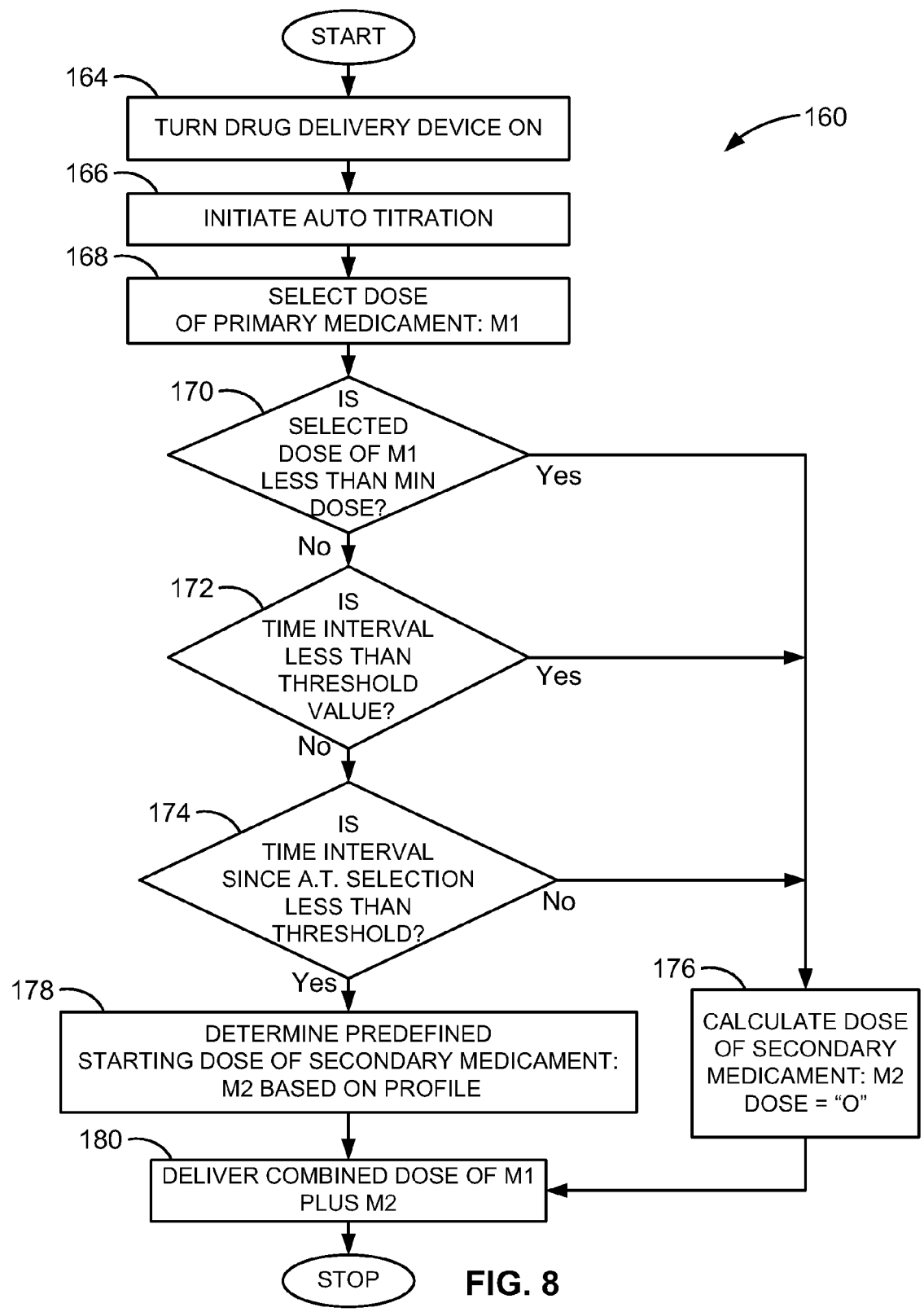
FIG. 8 illustrates a flowchart of another algorithm that can be programmed into the drug delivery device illustrated in FIGS. 1a and 1b.

The disclosed drug delivery device 10 may also be programmed with an auto titration algorithm. As just one example, such an algorithm may be used where the dose of the second medicament needs to be increased over a period of time to allow a patient to get used to the second medicament, such as is the case for a GLP1 or GLP1 analogs. An exemplary auto titration algorithm is presented in a flowchart 160 illustrated in FIG. 8.

In one arrangement, after the device is turned on at step 164, a user initiates an auto titration mode of operation by manipulating one of the keys provided on the control panel. This is represented at step 166. Alternatively, this auto titration mode of operation could be automatically activated. For example, the auto titration mode of operation could be automatically activated when the drug delivery device 10 is first used, for example, when a battery is first connected to the device, when the battery is first charged, or when a profile is loaded into the device and selected by a user. After step 166, a prompt on the digital display 80 may ask a user for a password and then to confirm that the auto titration algorithm is indeed desired by the patient. In an alternative embodiment, a prompt on the digital display 80 may ask the user for a confirmation only.

Aside from using a stored algorithm for operating the device in an auto titration mode, this auto titration mode might be achieved via providing a user with cartridges containing the same medicament but with different strengths or concentrations. One disadvantage of such a scenario is that the provider of such cartridges would have to produce cartridges in at least two different strength concentrations of drugs rather than through smaller doses from a standard strength cartridge. If different strength cartridges are used, then the device may be programmed not to provide the auto-titration functionality. If this functionality is optional and patient determined, then such a function could be accessed through the digital display 80 via a 'menu' button (or other similar user interface element).

At step 168, a user selects a dose of the primary medicament Ml. Then, at step 170, the microcontroller determines if the selected dose size is less than a minimum dose threshold for the first medicament (e.g., 5 units). If the microcontroller determines that the selected dose size is less than a minimum dose threshold for the first medicament, the process 160 proceeds to step 176. At step 176, the microcontroller determines that the calculated dose of the secondary medicament M2 should be a zero ("0") dose.

If at step 170 the microcontroller determines that the selected dose size of M1 is not less than a minimum dose threshold for the first medicament, the process 160 proceeds to step 172. At step 172, the microcontroller computes a time interval since the previous dose administration and determines if this computed time interval is less than, or equal to a predefined threshold (e.g., 18 hours). If at step 172 the microcontroller determines that this computed time interval is less than, or equal to a predefined threshold, the process 160 proceeds on to step 176. At step 176, the microcontroller determines that the calculated dose of the secondary medicament M2 should be a zero ("0") dose.

Alternatively, if at step 172, the microcontroller determines that this computed time interval since the previous injection is not less than, or equal to a predefined threshold, the process proceeds to step 174.

If the microcontroller determines that the selected dose size is equal to, or greater than, the minimum dose threshold for the first medicament (e.g., 5 units) at step 170 and determines that the time interval since the previous injection is greater than the predefined threshold (e.g., 18 hours) at step 172, the process proceeds to step 174. At step 174, the microcontroller determines whether the time interval since the auto-titration feature was activated is less than a predefined threshold (e.g., 1 week). If at step 174 the microcontroller determines that the time interval since the auto-titration feature was activated is greater than this predefined threshold, the process 160 moves to step 176 where a zero "0" dose of M2 is determined.

Alternatively, if the microcontroller determines that the time interval since the auto-titration feature was activated is less than the predefined threshold at step 174, the process moves to step 178. At step 178, the microcontroller determines a predefined starting dose of the secondary medicament based in part on a therapeutic profile. Then, at step 180, the predefined starting dose from the second cartridge (e.g., 0.25 micro Grams) M2 along with the previously selected dose of the primary medicament M1 from step 168 will be delivered during an injection step.

Therefore, in accordance with the auto titration flowchart 160, if the selected dose size is equal to, or greater than, the minimum dose threshold for the first medicament (e.g., 5 units) and the time interval since the previous injections is greater than the predefined threshold (e.g., 18 hours) and the time interval since the auto-titration feature was activated is greater than a predefined threshold (e.g., 1 week) then the predefined maintenance dose from the second cartridge (e.g., 0.5 units) will be delivered when the injection is taken at step 180. If the calculated responses to the steps 170 and 172 are yes or if the response to step 174 is no, then the dose that is administered would comprise only the selected dose of the primary medicament from step 168.

Aside from the user interface keys, the drug delivery device may also comprise a sounder or a sound control. For example, the device may have a sounder that generates a range of tones. Such tones could be provided so as to indicate when a button is pressed, when certain key events occur (e.g., after a dose is set, after the completion of a dose delivery, etc.), warnings that the device is not working correctly or if an incorrect cartridge has been inserted, if the device experiences certain operational errors, or if an alarm condition is triggered. The volume of the sounder may be set or configured by using a menu system controlled by the human interface elements or alternatively through a dedicated volume control button.

The main housing portion is preferably coupled to a proximal end of the cartridge holder 40. Preferably, this cartridge holder 40 comprises at least two separate cartridge retainers that are configured to hold two reservoirs of medicament. Depending on the reservoirs, these two retainers may or may not be similarly sized. For example, FIG. 3 illustrates a back side of the drug delivery 10 illustrated in FIGS. 1*a* and 1*b* and illustrates one of the cartridge retainers 52. FIG. 6 illustrates a distal end of the cartridge holder of the drug delivery device illustrated in FIGS. 1*a* and 1*b* and illustrates both the first and the second cartridge retainers 50, 52. In one preferred arrangement, the first cartridge retainer 50 is configured for receiving a first cartridge 90 containing a primary medicament 92 and the second cartridge retainer 52 is configured for receiving a second cartridge 100 containing a secondary medicament 102. The first and second cartridges 90, 100 may or may not be of similar size and/or dimensions.

As illustrated in FIG. 6, the cartridge housing 40 comprises a first window 46 residing along a first side portion of the cartridge housing. Similarly, the cartridge housing 40 comprises a second window 47 residing along a second side portion of the cartridge housing 40. This cartridge housing 40 comprises two cartridge retainers 50, 52 and these retainers are positioned essentially side-by-side one another. Once the cap 18 is removed from the drug delivery device 10, the windows 46, 47 enable a user to view the medicaments contained within the cartridges and monitor the amount of medicament remaining in each reservoir. For example, as may be seen from FIG. 6, the first window 46 allows the user to monitor the primary medicament 92 contained within the first cartridge 90 while the second window 47 allows the user to monitor the second medicament 102 contained within the second cartridge 100. The visible cartridge contents could be confirmed by what is displayed on the digital display 80.

In this illustrated arrangement, the first cartridge 90 contains a primary medicament 92 and the second cartridge 100 may contain a secondary medicament 102. Preferably, both the first and the second cartridges contain multiple doses of each medicament 92, 102, respectively. Each cartridge is self-contained and provided as a sealed and sterile cartridge. These cartridges can be of different volumes and replaceable when empty or they can be fixed (non-removable) in the cartridge holder 40. They can also have a pierceable seal or septa at a distal end of the cartridge and configured to accept needle cannula.

Various cartridge holder arrangements may be used with the drug delivery device illustrated in FIGS. 1-6. As just one example, the cartridge holder 40 may comprise separately shaped cartridge retainers 50, 52. As just one example, the first cartridge retainer 50 may be shaped to receive a cartridge having a first volume while the second cartridge retainer 52 may be shaped to receive a cartridge having a second volume. As just one example, in one preferred arrangement, the primary medicament 92 contained in the first cartridge 90 may comprise a long acting insulin whereas the second medicament 102 contained within the secondary cartridge 100 may comprise a GLP1 or like analog.

As such, in one preferred arrangement, the volume of the first cartridge 90 may be a standard 300 Unit cartridge and therefore the first cartridge retainer 50 must be geometrically configured for such a volume. In contrast, the volume of the second cartridge 100 may be a smaller volume (e.g., in the order of 20 Units) and therefore must be geometrically configured to receive such a smaller volume cartridge. As those of ordinary skill in the art with recognize, other cartridge and cartridge retainer arrangements and geometries are possible as well.

Figure 9:
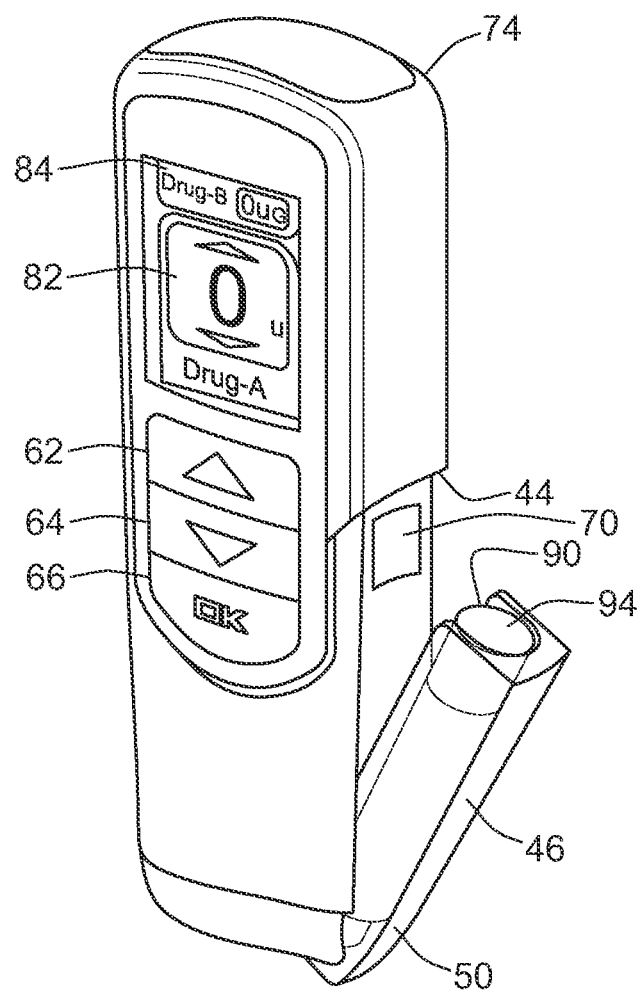
FIG. 9 illustrates a perspective view of the cartridge holder illustrated in FIG. 3 with one cartridge retainer in an open position.

In one preferred arrangement, the first and a second cartridge retainers 50, 52 comprise hinged cartridge retainers. These hinged retainers allow user access to the cartridges. For example, FIG. 9 illustrates a perspective view of the cartridge holder 40 illustrated in FIG. 2 with the first hinged cartridge retainer 50 in an open position. FIG. 9 illustrates how a user might access the first cartridge 90 by opening up the first retainer 50 and thereby having access to the first cartridge 90. A user might access the second cartridge 100 contained in the second hinged retainer 52 in a similar manner. Of course, if different sized cartridges are used, a user might access the second cartridge 100 in a different manner.

As illustrated in at least FIGS. 9 and 10, the drug delivery device 10 may comprise a cartridge detection system. Such a system may be used so as to confirm that the cartridge 90 has been properly inserted into the first cartridge retainer 50. In this illustrated arrangement, the cartridge detection device 70 is provided along an inner portion of the cartridge holder 40. An alternative location of the detection device may also be used.

In one preferred arrangement, the first or primary cartridge 90 containing first medicament and the second or secondary cartridge 100 containing the second medicament are of similar dimensions. In a more preferred arrangement, the first cartridge 90 is a different size than the second cartridge. As just one example, the first medicament (e.g., a long acting insulin) could be provided within a 3 ml cartridge and this cartridge loaded into the first cavity. In addition, the second medicament (e.g., a GLP1) may be provided within a shortened 1.7 ml cartridge and could be loaded into the second cavity. Because the second hinged retainer contains a smaller sized cartridge, the second retainer would be sized differently than the first retainer. In a most preferred arrangement, the primary cartridge holder is designed so as to accept a 3 ml cartridge of insulin and the secondary holder is designed so as to accept a 1.7 ml cartridge of a GLP1. However, those of skill in the art will readily recognize, alternative cartridge holder structures and cartridge configurations could also be used.

In one arrangement, the cartridge holder 40 includes a cartridge dedication or coding system, such as a mechanical or an electronic cartridge dedication or coding system. Such a system would help to ensure that only a correctly coded cartridge and therefore the correct medicament could be loaded into each cartridge retainer. An electronic coding system that is able to detect a drug type, expiry date or other similar information would be a preferred arrangement. In such an electronic system, the microprocessor control unit could be programmed so that only a properly coded cartridge (and therefore the proper medicaments) would be acceptable in such a system. In such a coded system, the control unit could be programmed with an electronic lock-out so as to lock out or disable the operator interface if an improperly coded cartridge was detected. Preferably, if such an incorrect cartridge were loaded, an error message would be displayed on the digital display 80 so as to notify the user that an incorrect cartridge (and therefore perhaps an incorrect medicament) had been loaded. Most preferably, if such an incorrect cartridge were loaded, the drug delivery device 10 could be programmed so as to lockout the user interface keys and prevent the user from setting a dose.

FIG. 10 illustrates one type of cartridge identification system 110 that may be used with the cartridge housing of drug delivery device 10. For example, FIG. 10 illustrates a cartridge 120 (similar to either the first or the second cartridge 90, 100) residing in a cartridge retainer 116 of a cartridge holder 118. Cartridge retainer 116 may be similar to the cartridge retainers 50, 52 illustrated in FIGS. 3 and 6. A cartridge 120 is illustrated as being nested within an internal cavity of the cartridge retainer 116. A label 122 is provided along an outer surface of the cartridge 120 and a bar code 124 is provided along a portion of this label 122.

In FIG. 10, the cartridge identification system 110 comprises a one dimensional ("1D") bar code reading system. In such a cartridge identification system 110, the barcode is provided along the cartridge surface and this bar code is an optical machine-readable representation of certain information. Alternatively, a two dimensional bar code reader could also be used. In such an arrangement, patterns of squares, dots, hexagons and other geometric patterns within images may be provided either on the cartridge outer surface itself or on a cartridge label. In addition, a cartridge detection device 70 may be provided along an inner surface wall of the system 110.

As just one example, the cartridge holder 118 may comprise a bar code reader 126. In one arrangement, this reader could comprise a 1D bar code reader comprising a light source 128 and a photo diode 130 and these two elements could be provided along an inner surface of the cartridge housing 118 adjacent the cartridge retainer 116. As illustrated, the light source 128 and a photo diode 130 may placed next to each other and directed towards the barcode on the cartridge. To read the bar code 124 provided on the label 122 of the cartridge 120, the light source 128 illuminates various lines provided on the label 122 as the cartridge is inserted into the cartridge housing 118. This light is then reflected and the photo diode 130 measures the intensity of the light reflected back from the light source 128 and a waveform is generated. The micro-processor coupled to this cartridge identification system 110 uses this generated waveform to measure the widths of the bars and spaces of the bar code 124. For example, dark bars in the bar code absorb the illuminated light while the white spaces reflect light.

As such, the voltage waveform generated by the photo diode will represent a duplicate of the bar and space pattern in the bar code. This waveform is then decoded by an algorithm provided in the micro-processor. Alternatively, a 2D barcode reader could also be used. One advantage of such a reader is that relative motion between the cartridge and the cartridge holder would not be required.

Utilizing such cartridge identification in the disclosed drug delivery device 10 results in certain advantages. For example, such a cartridge identification arrangement can provide a method of retrieving information from the cartridges to determine the manufacturer or supplier of the cartridge. Such a system could also determine the type of medicament contained within the cartridge and then may also determine information relating to the drug contained within the cartridge. For example, the cartridge identification system could determine whether the cartridge that was inserted into the first retainer that is supposed to contain the primary medicament actually comprises a cartridge containing such a primary medicament. Such an identification scheme could comprise either a passive or active type of identification scheme. For example, it could comprise a passively (typically mechanical) or active (typically electrical) identification scheme. Such cartridge identification schemes may comprise identification through a microchip interface or through a radio frequency identification (RF-ID) interface. The cartridge may then comprise a readable memory comprising information about the cartridge. The memory may also be writeable, for example to store information on the used number of units, or information on an estimated remaining content in the cartridge and the date first used. The remaining content may be given in number of units, mg, ml and/or the like. The information on the remaining content may be updated when content has been expelled from the cartridge.

In an alternative arrangement, the cartridge holder 40 may be provided as a disposable cartridge holder. For example, in such an arrangement, a medical device supplier or a medicament supplier could supply the cartridge holder containing the two medicaments and these would not be replaceable by the end user. Therefore, once either the primary or secondary medicament of such a cartridge holder has been expended, the entire cartridge holder is removed from the drug dispensing portion of the drug delivery device and is discarded. Thereafter, the user or patient could then attach a new cartridge holder containing two fresh cartridges to the drug dispensing portion of the drug delivery device.

The disposable nature of such a cartridge holder would provide a number of advantages. For example, such a cartridge holder would help to prevent inadvertent medicament cross use: that is, using an incorrect primary or secondary medicament within the cartridge housing. Such an arrangement could also help prevent tampering of the medicaments and could also help eliminate counterfeit products from being used with the drug delivery device. In addition, the cartridge holder may be connected to the device main body where the device main body comprise a one dimensional ("1D") bar code reading system. Such a coding system could comprise a system similar to the coding system 110 discussed above.

Figure 11:
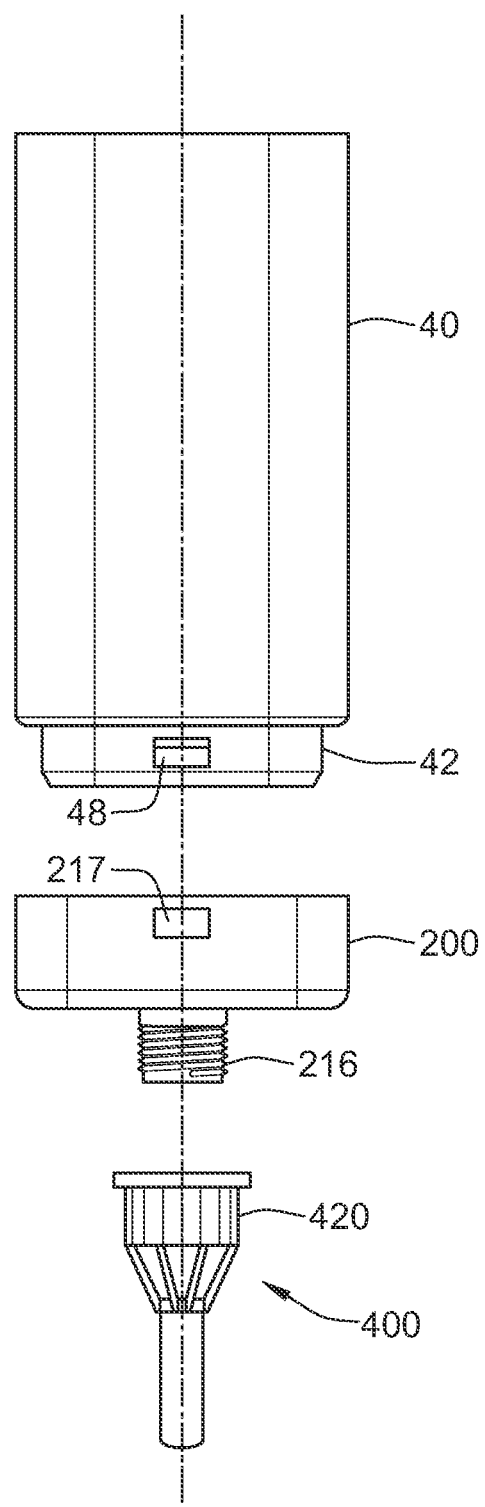
FIG. 11 illustrates a dispense interface and a dose dispenser that may be removably mounted on a distal end of the delivery device illustrated in FIGS. 1a 1b, and 2.

As mentioned above when discussing FIGS. 2 and 3, a dispense interface 200 is coupled to the distal end of the cartridge holder 40. FIG. 11 illustrates a flat view of the dispense interface 200 unconnected to the distal end of the cartridge holder 40. A dose dispenser or needle assembly that may be used with the interface 200 is also illustrated and is provided in a protective outer cap 420.

Figure 12:
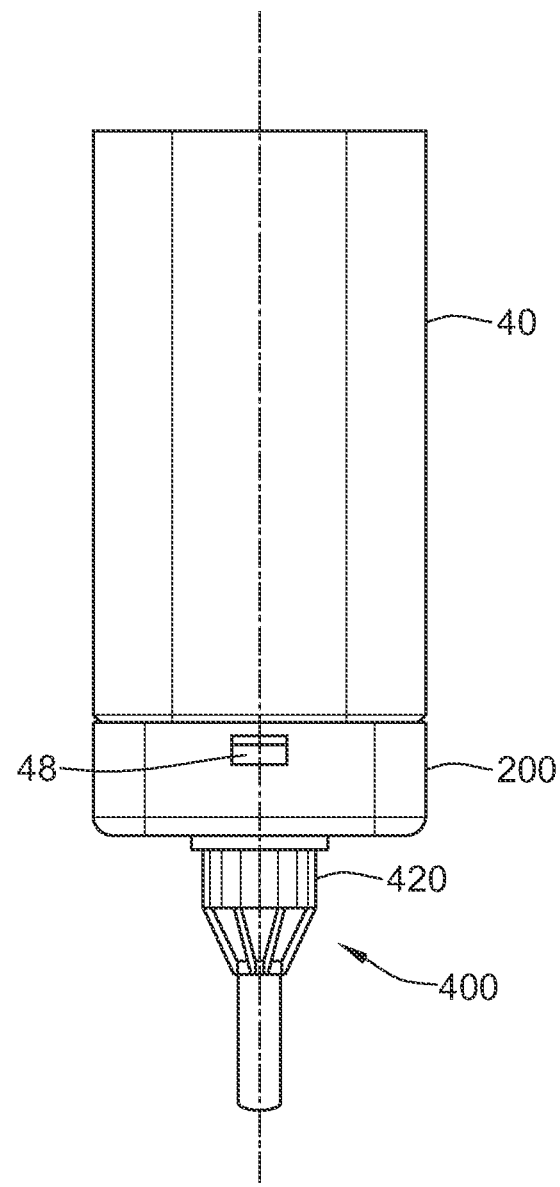
FIG. 12 illustrates the dispense interface and the dose dispenser illustrated in FIG. 11 mounted on a distal end of the delivery device illustrated in FIGS. 1a 1b, and 2.

In FIG. 12, the dispense interface 200 illustrated in FIG. 11 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 13:
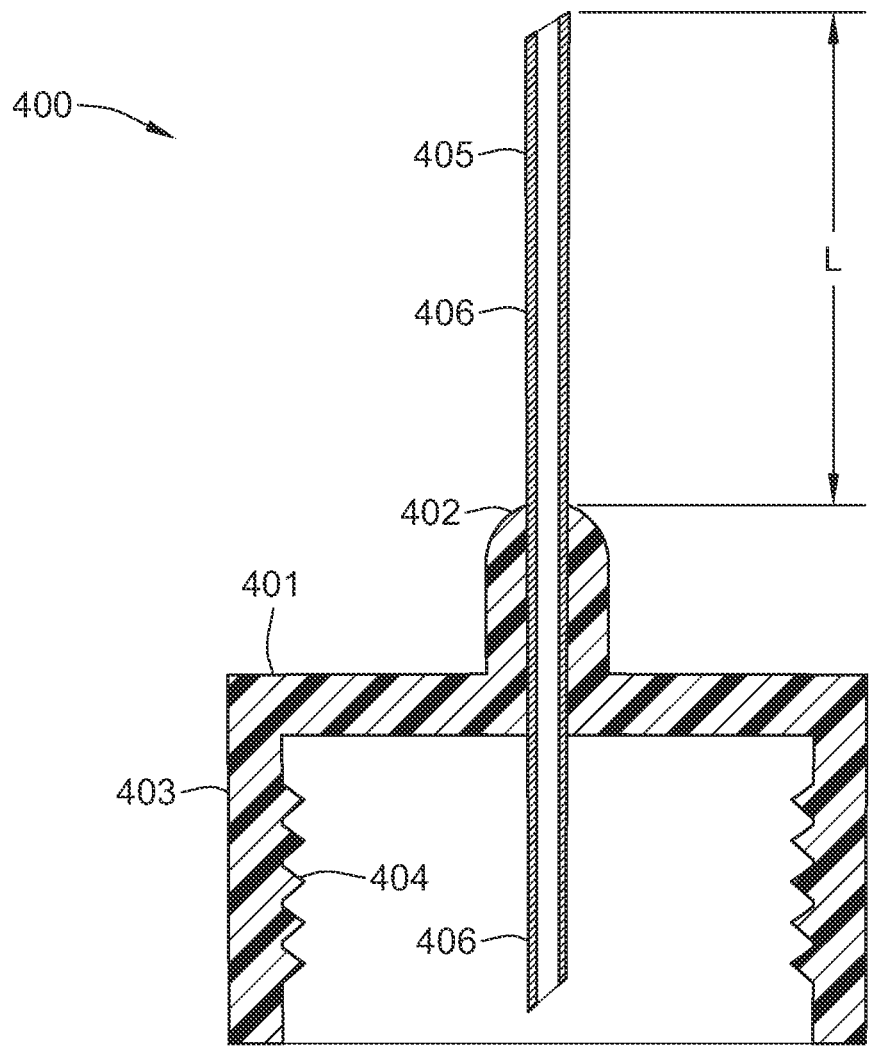
FIG. 13 illustrates one arrangement of the dose dispenser that may be mounted on a distal end of the delivery device.
Figure 14:
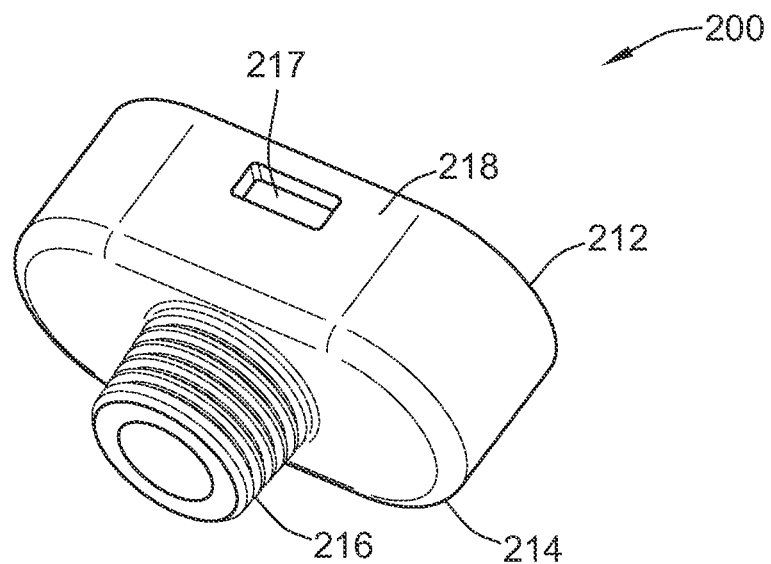
FIG. 14 illustrates a perspective view of the dispense interface illustrated in FIG. 11.
Figure 15:
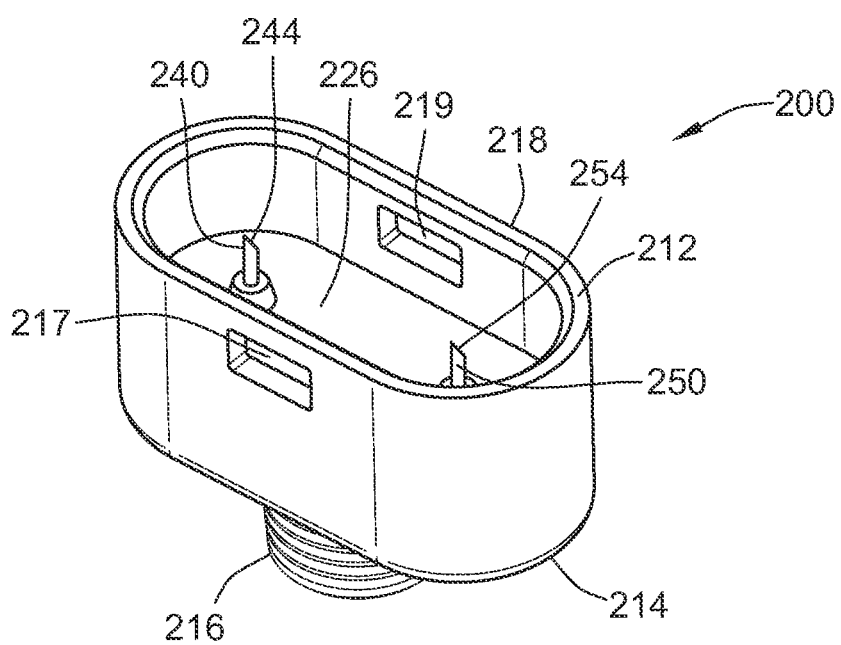
FIG. 15 illustrates another perspective view of the dispense interface illustrated in FIG. 11.

FIG. 12 also illustrates the needle assembly 400 and protective cover 420 coupled to the distal end of the dispense interface 200 that may be screwed onto the needle hub of the interface 200. FIG. 13 illustrates a cross sectional view of the double ended needle assembly 402 mounted on the dispense interface 200 in FIG. 12.

The needle assembly 400 illustrated in FIG. 13 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 11 and 12 provides a form fit around the outer surface 403 of the hub 401.

The needle assembly of FIG. 11 may be removably coupled to the distal end of the dispense interface 200. Referring now to FIGS. 11-12 and 14-19, one preferred arrangement of this interface 200 will now be discussed. In this one preferred arrangement, this interface 200 comprises:

a. a main outer body 210,
    b. an first inner body 220,
    c. a second inner body 230,
    d. a first piercing needle 240,
    e. a second piercing needle 250,
    f. a valve seal 260, and
    g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 15, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 11 and 12. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 13. Alternative releasable connectors may also be provided such as a snap lock, a snap lock released through threads, a bayonet lock, a form fit, or other similar connection arrangements.

Figure 16:
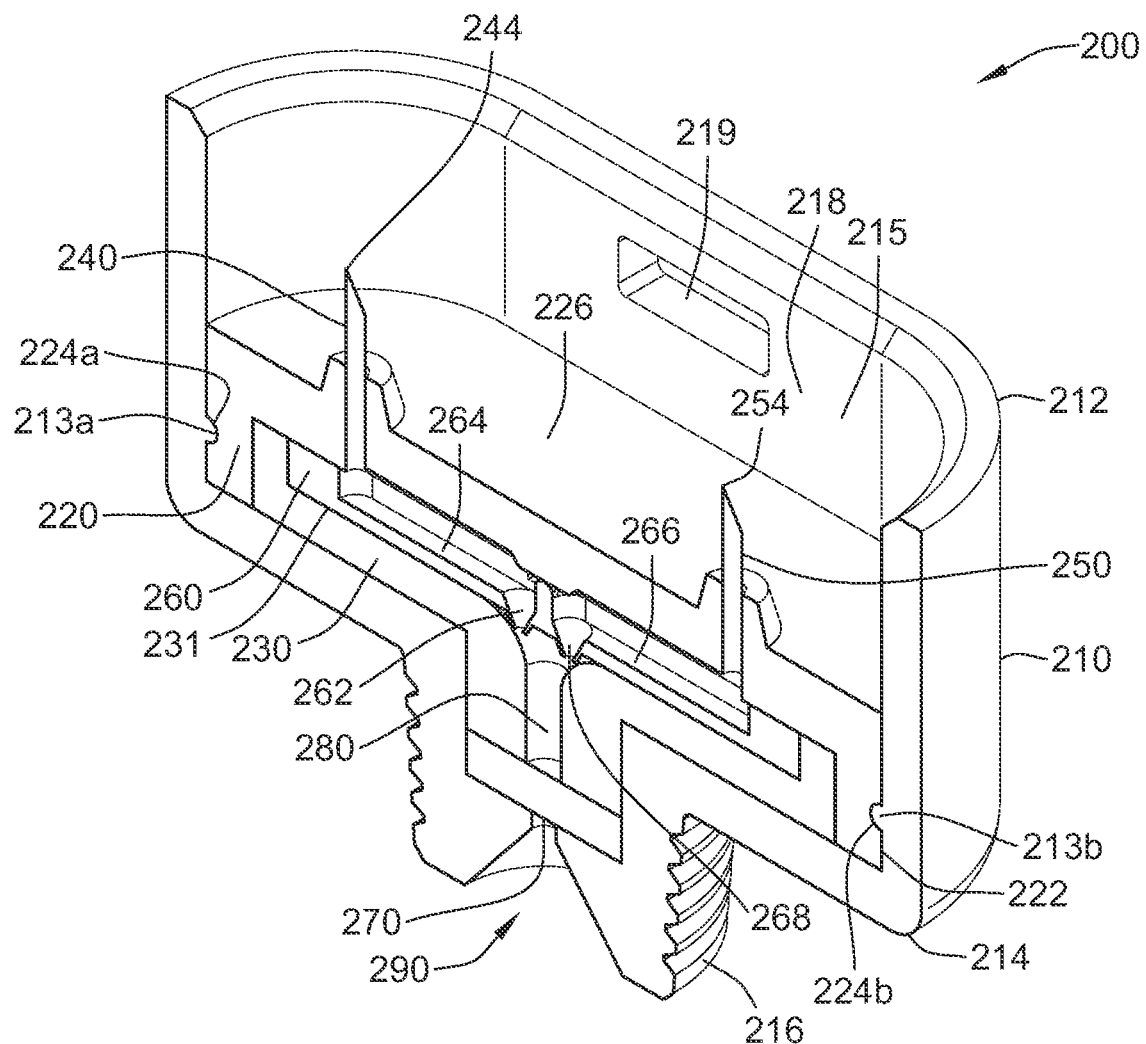
FIG. 16 illustrates a cross-sectional view of the dispense interface illustrated in FIGS. 11 and 12.
Figure 17:
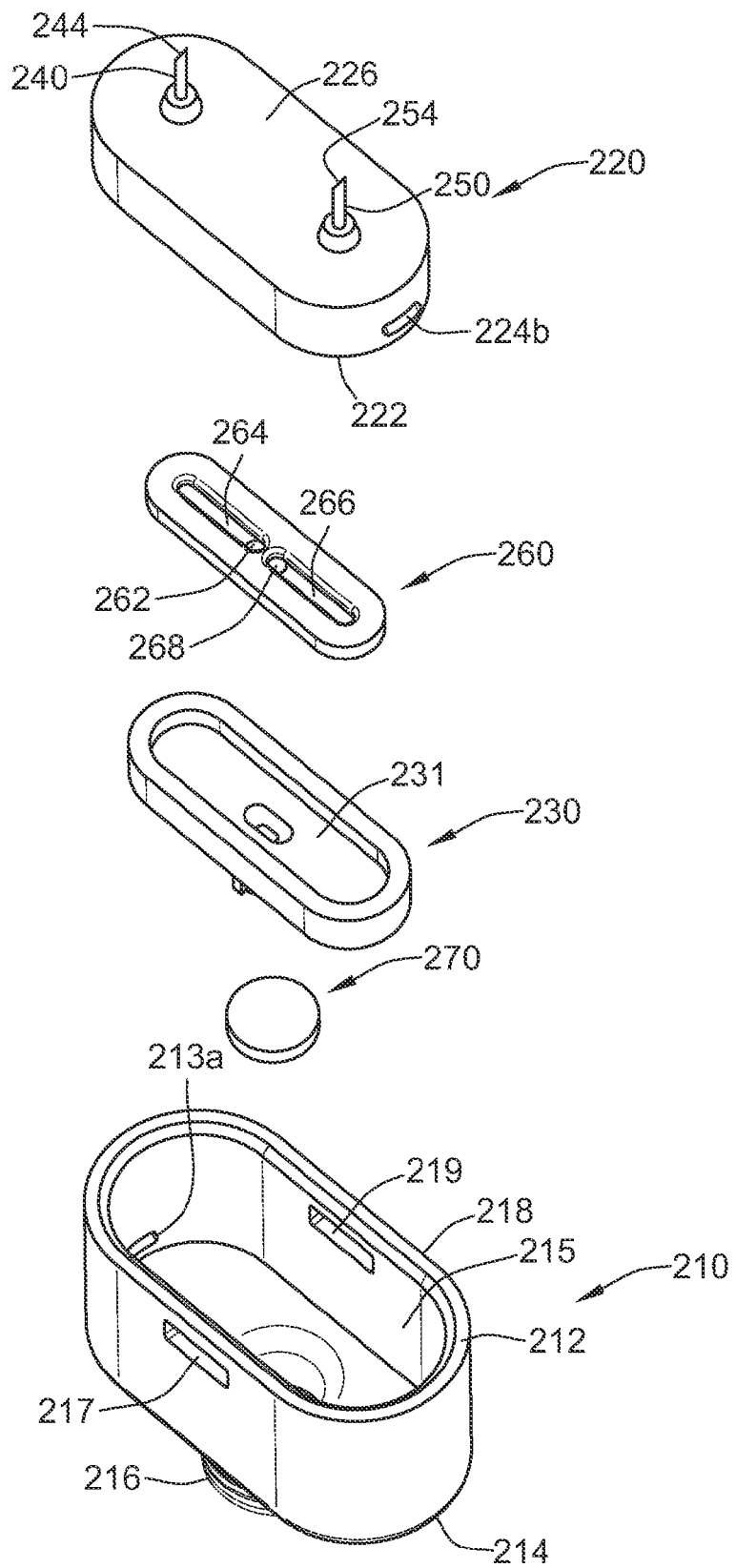
FIG. 17 illustrates an exploded view of the dispense interface illustrated in FIG. 11.
Figure 18:
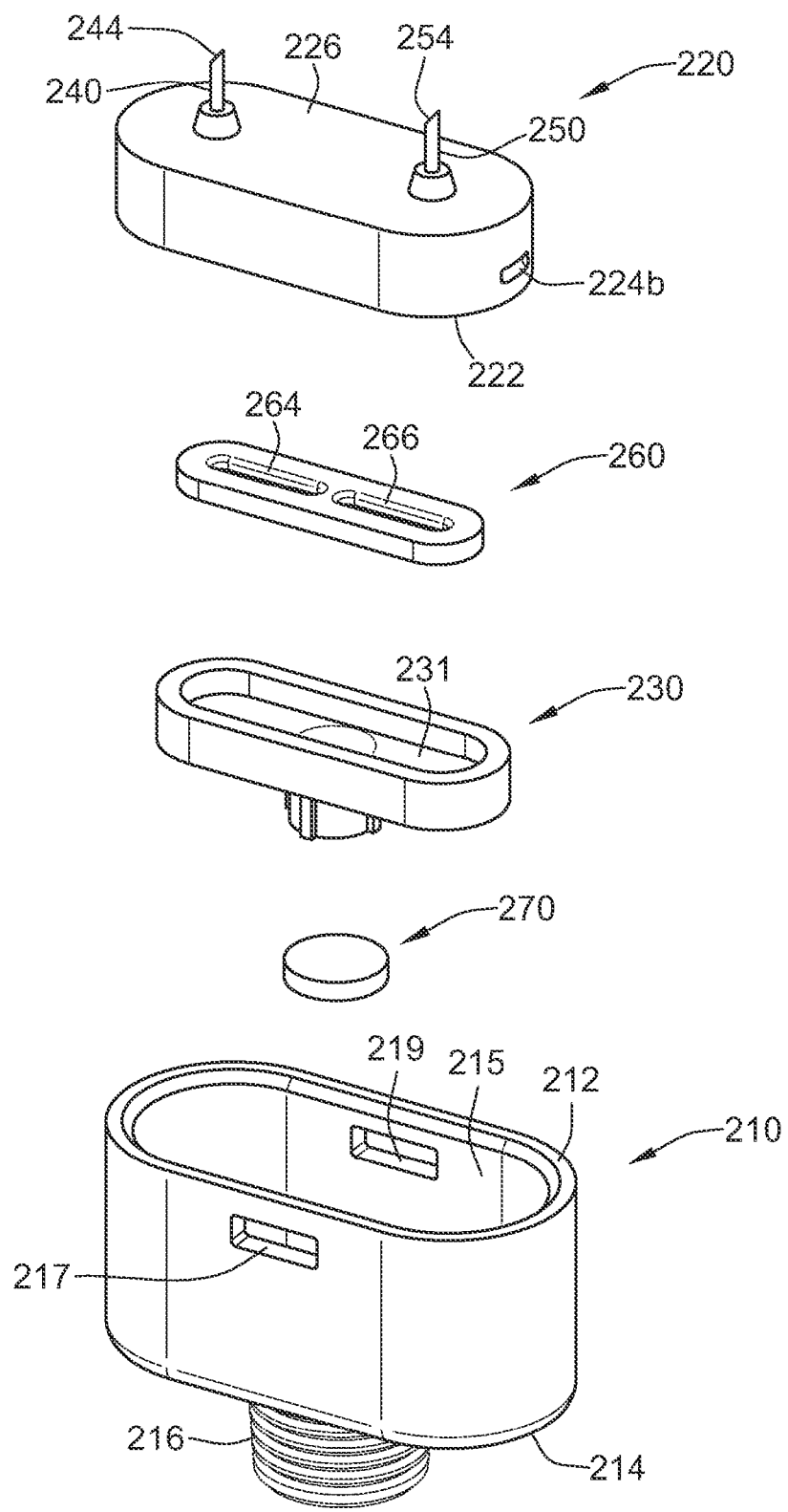
FIG. 18 illustrates another exploded view of the dispense interface illustrated in FIG. 11.

The dispense interface 200 further comprises a first inner body 220. Certain details of this inner body are illustrated in FIGS. 15-19. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 16, the extending wall 218 of the main outer body 210 is provided with a first rib 213*a* and a second rib 213*b*. This first rib 213*a* is also illustrated in FIG. 17. These ribs 213*a* and 213*b* are positioned along the inner surface 215 of the wall 218 of the outer body 210 and create a form fit or snap lock engagement with cooperating grooves 224*a* and 224*b* of the first inner body 220. In a preferred arrangement, these cooperating grooves 224*a* and 224*b* are provided along an outer surface 222 of the first inner body 220.

In addition, as can be seen in FIGS. 15-18, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 16 illustrates the position of the valve seal 260, seated between the first inner body 220 and the second inner body 230. During an injection step, this seal valve 260 helps to prevent the primary medicament in the first pathway from migrating to the secondary medicament in the second pathway while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 13), the output fluid path allows both medicaments to be in fluid communication with the attached needle assembly.

The hub interface 200 further comprises a second inner body 230. As can be seen from FIG. 16, this second inner body 230 has an upper surface that defines a recess, and the valve seal 260 is positioned within this recess. Therefore, when the interface 200 is assembled as shown in FIG. 16, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Although not shown, the dispense interface 200 could be supplied by a manufacturer as being contained in a protective and sterile capsule or container. As such, where the user would peel or tear open a seal or the container itself to gain access to the sterile single dispense interface. In some instances it might be desirable to provide two or more seals for each end of the interface. The seal may allow display of information required by regulatory labeling requirements. When a double ended needle assembly is used as a single dispense assembly to deliver the single dose of both medicaments, it is preferred that the interface is designed to be economical and safe for allowing the user to attach a new hub for each injection.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 19:
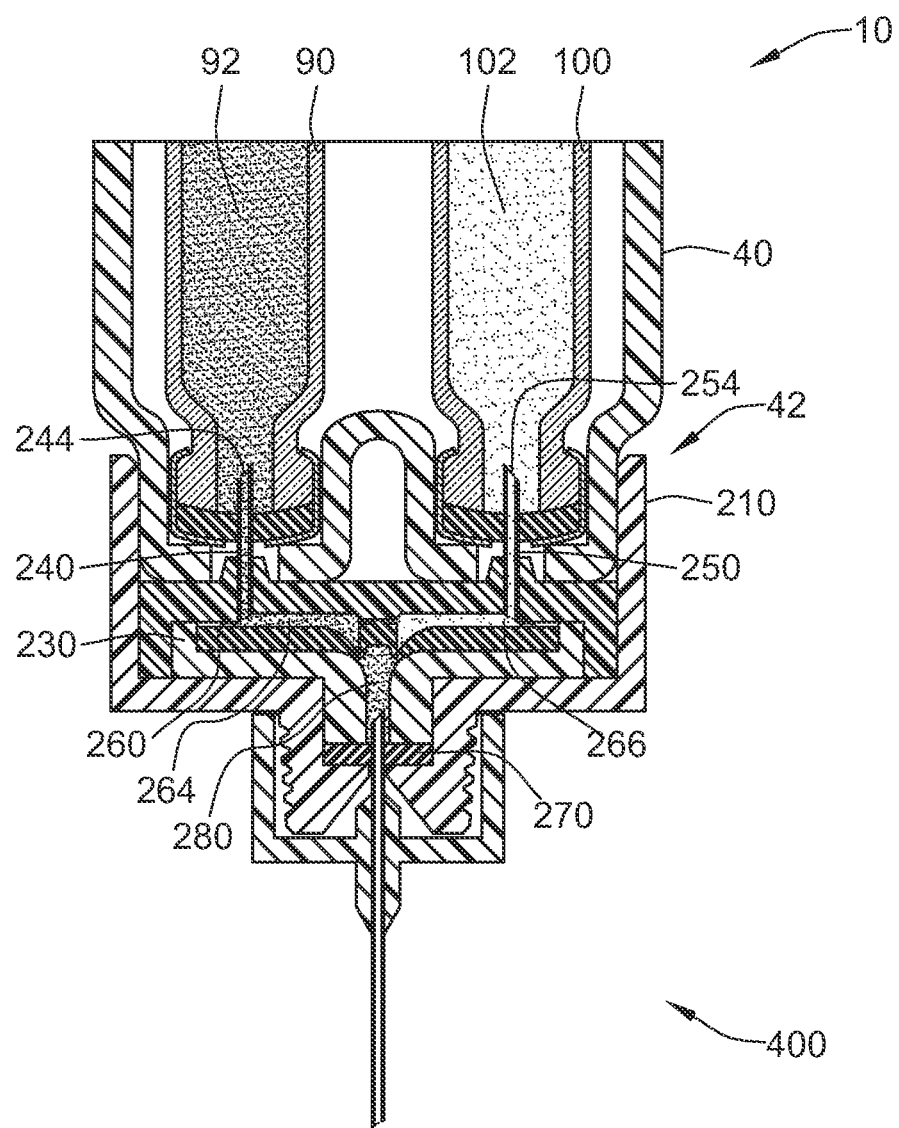
FIG. 19 illustrates a cross-sectional view of the dispense interface and dose dispenser mounted onto a drug delivery device, such as the device illustrated in FIGS. 1a and 1b.

FIG. 19 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 19 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 19, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 19, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

In one arrangement, the drug delivery device 10 comprises a detection sensor so as to sense or confirm that the dispense interface 200 has been correctly mounted onto the cartridge housing 40. Such a detection sensor may comprise either a mechanical, an electrical, a capacitive, an inductive or other similar type sensor. As illustrated, this sensor may be provided near the distal end of the cartridge housing.

In addition, the drug delivery device may comprise a similar detection sensor for detecting the presence of the dose dispenser. For example, such a sensor may be provided adjacent the needle hub of the interface 200. Preferably, either or both of the detection sensors would be communicatively coupled to the micro-processor. Optionally, the micro-processor would be programmed so as prevent a user from setting a dose with the drug delivery device 10 unless the device has detected that both the dispense interface 200 has been properly mounted to the cartridge holder 40 and that a dose dispenser has been properly mounted onto the interface. If either the dispense interface or the dose dispenser has been detected as being incorrectly mounted, the user may be locked out of the device and a connection error may be shown on the digital display 80.

Additionally, the dispense interface 200 could incorporate a safety shield device that would prevent accidental needle sticks and reduce the anxiety experienced by users who suffer from needle phobia. The exact design of the safety shield is not critical to the presently described drug delivery device and system. However, a preferred design is one that is operably connected to drug delivery device 10. In such a design, the activation of the safety shield could unlock the drug delivery system or enable medicament to be dispensed via the dispense interface and dose dispenser. Another preferred design would physically prevent insertion of the used drug dispense interface into the patient (e.g., a single use needle-guard type arrangement). Preferably, the interface is configured to work with a conventional double ended needle assembly. Alternatively, the interface may be configured to work with a non-conventional needle assembly. One example of such a non-conventional-needle assembly may comprise a coded needle assembly.

In one preferred electro-mechanical drug delivery device, a single dispense assembly comprising a catheter may be coupled to the interface 200.

In one preferred arrangement, the dispense interface 200 is a disposable interface and as such, the needle hub comprises a disposable element that is discarded when either the first or the second cartridge in the device is replaced (e.g., when such cartridge is empty). In one arrangement, the dispense interface 200 may be provided in a drug delivery kit. For example, in one drug delivery kit arrangement, a needle assembly interface can be provided with each replacement cartridge. In an alternative kit arrangement, a plurality of double ended needle assemblies are provided with a multi-use dispense interface.

Figure 20:
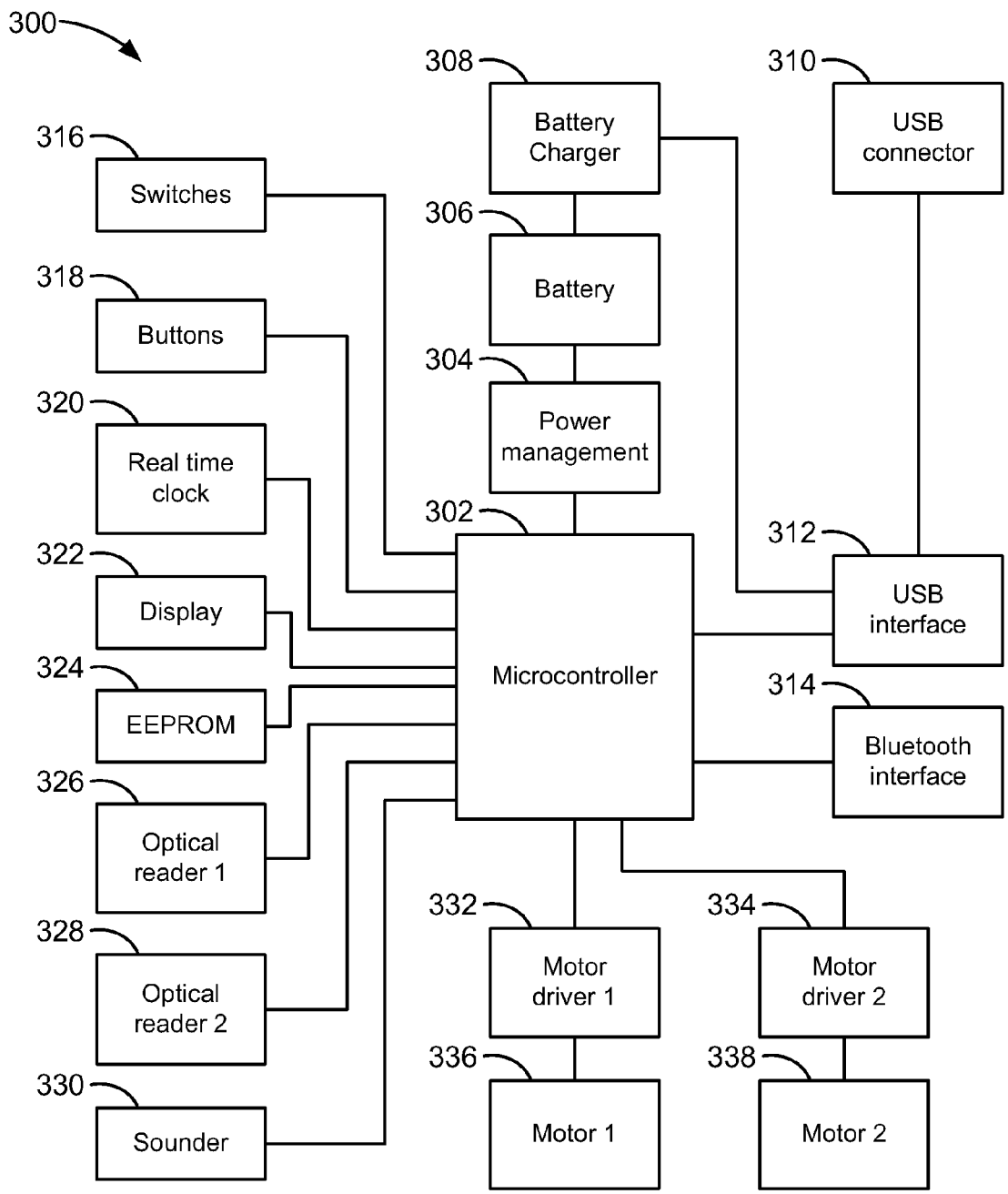
FIG. 20 illustrates a block diagram functional description of a control unit for operation of the drug delivery device illustrated in FIG. 11.
Figure 21:
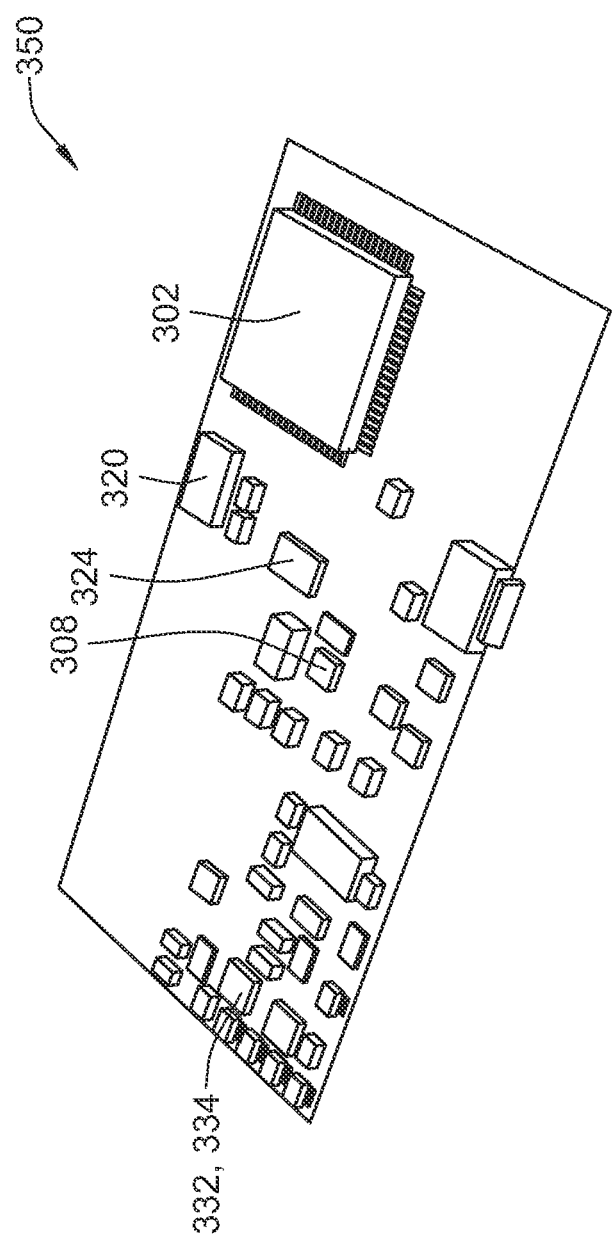
FIG. 21 illustrates a printed circuit board assembly of the drug delivery device illustrated in FIG. 11.

FIG. 20 illustrates a functional block diagram of a control unit to operate and control the drug delivery device illustrated in FIG. 1. FIG. 21 illustrates one arrangement of a printed circuit board (PCB) or printed circuit board assembly (PCBA) 350 that may comprise certain portions of the control unit illustrated in FIG. 20.

Referring now to both FIGS. 20 and 21, it may be seen that the control unit 300 comprises a microcontroller 302. Such a microcontroller may comprise a Freescale MCF51JM microcontroller. The microcontroller is used to control the electronic system for the drug delivery device 10. It includes internal analogue to digital converters and general purpose digital I/O lines. It can output digital Pulse Width Modulated (PWM) signals. It includes an internal USB module. In one arrangement, a USB protection circuit such as ON-Semi NUP3115 may be implemented. In such an implementation, the actual USB communications may be provided on board the microcontroller 302.

The control unit further comprises a power management module 304 coupled to the microcontroller 302 and other circuit elements. The power management module 304 receives a supply voltage from a main power source such as the battery 306 and regulates this supply voltage to a plurality of voltages required by other circuit components of the control unit 300. In one preferred control unit arrangement, switched mode regulation (by means of a National Semiconductor LM2731) is used to step up the battery voltage to 5V, with subsequent linear regulation to generate other supply voltages required by the control unit 300.

The battery 306 provides power to the control unit 300 and is preferably supplied by a single lithium-ion or lithium-polymer cell. This cell may be encapsulated in a battery pack that contains safety circuitry to protect against overheating, overcharging and excessive discharge. The battery pack may also optionally contain coulomb counting technology to obtain an improved estimate of remaining battery charge.

A battery charger 308 may be coupled to the battery 306. One such battery charger may be based on Texas Instruments (TI) BQ24150 along with other supporting software and hardware modules. In one preferred arrangement, the battery charger 308 takes energy from the external wired connection to the drug delivery device 10 and uses it to charge the battery 306. The battery charger 308 can also be used to monitor the battery voltage and charge current to control battery charging. The battery charger 308 can also be configured to have bidirectional communications with the microcontroller 302 over a serial bus. The charge status of the battery 306 may be communicated to the microcontroller 302 as well. The charge current of the battery charger may also be set by the microcontroller 302.

The control unit may also comprise a USB connector 310. A micro USB-AB connector may be used for wired communications and to supply power to the device.

The control unit may also comprise a USB interface 312. This interface 312 may be external to the microcontroller 302. The USB interface 312 may have USB master and/or USB device capability. The USB interface 312 may also provide USB on-the-go functionality. The USB interface 312 external to the microcontroller also provides transient voltage suppression on the data lines and VBUS line.

An external Bluetooth interface 314 may also be provided. The Bluetooth interface 314 is preferably external to the microcontroller 302 and communicates with this controller 302 using a data interface.

Preferably, the control unit further comprises a plurality of switches 316. In the illustrated arrangement, the control unit 300 may comprise eight switches 316 and these switches may be distributed around the device. These switches 316 may be used to detect and or confirm at least the following:

h. Whether the dispense interface 200 has been properly attached to the drug delivery device 10;
i. Whether the removable cap 18 has been properly attached to the main body 20 of the drug delivery device 10;
j. Whether the first cartridge retainer 50 of the cartridge holder 40 for the first cartridge 90 has been properly closed;
k. Whether the second cartridge retainer 52 of the cartridge holder 40 for the second cartridge 100 has been properly closed;
l. To detect the presence of the first cartridge 90;
m. To detect the presence of the second cartridge 100;
n. To determine the position of the stopper 94 in the first cartridge 90; and
o. To determine the position of the stopper 104 in the second cartridge 100.

These switches 316 are connected to digital inputs, for example to general purpose digital inputs, on the microcontroller 302. Preferably, these digital inputs may be multiplexed in order to reduce the number of input lines required. Interrupt lines may also be used appropriately on the microcontroller 302 so as to ensure timely response to changes in switch status.

In addition, and as described in greater detail above, the control unit may also be operatively coupled to a plurality of human interface elements or push buttons 318. In one preferred arrangement, the control unit 300 comprises eight push buttons 318 and these are used on the device for user input for the following functions:

p. Dose dial up;
q. Dose dial down;
r. Sound level;
s. Dose;
t. Eject;
u. Prime;
v. Dose set; and
w. OK.

These buttons 318 are connected to digital inputs, for example to general purpose digital inputs, on the microcontroller. Again, these digital inputs may be multiplexed so as to reduce the number of input lines required. Interrupt lines will be used appropriately on the microcontroller to ensure timely response to changes in switch status. In an example embodiment, the function of one or more buttons may be replaced by a touch screen.

In addition, the control unit 300 comprises a real time clock 320. Such a real time clock may comprise an Epson RX4045 SA. The real-time clock 320 may communicate with the microcontroller 302 using a serial peripheral interface or similar.

A digital display module 322 in the device preferably uses LCD or OLED technology and provides a visual signal to the user. The display module incorporates the display itself and a display driver integrated circuit. This circuit communicates with the microcontroller 302 using a serial peripheral interface or parallel bus.

The control unit 300 also comprises a memory device, for example volatile and non-volatile memory. Volatile memory may be random access memory (RAM), for example static RAM or dynamic RAM and/or the like, as working memory of microcontroller 302. Non-volatile memory may be read only memory (ROM), FLASH memory or electrically erasable programmable read-only memory (EEPROM), such as an EEPROM 324. Such an EEPROM may comprise an Atmel AT25640. The EEPROM may be used to store system parameters and history data. This memory device 324 communicates with the processor 302 using a serial peripheral interface bus.

The control unit 300 further comprises a first and a second optical reader 326, 328. Such optical readers may comprise Avago ADNS3550. These optical readers 326, 328 may be optional for the drug delivery device 10 and are, as described above, used to read information from a cartridge when such a cartridge is inserted into either the first or the second cartridge retainers 50, 52. Preferably, a first optical reader is dedicated for the first cartridge and the second optical reader is dedicated for the second cartridge. An integrated circuit designed for use in optical computer mice may be used to illuminate a static 2D barcode on the drug cartridge, positioned using a mechanical feature on the drug cartridge, and read the data it contains. This integrated circuit may communicate with the microcontroller 302 using a serial peripheral interface bus. Such a circuit may be activated and deactivated by the microcontroller 302 e.g., to reduce power consumption when the circuit is not needed, for example by extinguishing the cartridge illumination when data is not being read.

As previously mentioned, a sounder 330 may also be provided in the drug delivery device 10. Such a sounder may comprise a Star Micronics MZT03A. The disclosed proposed sounder may be used to provide an audible signal to the user. The sounder 330 may be driven by a pulse-width modulation (PWM) output from the microcontroller 302. In an alternative configuration, the sounder may play polyphonic tones or jingles and play stored voice commands and prompts to assist the user in operating or retrieving information from the device.

The control unit 300 further comprises a first motor driver 332 and a second motor driver 334. The motor drive circuitry may comprise Freescale MPC17C724 and is controlled by the microcontroller 302. For example, where the motor drive comprises a stepper motor drive, the drive may be controlled using general purpose digital outputs. Alternatively, where the motor drive comprises a brushless DC motor drive, the drive may be controlled using a Pulse Width Modulated (PWM) digital output. These signals control a power stage, which switches current through the motor windings. The power stage requires continuous electrical commutation. This may for example increase device safety, decreasing the probability of erroneous drug delivery.

The power stage may consist of a dual H-bridge per stepper motor, or three half-bridges per brushless DC motor. These may be implemented using either discrete semiconductor parts or monolithic integrated circuits.

The control unit 300 further comprises a first and a second motor 336, 338, respectively. As explained in greater detail below, the first motor 336 may be used to move the stopper 94 in the first cartridge 90. Similarly, the second motor 338 may be used to move the stopper 104 in the second cartridge. The motors can be stepper motors, brushless DC motors, or any other type of electric motor. The type of motor may determine the type of motor drive circuit used. The electronics for the device may be implemented with one main, rigid printed circuit board assembly, potentially with additional smaller flexible sections as required, e.g., for connection to motor windings and switches.

The micro-processor provided on the PCBA 350 will be programmed to provide a number of features and carry out a number of calculations. For example, and perhaps most importantly, the micro-processor will be programmed with an algorithm for using a certain therapeutic dose profile to calculate at least a dose of the secondary medicament based at least in part on the selected dose of the primary medicament.

For such a calculation, the controller may also analyze other variables or dosing characteristics in calculating the amount of second medicament to administer. For example, other considerations could include at least one or more of the following characteristics or factors:

x. Time since last dose;
y. Size of last dose;
z. Size of current dose;
aa. Current blood glucose level;
bb. Blood glucose history;
cc. Maximum and/or minimum permissible dose size;
dd. Time of day;
ee. Patient's state of health;
ff. Exercise taken; and
gg. Food intake.

These parameters may also be used to calculate the size of both the first and the second dose size.

In one arrangement, and as will be described in greater detail below, a plurality of different therapeutic dose profiles may be stored in the memory device or devices operatively coupled to the micro-processor. In an alternative arrangement, only a single therapeutic dose profile is stored in the memory device operatively coupled to the micro-processor.

The presently proposed electromechanical drug delivery device is of particular benefit to patients with dexterity or computational difficulties. With such a programmable device, the single input and associated stored predefined therapeutic profile removes the need for the user or patient to calculate their prescribed dose every time they use the device. In addition, the single input allows easier dose setting and dispensing of the combined compounds.

In addition to computing the dose of the second medicament, the micro-processor can be programmed to achieve a number of other device control operations. For example, the micro-processor may be programmed so as to monitor the device and shut down the various elements of the system to save electrical energy when the device is not in use. In addition, the controller can be programmed to monitor the amount of electrical energy remaining in the battery 306. In one preferred arrangement, an amount of charge remaining in the battery can be indicated on the digital display 80 and a warning may be given to the user when the amount of remaining battery charge reaches a predetermined threshold level. In addition, the device may include a mechanism for determining whether there is sufficient power available in the battery 306 to deliver the next dose, or it will automatically prevent that dose from being dispensed. For example, such a monitoring circuit may check the battery voltage under different load conditions to predict the likelihood of the dose being completed. In a preferred configuration the motor in an energized (but not moving) condition and a not energized condition may be used to determine or estimate the charge of the battery.

Preferably, the drug delivery device 10 is configured to communicate via a data link (i.e., either wirelessly or hard wired) with various computing devices, such as a desktop or laptop computer. For example, the device may comprise a Universal Serial Bus (USB) for communicating with a PC or other devices. Such a data link may provide a number of advantages. For example, such a data link may be used to allow certain dose history information to be interrogated by a user. Such a data link could also be used by a health care professional to modify certain key dose setting parameters such as maximum and minimum doses, a certain therapeutic profile, etc. The device may also comprise a wireless data link, for example an IRDA data link or a Bluetooth data link. A preferred Bluetooth module comprises a Cambridge Silicon Radio (CSR) Blue core 6.

In an example embodiment, the device has USB On-The-Go (USB OTG) capability. USB OTG may allow the drug delivery device 10 to generally fulfill the role of being slave to a USB host (e.g., to a desktop or notebook computer) and to become the host themselves when paired with another slave device (e.g. a BGM).

For example, standard USB uses a master/slave architecture. A USB Host acts as the protocol master, and a USB 'Device' acts as the slave. Only the Host can schedule the configuration and data transfers over the link. The Devices cannot initiate data transfers, they only respond to requests given by a host. Use of OTG in The disclosed drug delivery device 10 introduces the concept that the drug delivery device can switch between the master and slave roles. With USB OTG, the disclosed device 10 at one time be a 'Host' (acting as the link master) and a 'Peripheral' (acting as the link slave) at another time.

Figure 22:
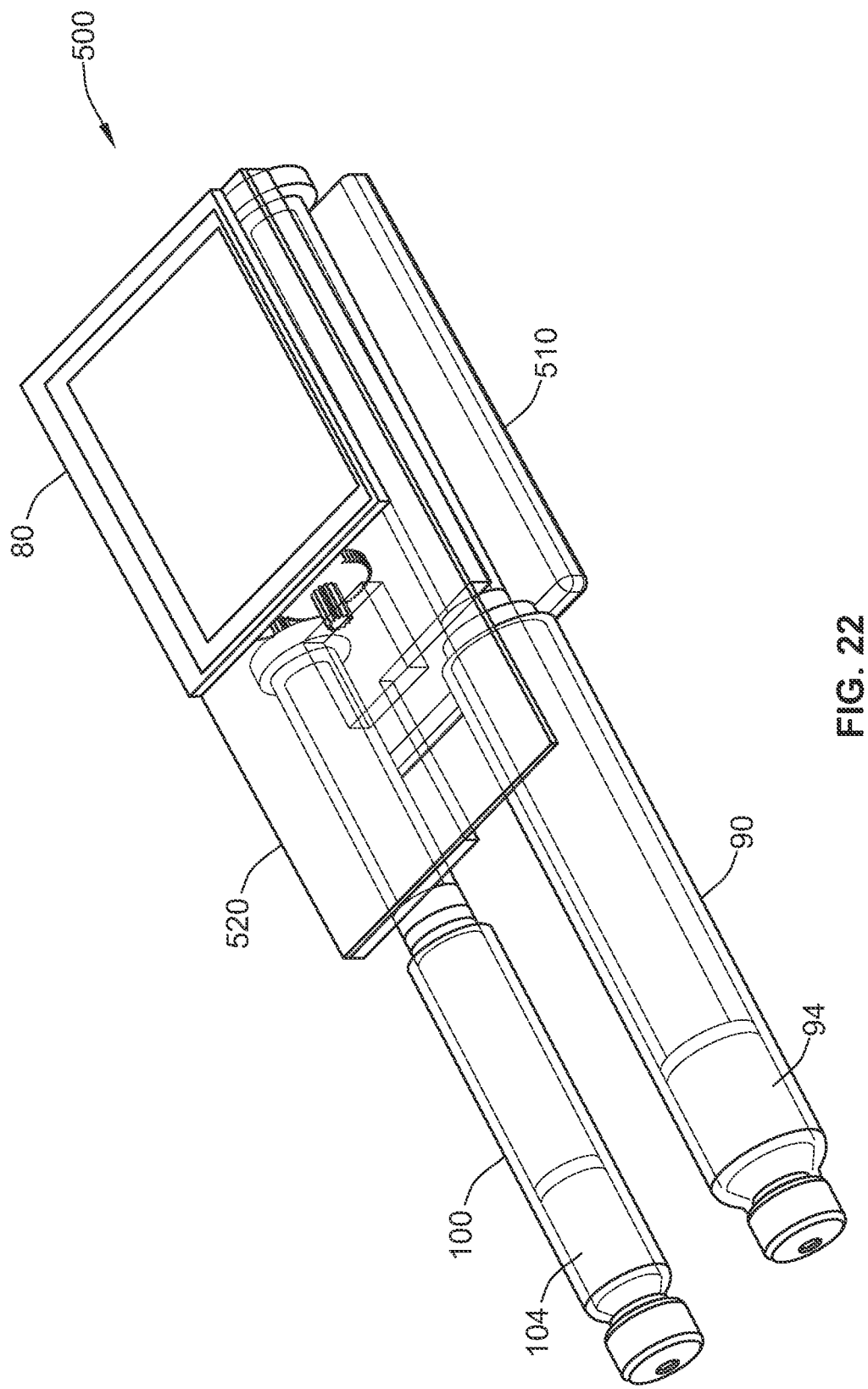
FIG. 22 illustrates a schematic view of a drive mechanism for use with the drug delivery device illustrated in FIGS. 1a and 1b.

FIG. 22 illustrates various internal components of the drug delivery device 10 illustrated in FIGS. 1*a* and 1*b* including one preferred arrangement of a drive train 500. As illustrated, FIG. 22 illustrates the digital display 80, a printed circuit board assembly (PCBA) 520 (such as the PCB 350 illustrated in FIG. 21), along with a power source or battery 510. The PCBA 520 may be positioned between the digital display 80 and a drive train 500 with the battery or power source 510 positioned beneath this drive train. The battery or power source 510 is electronically connected to provide power to the digital display 80, the PCBA 520 and the drive train 500. As illustrated, both the first and second cartridges 90, 100 are shown in an expended state. That is, the first and second cartridges are illustrated in an empty state having a stopper at a most distal position. For example, the first cartridge 90 (which ordinarily contains the first medicament 92) is illustrated as having its stopper 94 in the distal position. The stopper 104 of the second cartridge 100 (ordinarily containing the second medicament 102) is illustrated in a similar position.

With reference to FIG. 22, it may be seen that there is provided a first region defining a suitable location for a power source 510 such as a replaceable battery or batteries. The power source 510 may comprise a rechargeable power source and may be recharged while the power source 510 remains in the device. Alternatively, the power source 510 may be removed from the drug delivery device 10 and recharged externally, for example, by way of a remote battery charger. This power source may comprise a Lithium-Ion or Lithium-polymer power source. In this preferred arrangement, the battery 510 comprises a generally flat and rectangular shaped power source.

Figure 23:
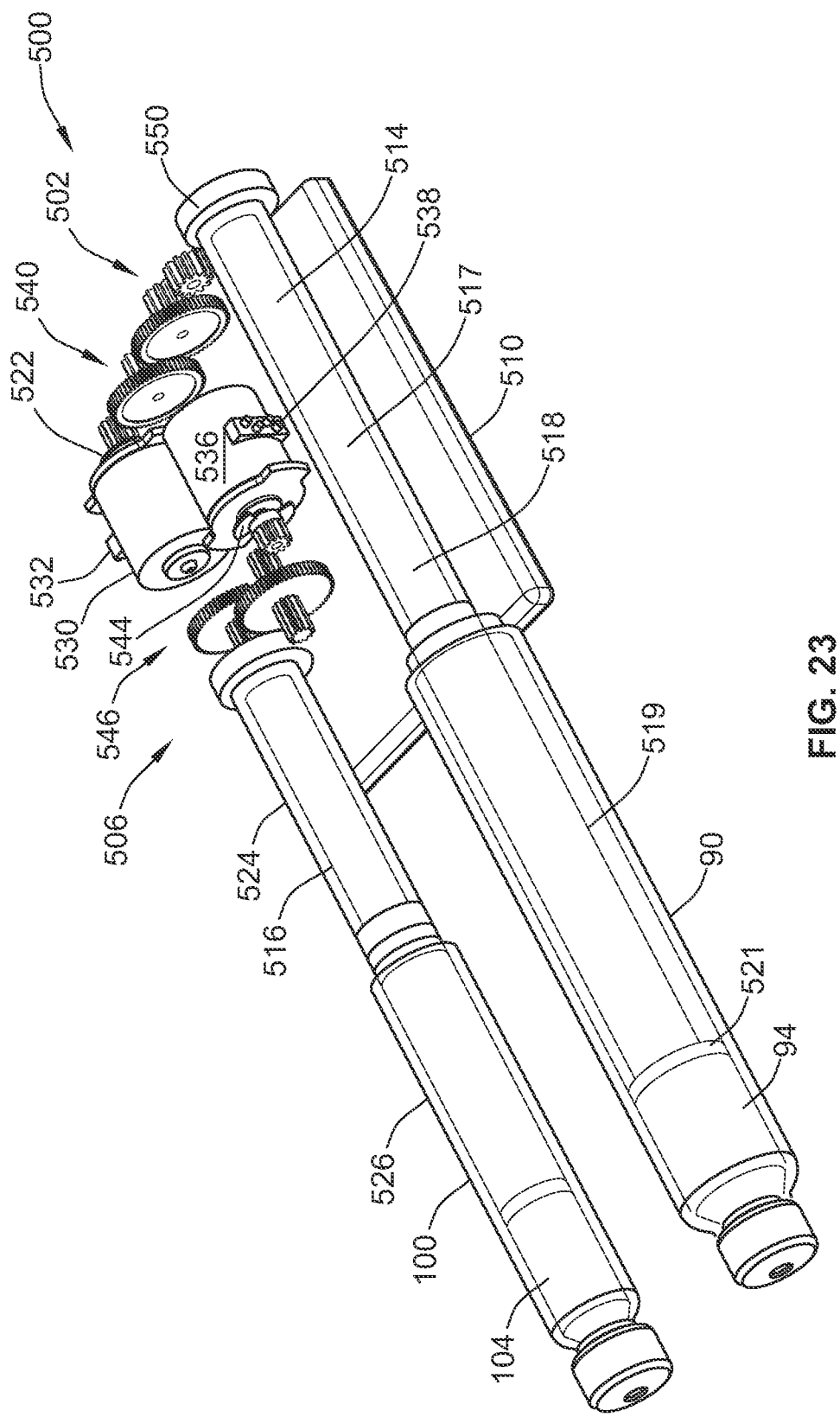
FIG. 23 illustrates another schematic view of the drive mechanism illustrated in FIG. 22.

FIG. 23 illustrates the first arrangement of the electro-mechanical system illustrated in FIG. 22 with both the digital display 80 and the PCBA 520 omitted. As illustrated in FIG. 23, the electro-mechanical system 500 operates to expel a dose from the first cartridge 90 containing the primary medicament 92 and the second cartridge 100 containing the secondary medicament 102. Again, as illustrated in FIG. 23, the first and second cartridges 90, 100 are illustrated in an empty state having stoppers at a most distal position.

In this preferred electro-mechanical system 500, the system comprises an independent mechanical driver for each cartridge 90, 100. That is, an independent mechanical driver 502 operates to expel a dose from the first cartridge 90 and an independent mechanical driver 506 operates to expel a dose from the second cartridge 100. In an alternative electro-mechanical system 500 operating on three different medicaments, three independent mechanical drivers could be provided. The independent mechanical drivers act under control of the motor drivers 332, 334 of the control unit 300 (see, e.g., FIG. 20).

The first independent mechanical driver 502 operates to expel a dose from the first cartridge 90. This first driver 502 comprises a first motor 530 that is operatively coupled to a first gearing arrangement 540. To energize this motor 530, a connector 532 is provided as a means of electrically connecting to the motor driver 332. This first gearing arrangement 540 is mechanically linked to a proximal portion of the first telescoping piston rod 514. The first telescoping piston rod 514 is illustrated in a fully extended position having a distal end 521 acting on the stopper 94 of the first cartridge 90.

As this gearing arrangement 540 is driven by the output shaft of the first motor 530, this arrangement 540 rotates the proximal portion 518 of the first telescoping piston rod 514. As this proximal portion 518 of the piston rod 514 is rotated, the second or distal portion 519 of the piston rod 514 is driven in a distal direction.

Preferably, the proximal portion 518 of the telescope piston rod 514 comprises an external thread 517. This thread 517 engages the distal portion 519 which has in integrated nut comprising a short threaded section at a proximal end of the distal portion 519. This distal portion 519 is prevented from rotating via a key acting in a keyway. Such a keyway may pass through the middle of first telescope 514. Therefore, when the first gearbox arrangement 540 causes rotation of the proximal section 518, rotation of the proximal portion 518 acts upon the distal end 521 to thereby drive the distal portion of telescope piston rod to extend along the longitudinal axis.

Moving in this distal direction, the distal end 521 of the second portion 519 of the piston rod 514 exerts a force on a stopper 94 contained within the first cartridge 90. With this distal end 521 of the piston rod 514 exerting a force on the stopper, the user selected dose of the first medicament 92 is forced out of the cartridge 90 and into an attached dispense interface 200 and consequently out an attached needle assembly 400 as previously discussed above.

A similar injection operation occurs with the second independent driver 506 when the controller first determines that a dose of the second medicament 102 is called for and determines the amount of this dose. As previously mentioned, in certain circumstances, the controller may determine that a dose of the second medicament 102 may not be called for and therefore this second dose would be "set" to a "0" dose.

Preferably, motors 530, 536 comprise motors suitable for electronic commutation. Most preferably, such motors may comprise either a stepper motor or a brushless DC motor.

To inject a dose of the primary and secondary medicaments 92, 102, a user will first select a dose of the primary medicament by way of the human interface components on the display 80. (see, e.g., FIGS. 1 and 4). After a dose of the drug from the primary medicament 92 has been selected, the microcontroller will utilize a previously stored algorithm for determining the dose size of a second drug 102 from a second medicament cartridge. This pre-defined algorithm may help to determine at least in part the dose of the second medicament 102 based on a pre-selected therapeutic profile. In one arrangement, these therapeutic profiles are user selectable. Alternatively, these therapeutic profiles may be password protected and selectable only by a person authorized with the password, such a physician or patient care giver. In yet another arrangement, the therapeutic profile may only be set by the manufacture or the supplier of the drug delivery device 10. As such, the drug delivery device 10 may be provided with only one profile.

When the dose sizes of the first and second medicaments have been established, the user can press the injection button 74 (see e.g., FIG. 4). By pressing this button 74, the motor drivers 332, 334 energize both the first and the second motors 530, 536 to begin the injection process described above.

The piston rods 514, 516 are preferably movable between a first fully withdrawn position (not shown) and a second fully extended portion (as shown in FIGS. 22 and 23). With the piston rods 514, 516 in the withdrawn position, the user will be allowed to open up the respective cartridge retainer and remove an empty cartridge. In one preferred arrangement, an end stop switch may be provided in the main body 14 of the drug delivery device 10 so as to detect when either or both of the piston rods 514, 516 are in a fully withdrawn position. Tripping of the end stop switch may release a catch or other fastening device so as to allow access to the main body for replacement of either cartridge 90, 100.

In one preferred arrangement, both the first and second motors 530, 536 operate simultaneously so as to dispense the user selected dose of the first medicament 92 and the subsequently calculated dose of the second medicament 102 simultaneously. That is, both the first and the second independent mechanical drivers 502, 506 are capable of driving the respective piston rods 514, 516 either at the same or a different time. In this manner, now referring to the dispense interface 200 previously discussed, the first medicament 92 enters the holding chamber 280 of the dispense interface 200 at essentially the same time as the second medicament. One advantage of such an injecting step is that a certain degree of mixing can occur between the first and second medicament 92, 102 prior to actual dose administration.

If after an injection, the patient determines that one or more of the cartridges 90,100 is spent and therefore needs to be exchanged, the patient can follow the following method of cartridge exchange:

hh. Remove the double ended needle from the dispense interface 200;
ii. Remove the dispense interface 200 from the cartridge holder 40 of the device 10;
jj. Enable a menu option on the digital display 80 to change the first cartridge 90 and/or the second cartridge 100;
kk. Rewind the first and/or the second piston rods 514, 516;
ll. The first and/or second cartridge retainer doors will pop open;
mm. The user removes the spent cartridge and replaces this spent cartridge with a new cartridge;
nn. The reservoir doors may manually be closed;
oo. Once the doors are closed, the first and second piston rods 514, 516 advance so that a most distal portion of each rod will meet the stopper of the respective cartridge and will stop advancing when a bung detect mechanism coupled to the micro-processor is activated;
pp. The user replaces the dispense interface 200 in the one way manner on the cartridge holder 40;
qq. The user can, optionally, connect a new double ended needle to the dispense interface 200;

rr. The user can, optionally, perform a test shot or a priming step with the device 10; and ss. The user can then set the next dose for a subsequent dose administration step.

One or more of the steps may be performed automatically, for example controlled by microcontroller 302, such as the step of rewinding the first and/or second piston rod.

In an alternative arrangement, the controller may be programmed so that the first and the second independent mechanical drivers 502, 506 may be operated to dispense either the first medicament 92 or the second medicament 102 prior to the other medicament. Thereafter, the second or the primary medicament may then be dispensed. In one preferred arrangement, the secondary medicament 102 is dispensed before the primary medicament 92.

Preferably, the first and second motors 530, 536 comprise electronic commutation. Such commutation may help to minimise the risk of a motor runaway condition. Such a motor runaway condition could occur with a system comprising a standard brushed motor experiencing a fault. In one embodiment of the motor drive system, a watchdog system may be provided. Such a system has the ability to remove power to either or both of the motors in the event of a software malfunction or a failure of the electronic hardware. To prevent the power from being removed, the correct input from a number of sections of the electronic hardware and/or the microcontroller software will need to be provided. In one of these input parameters is incorrect; power may be removed from the motor.

In addition, preferably both motors 530, 536 may be operated in a reverse direction. This feature may be required in order to allow the piston rods 514, 516 to be moved between a first and a second position.

Figures 24A, 24B:
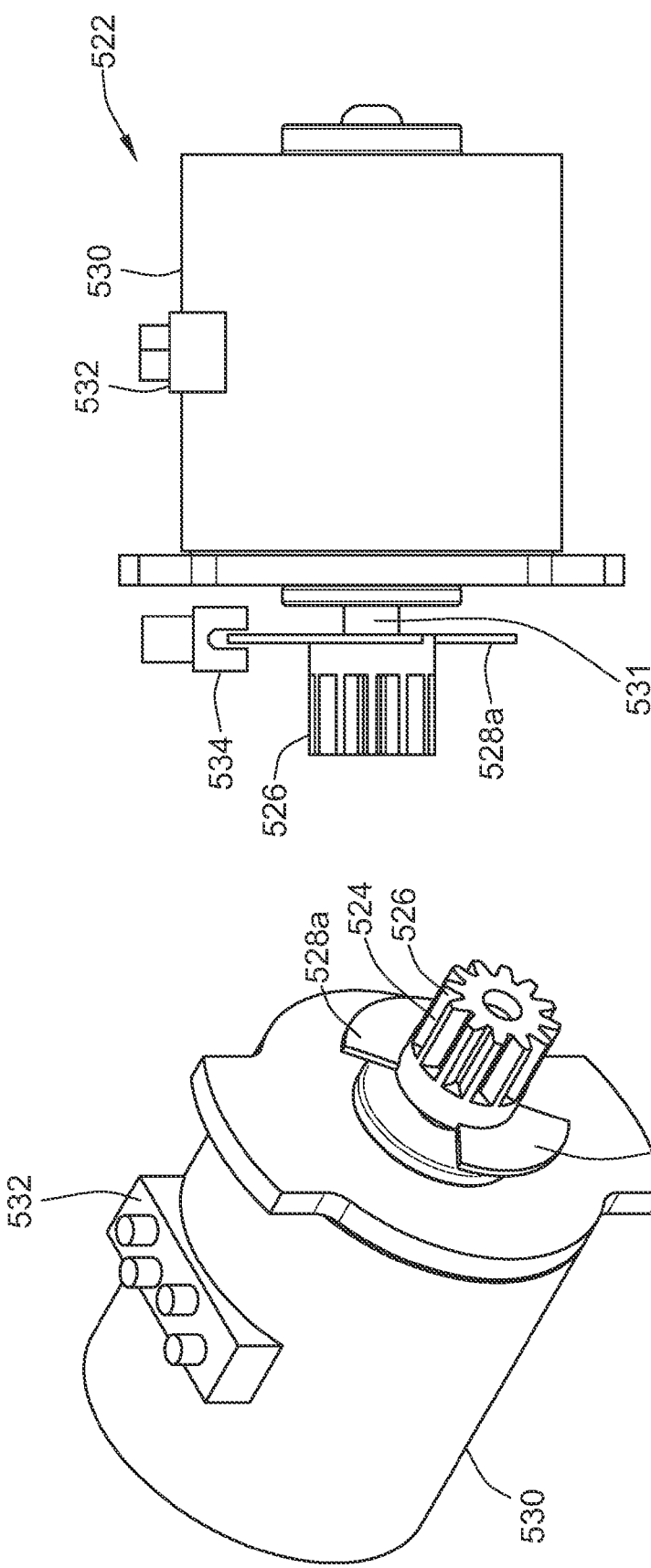
FIGS. 24a and 24b illustrate a motion detection system that may be used with the drive mechanism illustrated in FIG. 22.

Preferably, the first independent drive train 502 illustrated in FIG. 23 comprises a first motion detection system 522. FIG. 24a illustrates a perspective view of the first motor 530 illustrated in FIG. 23. FIG. 24b illustrates a preferred motion detection system 522 comprising the first motor 530 illustrated in FIG. 24a in conjunction with a digital encoder 534.

As illustrated in FIGS. 24a and 24b, such a motion detection system 522 may be beneficial as it can be utilized to provide operational and positional feedback from the first independent driver 502 to the control unit of the drug delivery device 10. For example, with respect to the first independent driver 502, a preferred motion detection system 522 may be achieved through the use of a first motor pinion 524. This first pinion 524 operatively coupled to an output shaft 531 of the first motor 530. The first pinion 524 comprises a rotating gearing portion 526 that drives a first gear of the first gearing arrangement 540 (see, e.g., FIG. 23). The first motor pinion 524 also comprises a plurality of flags 528 *a-b*. In this first motion detection system arrangement 522, the first pinion 524 comprises a first flag 528a and a second flag 528b. These two flags 528*a-b* are positioned on the motor pinion 524 so that they pass through a first optical encoder 534 as the motor output shaft 531 and hence the connected first pinion 524 rotate when the motor is driven.

Preferably, as the first and second flags 528*a-b* pass through the first optical encoder 534, the encoder 534 can send certain electrical pulses to the microcontroller. Preferably, the optical encoder 534 sends two electrical pulses per motor output shaft revolution to the microcontroller. As such, the microcontroller can therefore monitor motor output shaft rotation. This may be advantageous to detect position errors or events that could occur during a dose administration step such as jamming of the drive train, incorrect mounting of a dispense interface or needle assembly, or where there is a blocked needle.

Preferably, the first pinion 524 comprises a plastic injection molded pinion. Such a plastic injection molded part may be attached to the output motor shaft 531. The optical encoder 534 may be located and attached to a gearbox housing. Such a housing may contain both the first gearing arrangement 540 along with the optical encoder 534. The encoder 534 is preferably in electrical communication with the control unit potentially via a flexible portion of the PCB. In a preferred arrangement, the second independent drive train 506 illustrated in FIGS. 22 and 23 comprises a second motion detection system 544 that operates in a similar fashion as the first motion detection system 522 of the first drive train 502.

Figure 25:
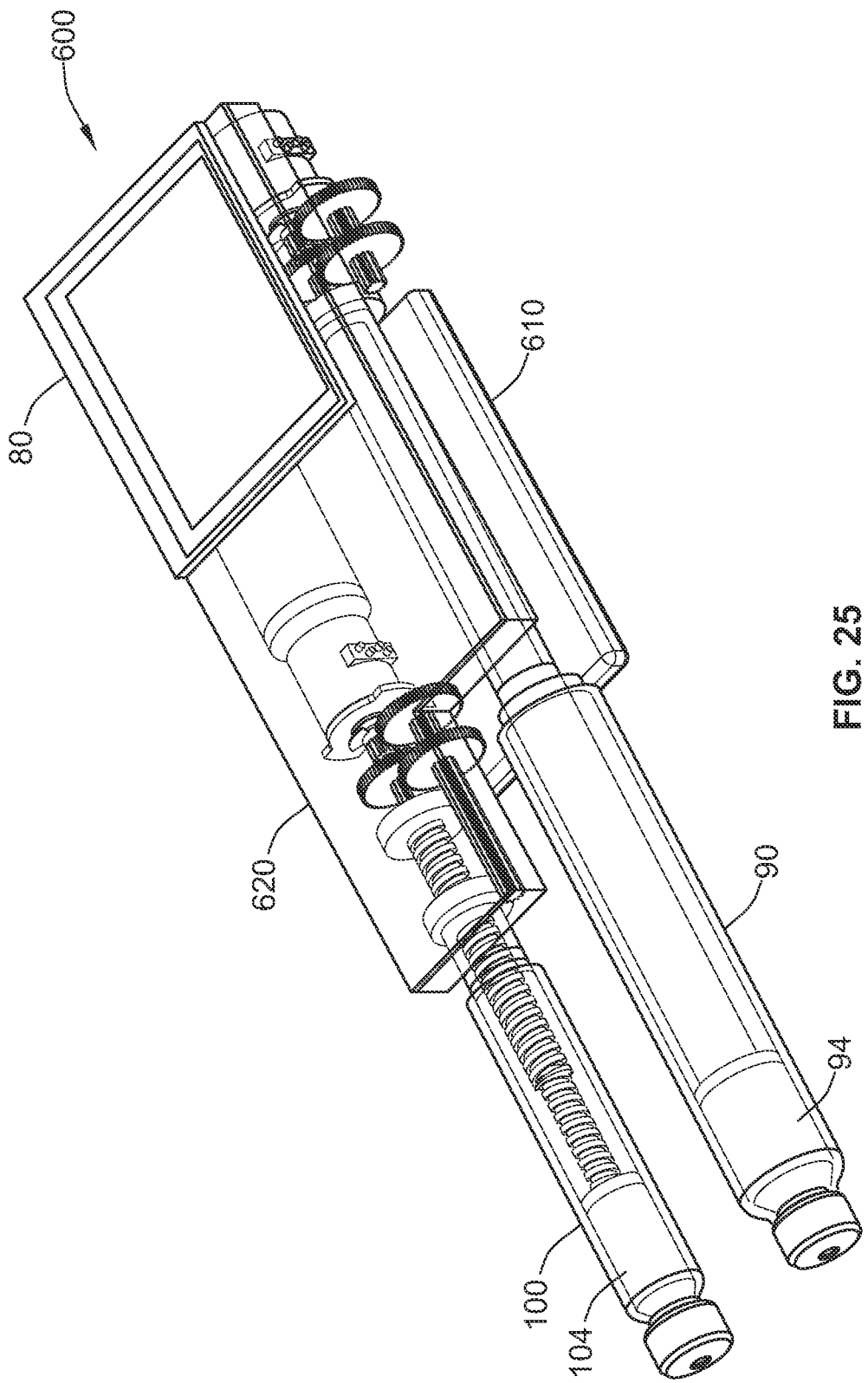
FIG. 25 illustrates a schematic view of an alternative drive mechanism for use with the drug delivery device illustrated in FIGS. 1a and 1b.

FIG. 25 illustrates various internal components of the drug delivery device 10 illustrated in FIGS. 1a and 1b including a preferred alternative drive train arrangement 600. As illustrated, FIG. 25 illustrates the digital display 80, a printed circuit board assembly (PCBA) 620, along with a power source or battery 610. The PCBA 620 may be positioned between the digital display 80 and a drive train 600 with the battery or power source 610 positioned beneath this drive train. The battery or power source 610 is electronically connected to provide power to the digital display 80, the PCBA 620 and the drive train 600. The digital display 80 and the PCBA 620 of this alternative drive train arrangement 600 operate in a similar manner as previously described.

As illustrated, both the first and second cartridges 90, 100 are shown in an expended state. That is, the first and second cartridges are illustrated in an empty state having a stopper at a most distal position. For example, the first cartridge 90 (which ordinarily contains the first medicament 92) is illustrated as having its stopper 94 at the end or most distal position. The stopper 104 of the second cartridge 100 (ordinarily containing the second medicament) is illustrated in a similar end position.

Figure 26:
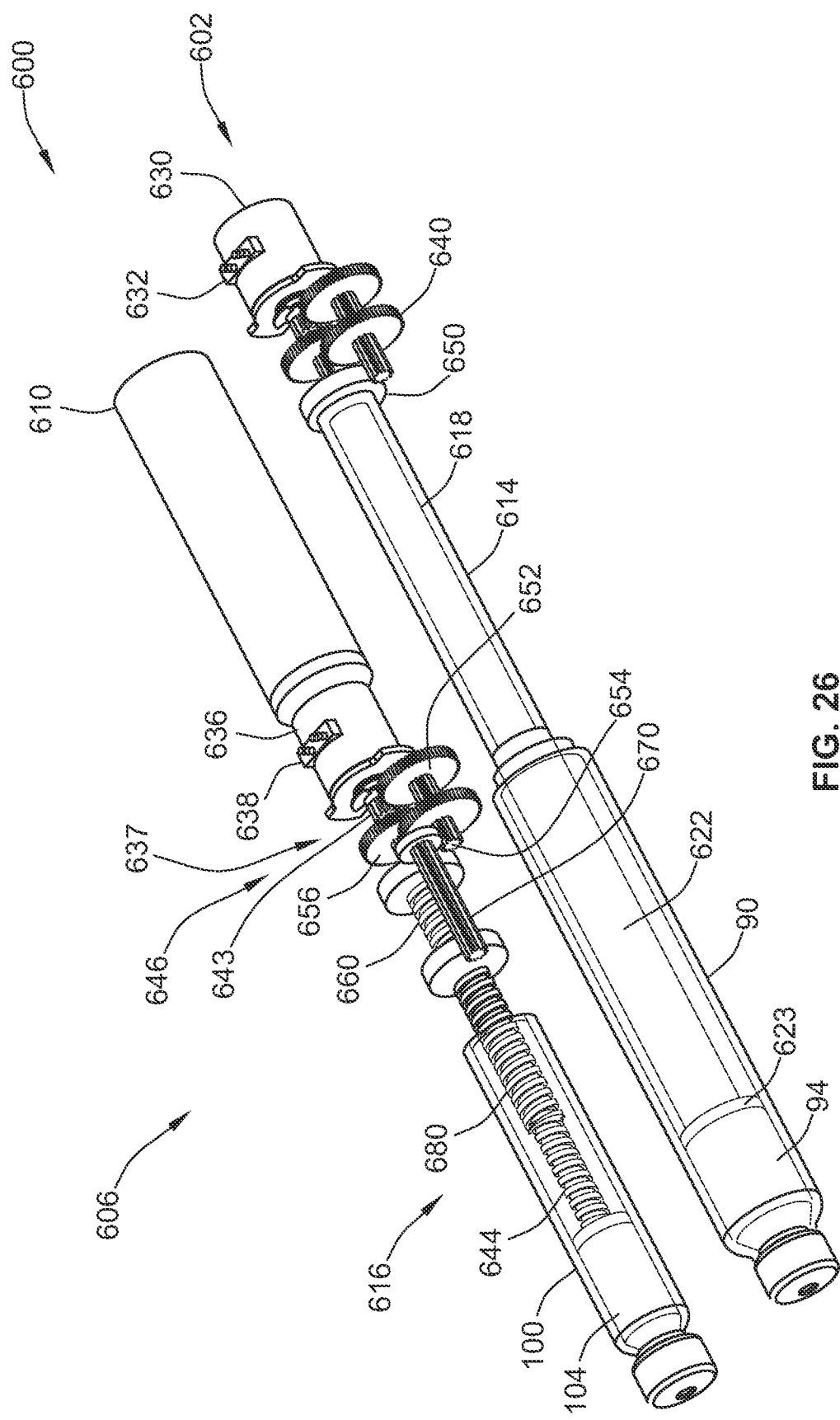
FIG. 26 illustrates a schematic view of the alternative drive mechanism illustrated in FIG. 25 with certain elements removed.

FIG. 26 illustrates the electro-mechanical system illustrated in FIG. 25 with both the digital display 80 and the PCBA 620 omitted. As illustrated, this alternative electro-mechanical system 600 operates to expel a dose from the first cartridge 90 containing a primary medicament 92 and the second cartridge 100 containing a secondary medicament 102. In this preferred electro-mechanical system 600, the system comprises an independent mechanical driver for both the first cartridge and the second cartridge. That is, an independent mechanical driver 602 operates to expel a dose from the first cartridge 90 and an independent mechanical driver 606 operates to expel a dose from the second cartridge 100. If this preferred electro-mechanical system 600 were to be reconfigured to operate on three different medicaments contained within three separate cartridges, three independent mechanical drivers could be provided so as to administer a combined dose. The independent mechanical drivers act under control of the motor drivers 332, 334 of the control unit 300 (see, e.g., FIG. 20).

The first independent mechanical driver 602 operates to expel a dose from the first cartridge 90 and operates in a similar manner as the independent drivers 502, 506 described with reference to the drive train 500 illustrated in FIGS. 22-23 above. That is, this first independent driver 602 comprises a first motor 630 that is operatively coupled to a first gearing arrangement 640. To energize this motor 630, a connector 632 is provided as a means of electrically connecting to the motor driver 332. This first gearing arrangement 640 is mechanically linked to a proximal portion of the telescoping piston rod 614. As this gearing arrangement 640 is driven by an output shaft of the first motor 632, this arrangement 640 rotates the proximal portion 618 of the telescoping piston rod 614. As this proximal portion 618 of the piston rod 614 is rotated, the second or distal portion 622 of the piston rod 614 is driven in a distal direction. Moving in this distal direction, a distal end 623 of the second portion 622 of the piston rod 614 exerts a force on the stopper 94 contained within the first cartridge 90. With a distal end 623 of the piston rod 614 exerting a force on the stopper 94, the user selected dose amount of the first medicament 92 is forced out of the cartridge 90 and into an attached dispense interface 200 and consequently out an attached needle assembly 400 as previously discussed.

Preferably, the first independent mechanical driver 602 comprises a bung or stopper detection system. Such a detection system may be used detect the position of the cartridge stopper 94 following a cartridge change event. For example, when a cartridge change event occurs, the piston rod is retracted in a proximal position so as to enable a user to open the cartridge retainer and thereby provide access to a spent cartridge. When the cartridge is replaced and the cartridge retainer door is shut, the piston rod will advance in a distal direction towards the stopper of new the cartridge.

In one preferred stopper detection system, a switch is provided at the distal end of the piston rod. Such a switch may comprise a mechanical, optical, capacitive, or inductive type switch. Such a switch would be in communication with the microcontroller and indicates when the piston rod is in contact with the stopper and hence may be used as a mechanism for stopping the drive system.

The second independent mechanical driver 606 operates to expel a dose from the second cartridge 100 in a different manner than the first independent driver 602. That is, this second mechanical driver 606 comprises a second motor 636 that is operatively coupled to a second gearing arrangement 646. To energize this motor 636, a connector 638 is provided as a means of electrically connecting to the motor driver 334.

This independent mechanical driver 606 comprises:
tt. A motor 636;
uu. A second gearing arrangement 646; and
vv. A telescope piston rod 616.

The second gearing arrangement 646 is mechanically linked to a proximal portion of a nested piston rod 660. As this gearing arrangement 646 is driven by the output shaft of the second motor 636, this arrangement 646 rotates the proximal portion 660 of the telescoping piston rod 616.

The second gearing arrangement 646 comprises a motor pinion along with a plurality of compound gears (here four compound gears) along with a telescope input piston rod. Two of the compound gears are elongated to enable continuous mesh engagement with the input piston rod as the telescope extends in a distal direction to exert an axially pressure on the cartridge stopper 104 so as to expel a dose from the cartridge. The elongated gear may be referred to as a transfer shaft. The gearbox arrangement preferably has a ratio of 124:1. That is, for every revolution of the telescope input screw the output shaft of the second motor rotates 124 times. In the illustrated second gearing arrangement 646, this gearing arrangement 646 is created by way of five stages. As those skill in the art will recognize, alternative gearing arrangements may also be used.

The second gearing arrangement 646 comprises three compound reduction gears 652, 654, and 656. These three compound reduction gears may be mounted on two parallel stainless steel pins. The remaining stages may be mounted on molded plastic bearing features. A motor pinion 643 is provided on an output shaft of the second motor 636 and is retained on this shaft 637, preferably by way of an interference or friction fit connection.

As described above, the motor pinion 643 may be provided with two mounted "flag" features that interrupt the motion detect optical sensor. The flags are symmetrically spaced around the cylindrical axis of the pinion.

Figure 27:
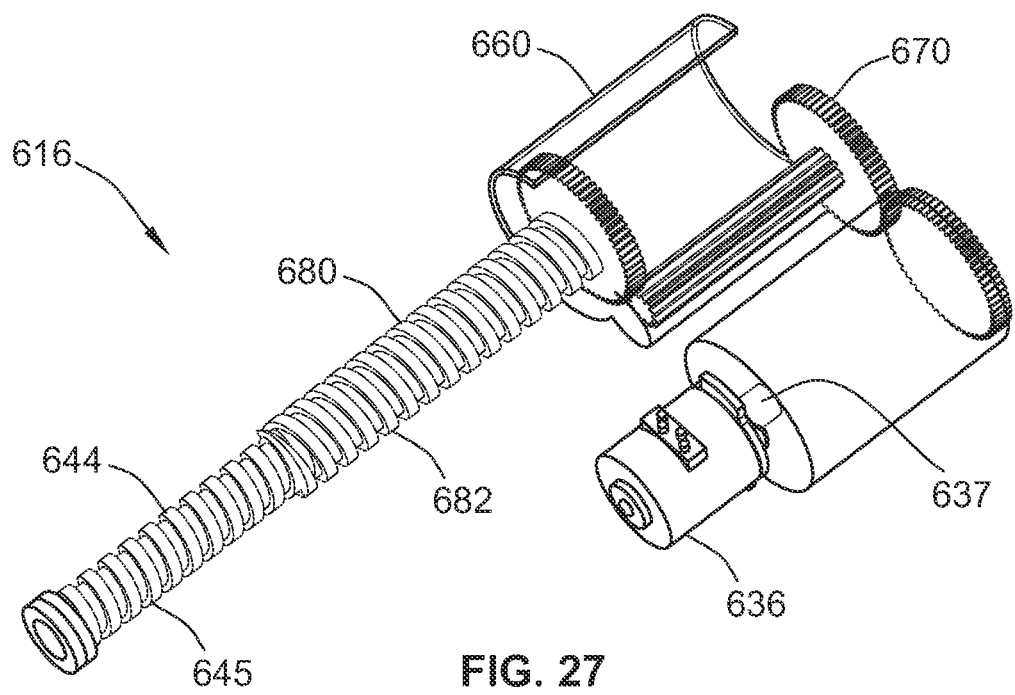
FIG. 27 illustrates a schematic view of a telescope piston rod and gearing arrangement illustrated in FIG. 26.
Figure 28:
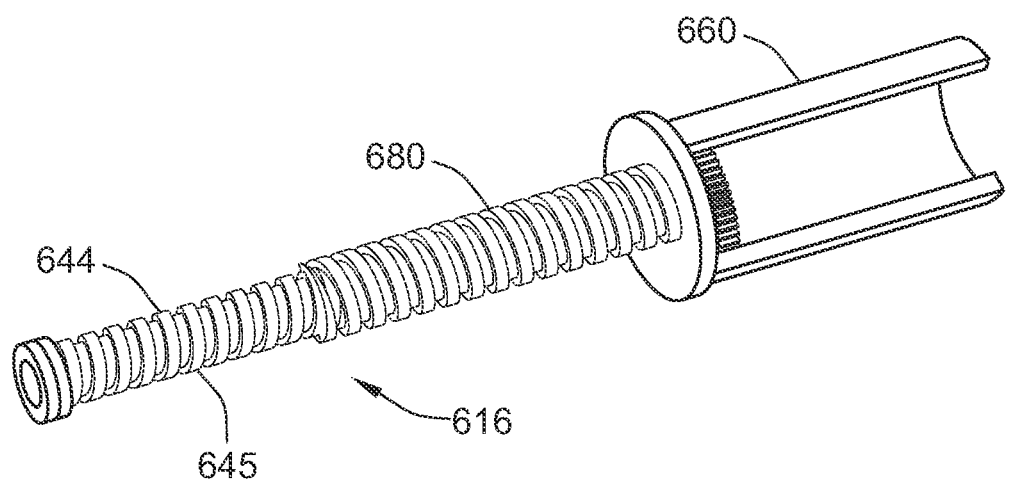
FIG. 28 illustrates a schematic view of a telescope piston rod arrangement illustrated in FIG. 27.
Figure 29:
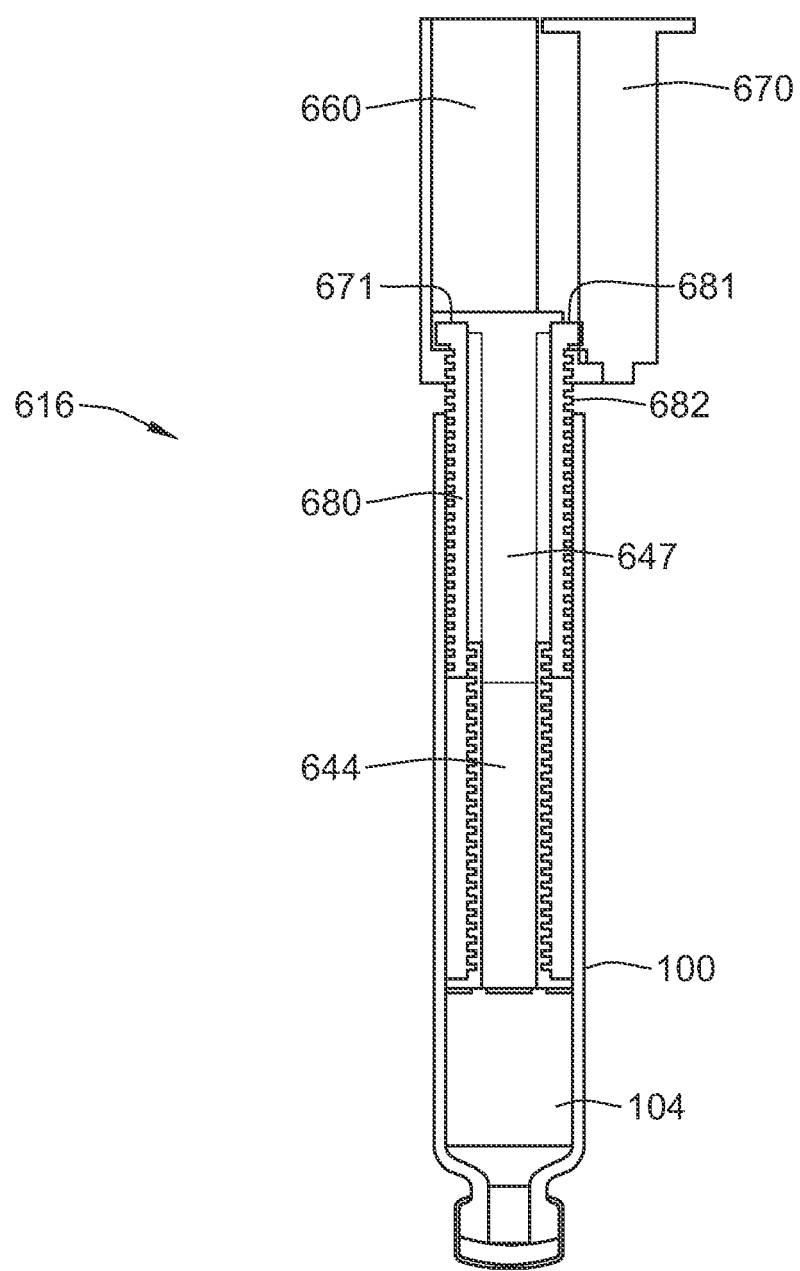
FIG. 29 illustrates a schematic view of one piston rod arrangement illustrated in FIG. 27.

The drive train telescoping piston rod 616 is illustrated in FIG. 27 and comprises a telescope plunger 644 that is operatively coupled to an input screw 680. FIG. 28 illustrates a perspective view of the telescope piston rod 616 coupled to a latch barrel. FIG. 29 illustrates a cross sectional view of the independent mechanical driver with the piston rod 616 in an extended position.

As illustrated, the outer elements (the telescope piston rod plunger 644 and telescope) create the telescopic piston rod 616 and react to the compressive axial forces that are developed. An inner element (telescope piston rod key 647 provides a means of reacting the rotational input force. This operates with a continuous motion and force since there will be no changes in drive sleeve diameter to generate varying levels of force.

The transfer shaft 670 is operatively linked to the gearing arrangement 646. The transfer shaft 670 can rotate but it cannot move in an axial direction. The transfer shaft 670 interfaces with the second gearing arrangement 646 and transfers the torque generated by the second gearbox arrangement 646 to the telescope piston rod 616.

Specifically, when the transfer shaft 670 is rotated by way of the gearing arrangement 646, the transfer shaft 670 will act on an integrated geared part 681 on a proximal end of the input screw 680. As such, rotation of the transfer shaft 670 causes the input screw 680 to rotate about its axis.

A proximal portion of the input screw 680 comprise a threaded section 682 and this threaded section is mated with a threaded section of the latch barrel 660. As such, when the input screw 680 rotates, it winds or screws itself in and out of the latch barrel 660. Consequently, as the input screw 680 moves in and out of the latch barrel, the screw 680 is allowed to slide along the transfer shaft 670 so that the transfer shaft and the gears remain mated.

The telescope plunger 644 is provided with a threaded section 645. This threaded section 645 is threaded into short section in distal end of the input screw 680. As the plunger 644 is constrained from rotating, it will wind itself in and out along the input screw 680.

A key 647 is provided to prevent the plunger 644 from rotating. This key 647 may be provided internal to the input screw 680 of the piston rod 616. During an injection step, this key 647 moves in the axial direction towards the stopper 104 of the cartridge 100 but does not rotate. The key 647 is provided with a proximal radial peg that runs in a longitudinal slot in the latch barrel 660. Therefore, the key 647 is not able to rotate. The key may also be provided with a distal radial peg that engage a slot in the plunger 644.

Preferably, the drug delivery device 10 comprises memory devices comprising enough memory storage capability so as to store a plurality of algorithms that are used to define a plurality of different therapeutic profiles. In one preferred arrangement, after a user sets a dose of the primary medicament, the drug delivery device will be preprogrammed so as to determine or calculate a dose of the secondary medicament and perhaps a third medicament based on one of the stored therapeutic profiles. In one arrangement, the healthcare provider or physician selects a therapeutic dose profile and this profile may not be user alterable and/or may be password protected. That is, only a password known by the user, for example a healthcare provider or physician, will be able to select an alternative profile. Alternatively, in one drug delivery device arrangement, the dose profile is user selectable. Essentially, the selection of the therapeutic dose profiles can be dependent upon the individualized targeted therapy of the patient.

Figure 30:
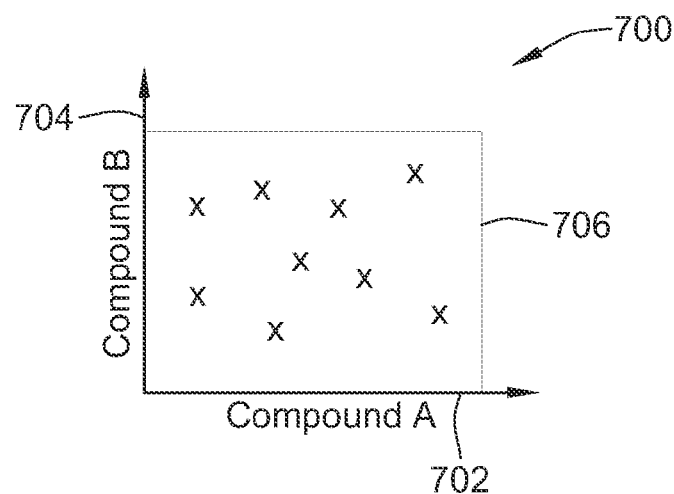
FIG. 30 illustrates a potential deliverable therapy of a known two input and two compound combination device.

As described above, certain known multi drug compound devices allow independent setting of the individual drug compounds. As such, the delivery of the combined dose in a combination is determined by a user. This is not ideal in all the therapeutic situations that a patient may face. For example, FIG. 30 illustrates a potential deliverable therapy 700 of such a known two input and two compound combination device: that is, a device that requires a user to physically set the first dose of a first medicament and then physically set the second dose of the second medicament. In such a known device, a user could select a dose of the Compound A or the primary medicament 702 along the x-axis (i.e., between 0 units to a top dose). Similarly, the user could then select a dose of the secondary medicament—Compound B 704 along the y-axis (i.e., between 0 units to a top dose). As such, although these known devices can potentially deliver the combination of the two compounds as illustrated by area 706 shown in FIG. 30, there is an inherent risk that the user does not follow the correct, prescribed therapeutic profile, either intentionally or otherwise. For example, in such a device, the user must know, or be able to determine or calculate, the required relationship and then set the dose of both the first and second compounds 702, 704 independently.

One of the primary reasons for combining drug compounds is that generally all the pharmaceutical elements are required to ensure an increased therapeutic benefit to a patient. In addition, some compounds and some combinations of compounds need to be delivered in a specific relationship with each other in order to provide the optimum pharmacokinetic ("PK") and pharmacodynamic ("PD") response. Such complex relationships between one, two, or more (i.e., more than a plurality) of medicaments may not be achievable through a single formulation route and could potentially be too complex for the user to understand, or follow correctly, in all cases.

Figure 31A:
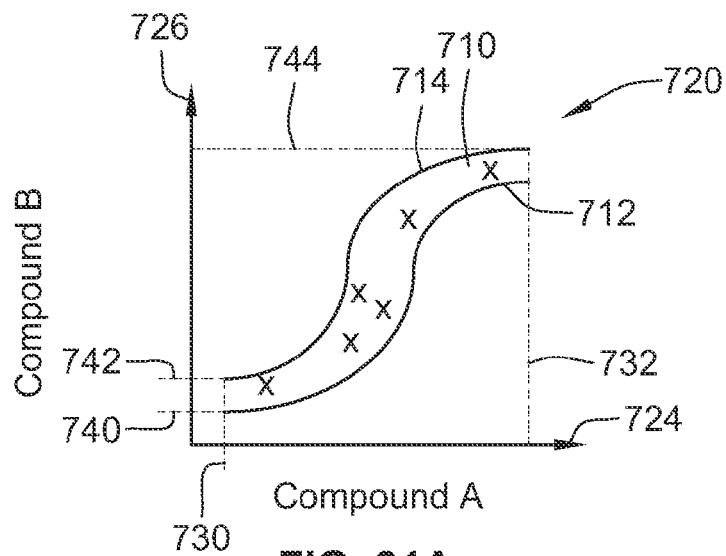
FIGS. 31a and 31b illustrate a first arrangement of a pre-defined therapeutic profile that may be programmed into the disclosed' programmable drug delivery device.
Figure 31B:
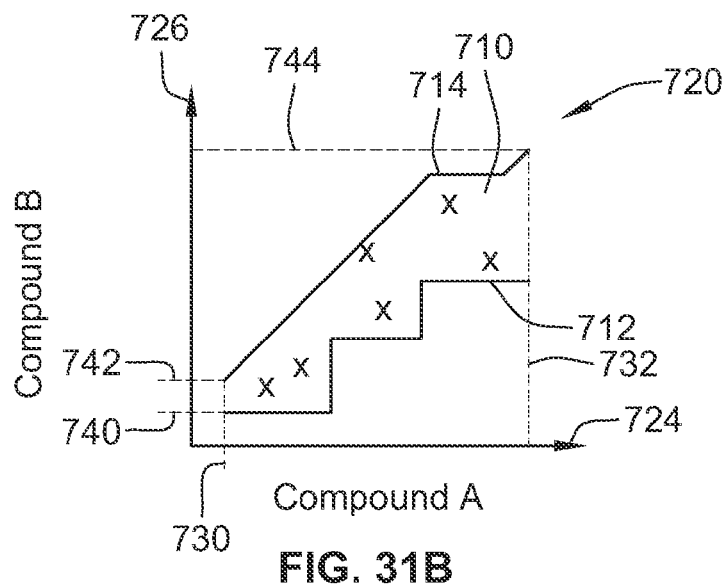

In an example embodiment of the disclosure, a multi drug compound device may be reliant upon the user input for each independent compound to control the delivered dose profile within predetermined thresholds. For example, FIGS. 31a and 31b illustrate in diagrammatic form a potential delivered therapy 720 of a theoretical two input, two compound combination device. The area 710 illustrates the range of potential combination doses that are achievable. That is, a user can set the dose of the primary medicament or Compound A 724 anywhere from a minimum value 730 to a maximum value 732. Similarly, the user can separately and independently set the dose of the secondary medicament or Compound B 726 anywhere from a minimum value 740 to an overall maximum value 744 within predetermined thresholds, for example between a lower limit 712 and an upper limit 714. In this area 710, the plurality of 'X' designations illustrate specific combination doses that a patient and/or user of such a device may elect to set and deliver. Essentially, the combined dose of Compound A 724 and Compound B 726 can be set anywhere within this area 710. In the example embodiment, the user is limited to setting a combined dose only along a predefined profile, such as the predefined profile illustrated by area 710 in FIGS. 31a and 31b. For example, if an amount of Compound A is selected by a user to be the minimum value 730, Compound B may be selected between the minimum value 740 and a maximum value 742 defined for this minimum value of Compound A.

The lower limit 712 and the upper limit 714 may be represented by a curve as in FIG. 31a. In an alternative embodiment, the lower limit and the upper limit may be represented by one or more lines, by a stepwise function, and/or the like. For example, in the diagram of FIG. 31b, the upper limit 714 is represented by a diagonal line and a horizontal line, the lower limit 712 is represented by a stepwise function of 3 steps. The upper limit 714 and the lower limit 712 define an area 710, in which a user may select a combination of Compound A and Compound B, for example one of the combinations designated by the 'X'-marks.

In further example embodiments, the presently proposed programmable electro-mechanical drug delivery device described in detail above uses only a single input in order to offer an innovative solution to these and other related problems. In further embodiments, the proposed programmable multi-drug compound device uses only a single dispense interface. As just one example, such a device is capable of delivering any of a plurality of predefined programmed therapeutic profiles for various drug combinations. As an alternative, such a device is capable of delivering only one predefined programmed therapeutic profile for various drug combinations.

By defining the ratio-metric relationship or relationships between the various individual drug compounds (2, 3, or more), the proposed device helps to ensure that a patient and/or user receives the optimum therapeutic combination dose from a multi drug compound device. This can be accomplished without the inherent risks associated with multiple inputs. This can be achieved since the patient and/or user is no longer called upon to set a first dose of medicament and then determine or calculate and then independently set a correct dose of a second and/or third medicament in order to arrive at the correct dose combination each time the device is used to administer a combination dose.

As just one example, FIG. 32 illustrates a first arrangement of a predefined therapeutic profile 760 that may be programmed into the disclosed programmable drug delivery device. In FIG. 32, a first therapeutic dose line represents an example of a predefined therapeutic profile 760 compared to the area 706 indicating all potential drug combinations that can be selected by way of currently known devices as illustrated in FIG. 30. As can be seen from this predefined profile 760 illustrated in FIG. 32, for every dose value of Compound A 764 (also herein referred to as the Master Drug or the Primary Drug or the Primary Medicament) selected by the user, the disclosed drug delivery device 10 will rely on a previously stored therapeutic profile to calculate the dose value of Compound B 766 along this therapeutic profile 760.

As such, the user merely needs to select a first dose of the first drug: Drug A or the primary medicament and the disclosed drug delivery device 10 automatically calculates the dose of the secondary medicament or Drug B based on this preselected dosing profile 760. For example, if the user selects a dose comprising "60 Units" for Compound A 764, the drug delivery device 10 will recall the selected dosing profile 760 from its memory device and then automatically calculate the dose value of "30 Units" for Compound B 766.

In an alternative drug delivery device arrangement, and as discussed in greater detail above, the drug delivery device may comprise a coding system. A coding system may be provided if coding means is provided on either the first or the second cartridge so that the drug delivery device could then identify the particular medicament contained within an inserted cartridge. After the drug delivery device undergoes a method or process for determining cartridge and/or medicament identification, the drug delivery device could then potentially automatically update the therapeutic profile or profiles. For example, a new or a revised/updated profile may be selected if required to reflect an updated or revised pharmaceutical philosophy so as to achieve an optimum medicament relationship. Alternatively, a new or a revised/updated profile may be selected if a health care provider has decided to alter a patient's therapy strategy. An updated or revised profile may be loaded into the device through a wired or wireless connection, for example from a memory comprised in the cartridge, from an external device, from the internet and/or the like. The updated or revised profile may be loaded automatically, for example after insertion of the cartridge, or only after user confirmation, for example after a user presses a button on the device to confirm a message shown in the display.

As another example of a therapeutic profile, the proposed drug delivery device 10 may be programmed to calculate a linear ratio profile for the delivered dose from the drug delivery device 10 that comprises two or more discrete medicament reservoirs.

For example, with such a programmed therapeutic profile, the constituent components of the dose would be delivered to a patient in a fixed, linear ratio. That is, increasing the dose of one element will increase the dose of the other constituent element(s) by an equal percentage. Similarly, reducing the dose of one element will reduce the dose of the other constituent element(s) by an equal percentage. Any therapeutic dose profile could be calculated in accordance with the disclosure.

Discussed below are various examples of drug delivery device, for example electro-mechanical devices, that are configured to prevent a user from administering a dose while a connector of a main body of the device is electrically connected to a corresponding electrical connector. In particular, a user may be prevented from using the device to inject a dose of medicament while the device is connected to an external device.

Figures 32A, 32B:
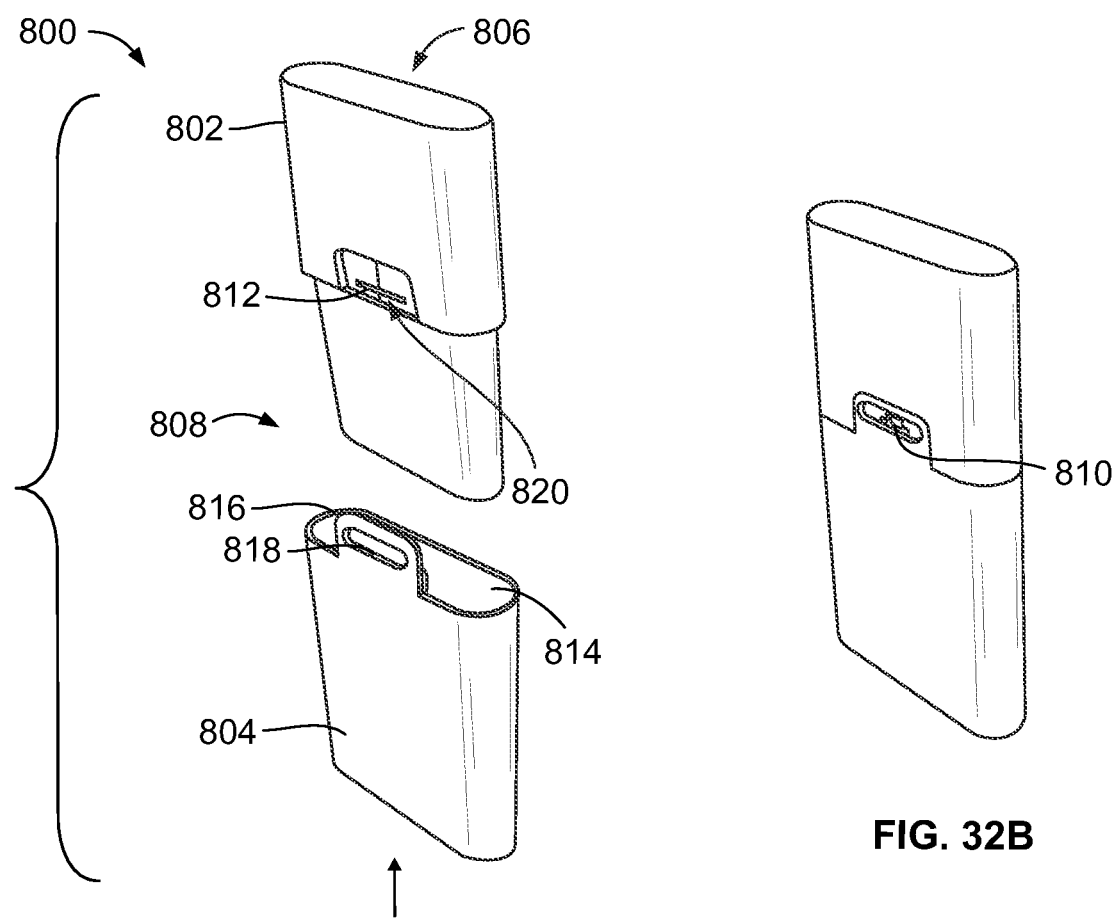
FIGS. 32a and 32b illustrate a perspective view of an exemplary drug delivery device.

A first example of an electro-mechanical drug delivery device that is configured to prevent a user from using the device to inject or to administer a dose of medicament while the device is connected to an external device is shown in FIGS. 32a and 32b. In particular, FIGS. 32a and 32b show a drug delivery device 800 that includes a main body 802 and a separable housing 804. Main body 802 has a proximal end 806 and a distal end 808. The distal end 808 is configured to attach to a dispense interface (e.g., a double ended needle assembly or an interface as illustrated in FIGS. 11-19 and as described in detail herein). As just one example, the distal end 808 may include a threaded needle hub to which a dispense interface may attach, such as the threaded needle hub 216 shown in FIG. 2.

The separable housing 804 can prevent an administration (i.e., an injection) of a drug contained within the drug delivery device 800. The separable housing 804 is configured to cover at least a portion of the distal end 808 of the main body 802 when the separable housing 804 is coupled to the drug delivery device 800. In this example, the separable housing 804 covers approximately the bottom half of the main body 802. However, it should be understood that a separable housing could cover more or less of the main body while still functioning to prevent administration when the separable housing is attached to the main body. Separable housing 804 acts to prevent administration of a drug by, for example, preventing the dispense interface from attaching to the main body. In an example, separable housing 804 prevents the dispense interface from attaching to the main body by covering a needle hub to which the dispense interface is intended to attach. In this situation, it may not be possible to attach the separable housing 804 to the main body 802 when a dispense interface is attached to the needle hub. However, in other cases, the separable housing 804 may be configured to be attached to the main body 802 both when a dispense interface is not attached and when a dispense interface is attached. In either of these situations, a user cannot administer a dose from drug delivery device 800 when the separable housing 804 is attached to main body 802.

With reference to FIG. 32b, a conduction element 810 is provided by main body 802. This conduction element 810 is configured for establishing an electrical connection with a corresponding electrical connector. The corresponding electrical connector may be an electrical connector of an external device (not shown). In this example depicted in FIG. 32b, the conduction element 810 comprises a Universal Serial Bus (USB) port. Therefore, in this example, the corresponding electrical connector would comprise a corresponding USB plug. It should be understood that although in this example the conduction element is a USB port and the corresponding electrical connector is a USB plug, the conduction element and corresponding electrical connector may take any form now known in the art or later developed. For example, the conduction element may be a Firewire port and the corresponding electrical connector may be a Firewire plug. In another example, the conduction element may be a RS232 port and the corresponding electrical connector may be a RS232 plug. In yet another example, the conduction element may be a proprietary port and the corresponding electrical connector may be a proprietary plug. Further, in each of the examples above, the main body may include the plug and the external device may include the port. In this case, the plug may be understood as a conduction element and the port may be understood as the electrical connector.

Conduction element 810 is configured for establishing an electrical connection with the corresponding electrical connector when the conduction element 810 is connected to a corresponding electrical connector. The electrical connection established is a connection between the connector and the conduction element. Establishment of the electrical connection may allow for current to flow from the external device to the electro-mechanical drug delivery device. This may allow for transfer of data and/or transfer of power from the external device to the drug delivery device. However, establishment of this electrical connection is prevented when the separable housing 804 does not cover at least a portion of the distal end 808 of the main body 802. For example, an electrical connection cannot be established when the separable housing 804 is separated from the main body 802, as shown in FIG. 32a. In contrast, the electrical connection may be established only when the separable housing 804 covers at least a portion of the distal end 808 of the main body 802. For example, the electrical connection can be established when the separable housing is coupled to the main body 802, as shown in FIG. 32b.

With reference to FIG. 32a, the conduction element 810 is covered, so that a connector could not connect to the conduction element 810. It should be understood that in this state, the conduction element 810 may be covered or partially covered in any way that prevents the connector element from connecting to the conduction element 810. However, in FIG. 32b, the separable housing 804 covers the distal end 808, and establishment of the electrical connection is possible.

The drug delivery device 800 may be configured to allow establishment of the electrical connection when the separable housing 804 is attached to main body 802, but not when the separable housing is unattached to main body 802, in a variety of ways. In an example, the main body 802 of the drug delivery device may include a sliding or retracting door or cover 812 that covers (or at least partially covers) the USB port 810 when the separable housing 804 is not connected to the device 800. This may be a sliding door that is capable of moving from a closed position to an open position and vice versa. In the closed position, the sliding door 812 covers the USB port 810. In contrast, in the open position, the USB port 810 is not covered by the sliding door 812. Thus, the USB port 810 is only accessible when the separable housing 804 is coupled to the main body 802.

Returning to FIG. 32*a*, the proximal end 814 of separable housing 804 includes a protrusion 816 that has an opening 818. When the separable housing 804 is attached to the main body 802, this opening 818 aligns with a corresponding indentation 820 on the outer edge of main body 802. When the separable housing 804 is fitted on the device, the opening 818 provides a hole that a USB plug can go through to connect with USB port 810. Attachment of the separable housing 804 to the main body 804 may serve to move the sliding door 812 from its closed position to its open position.

As explained above, the sliding door 812 will be in the closed position when the separable housing 804 is not attached to the main body 802. In an exemplary device, in order to prevent a user from forcing the sliding door open when the separable housing is not connected, the drug delivery device 800 may include a mechanical interlock that operates to ensure that a user cannot easily open the sliding door when the separable housing 804 is not fitted on the main body 802. In another example, the drug delivery device may be configured such that, if such a mechanical interlock were to malfunction, the device would prevent a user from operating the drug delivery device to select a dose and/or inject a dose.

In an example, the conduction element is configured for establishing the electrical connection with the corresponding electrical connector for a transfer of power. The conduction element may be communicatively linked to a rechargeable battery, and the electrical connector may be linked to a power source. Therefore, when the electrical connection is established, the external device may charge the rechargeable battery. In another example, the conduction element is configured for establishing the electrical connection with the corresponding electrical connector for a transfer of data. Other reasons for connecting to an external device are possible as well.

In some situations, the sliding door 812 may be in the open position whenever the separable housing 804 is attached to the main body 802. However, in other situations, the drug delivery device 800 may be configured such that the sliding door 812 is not always in the open position when separable housing 804 is disposed on main body 802. Rather, the drug delivery device may be configured such that the sliding door 812 is in the open position only when (i) separable housing 804 is disposed on main body 802 and (ii) the user attempts to connect an external device. Preventing the sliding door 812 from always being open when the end cap or separable housing is attached may help to prevent dust or dirt ingress due to an exposed conduction element.

In addition, the separable housing and main body may be configured in other ways to allow for an electrical connector to connect to a conduction element when the separable housing is attached to the main body. For example, rather than including a sliding door, the main body may comprise a pivoting member.

For example, FIGS. 33*a*-33*d* illustrate one such drug delivery device comprising a pivoting member 832. Such drug delivery device 821 comprises an electro-mechanical drug delivery device that is configured to prevent a user from using the device to inject or to administer a dose of medicament while the device is connected to an external device. In particular, FIGS. 33*a*-33*d* show a drug delivery device 821 that includes a main body 822 and a separable housing 824. Main body 821 has a proximal end 826 and a distal end 828. The distal end 828 is configured to attach to a dispense interface.

The separable housing 824 can prevent an administration (i.e., an injection) of a drug contained within the drug delivery device 821. The separable housing 824 is configured to cover at least a portion of the distal end 828 of the main body 822 when the separable housing 824 is coupled to the drug delivery device 821. Separable housing 824 acts to prevent administration of a drug by, for example, preventing the dispense interface from attaching to the main body. In an example, separate housing 824 prevents the dispense interface from attaching to the main body by covering a needle hub to which the dispense interface is intended to attach. In this situation, it may not be possible to attach the separable housing 824 to the main body 822 when a dispense interface is attached to the needle hub.

Figure 33A:
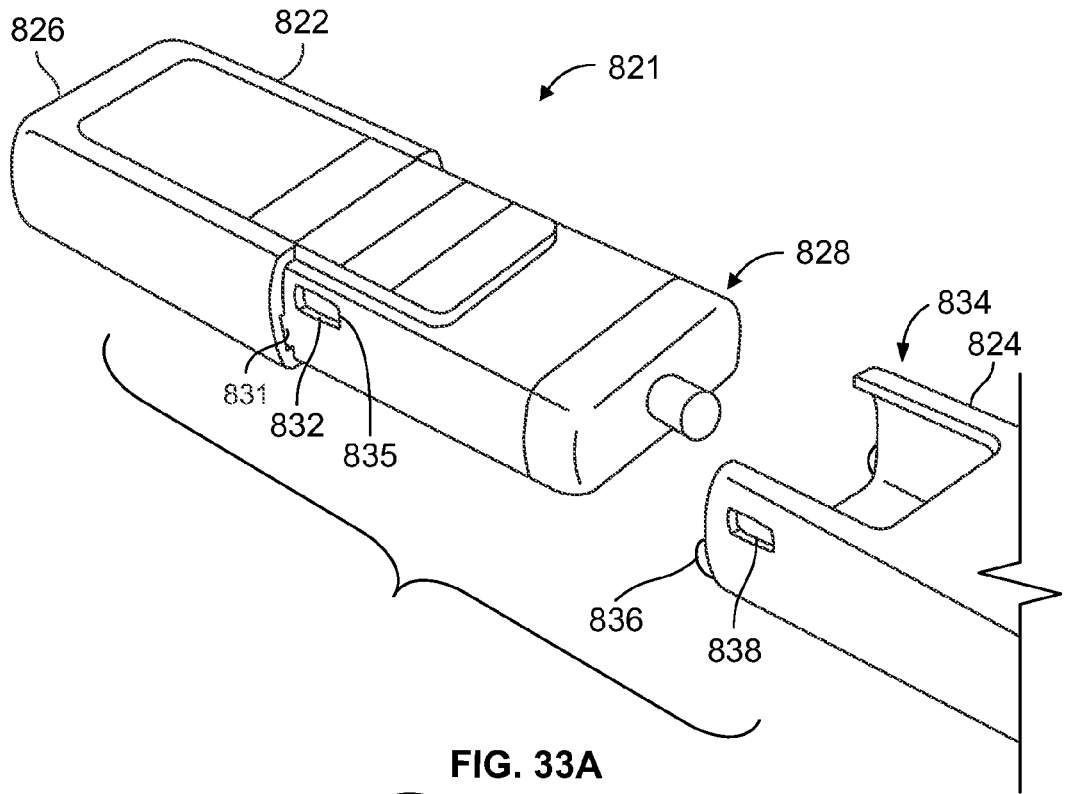
FIGS. 33a to 33d illustrate a perspective view of another exemplary drug delivery device.
Figure 33B:
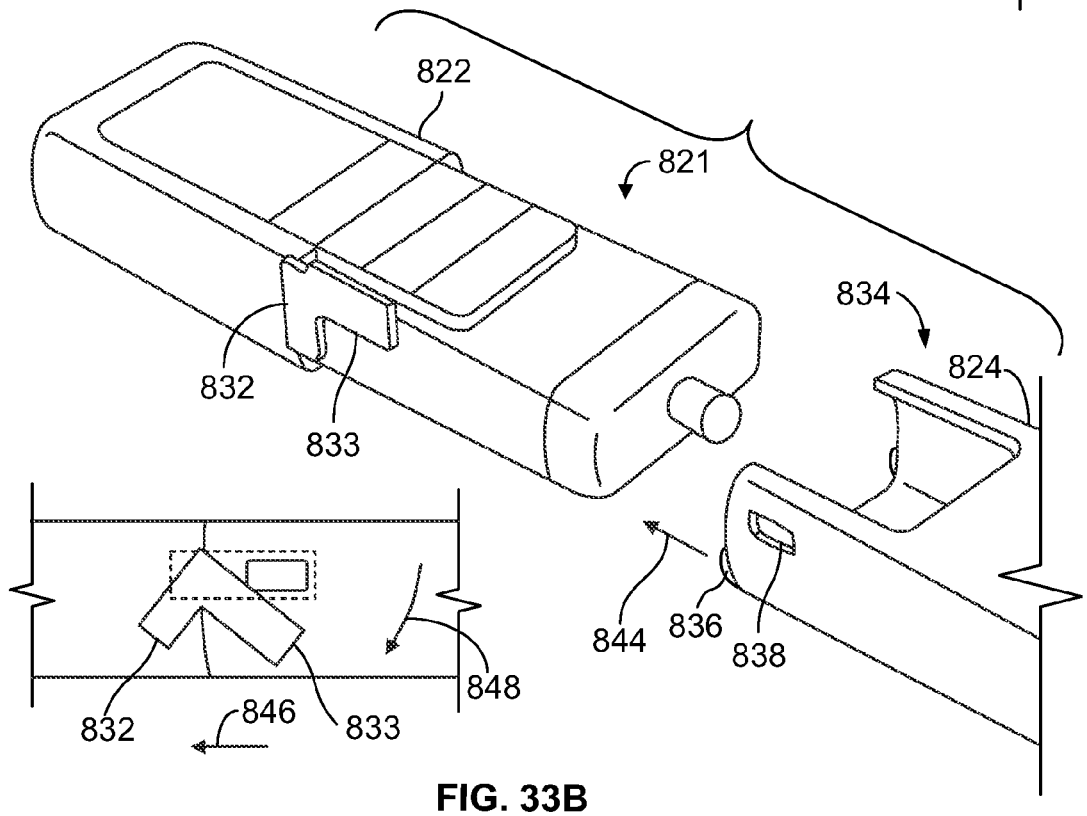
Figure 33C:
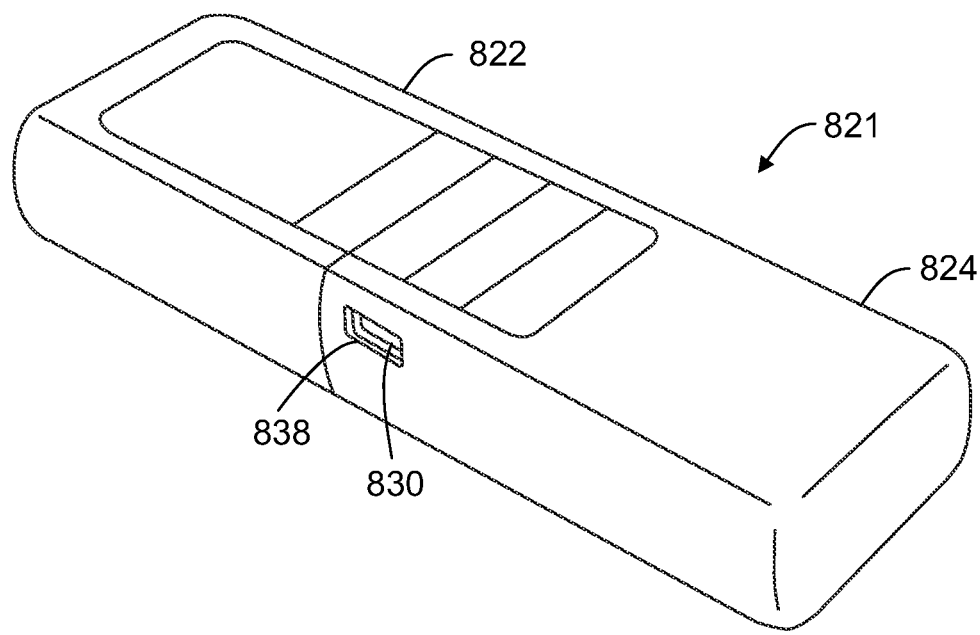
Figure 33D:
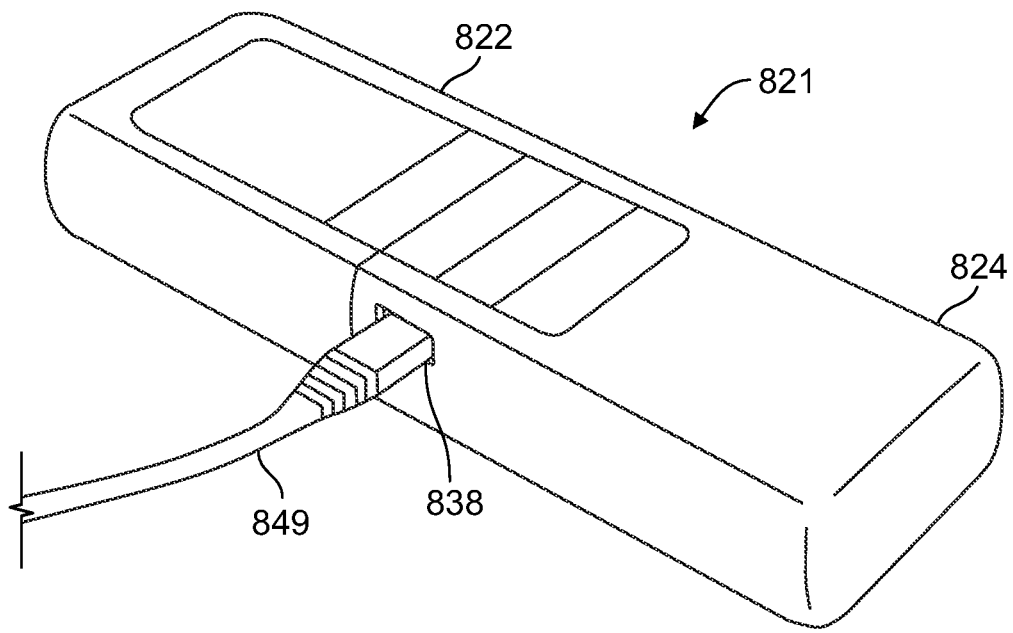

The main body 822 of the device comprises a conduction element 830 (see FIG. 33*c* with separable housing 824 attached to the main body). This conduction element 830 is configured for establishing an electrical connection with a corresponding electrical connector. For example, FIG. 33*d* illustrates a corresponding electrical connector 849 connected with the conduction element 830 after the housing 824 has been attached to the main body 822. In example depicted in FIGS. 33*c* and 33*d*, the conduction element 830 may comprise a Universal Serial Bus (USB) port and the corresponding electrical connector 849 would comprise a corresponding USB plug.

Conduction element 830 is configured for establishing an electrical connection with the corresponding electrical connector when the conduction element 830 is connected to a corresponding electrical connector. However, establishment of this electrical connection is prevented when the separable housing 824 does not cover at least a portion of the distal end 828 of the main body 822. For example, an electrical connection cannot be established when the separable housing 824 is separated from the main body 822, as shown in FIGS. 33*a* and 33*b*. In contrast, the electrical connection can be established when the separable housing is coupled to the main body 822, as shown in FIG. 33*c*. As illustrated in FIG. 33*c*, the conduction element 830 remains uncovered and accessible through an access point 838 provided at a proximal end of the separable housing 824.

With reference to FIGS. 33*a* and 33*b*, when the housing is removed from the main body, the conduction element 810 is covered by a pivoting door 832, so that a connector (such as connector 849) would be blocked from connecting to the conduction element 830. In FIG. 33*a*, the pivoting door 832 is not depicted in order to make the narrow slot 831 and the access point 835 visible, which would be otherwise concealed by the pivoting door 832, as can be seen in FIG. 33*b*. However, in FIG. 33*c*, the separable housing 824 covers the distal end 808, and establishment of the electrical connection is made possible.

The drug delivery device 821 is configured to allow establishment of the electrical connection when the separable housing 824 is attached to main body 822, but not when the separable housing is attached to main body 822. In this illustrated example, the main body 822 of the drug delivery device includes a pivoting member 832 that covers (or at least partially covers) the conducting element 830 when the separable housing 824 is not connected to the device 821.

The pivoting member 832 is capable of moving from a closed position (shown in FIG. 33*b* to an open position (shown in FIG. 33*c*) and vice versa. In the closed position, the pivoting member 832 covers the conduction element 830. In contrast, in the open position, the conduction element 830 is not covered by the pivoting member 832. Thus, the conducting element 830 is only accessible when the separable housing 824 is coupled to the main body 822.

Returning to FIGS. 33*a* and 33*b*, the proximal end 834 of separable housing 824 includes a protrusion 836 and also comprises an access point 838. As illustrated in FIG. 33*b*, when the separable housing 824 is axially attached to the main body 822 in the direction of arrow 844, the protrusion 836 will enter a narrow slot 831 provided on the main body. With the protrusion moving in the axial direction 846 within the narrow slot 831, the protrusion 836 will act on the pivoting member 832. Member 832 will therefore pivot by operation through a rotating or pivoting "L" shaped lever 833. Where the pivoting member 832 resides in a closed position, the lever 833 and hence the pivoting member 832 will block access to the access point 835 provided on the main body. When the separable housing 804 is complete fitted on the drug deliver device 821, the access point 838 on the housing 824 will match up with the access point 835 on the main body to provide a hole that an electrical connector, for example a USB plug, can go through to connect with conduction element 830. As such, attachment of the separable housing 824 to the main body 824 serve to move the pivoting member 832 from its closed position to its open position.

Figure 34B:
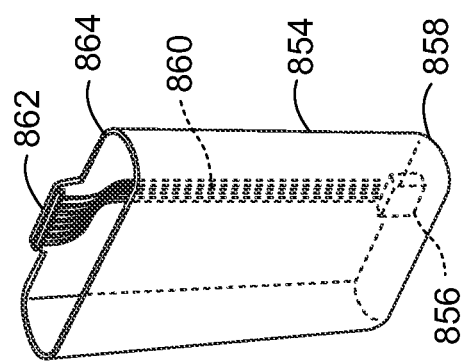
FIGS. 34a and 34b illustrate a perspective view of yet another exemplary drug delivery device.
Figure 34A:
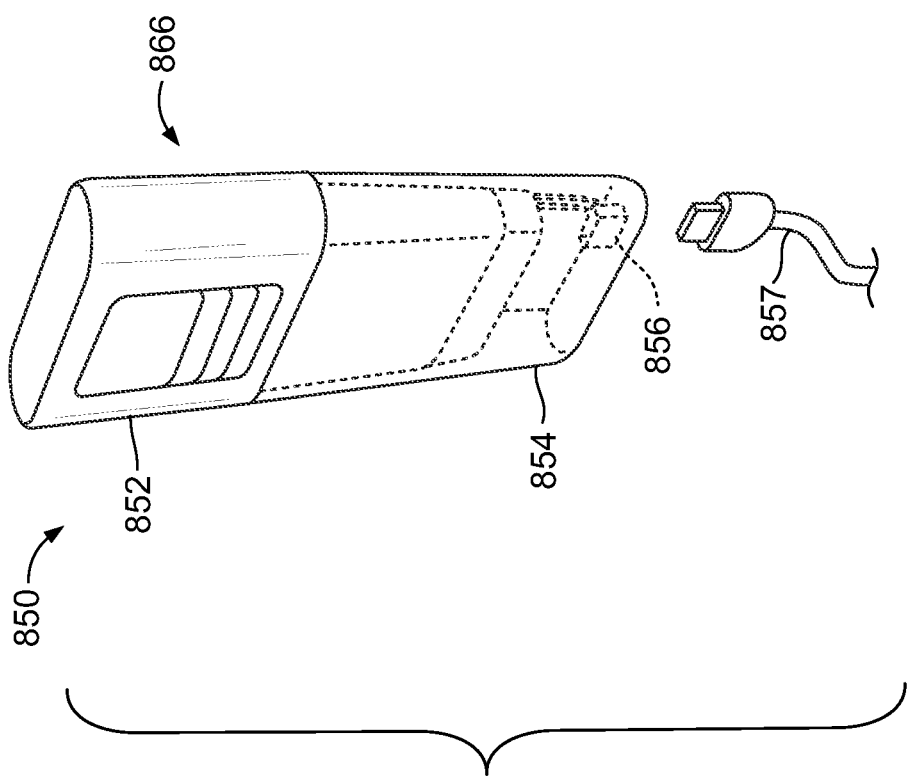

Yet another example of an electro-mechanical drug delivery device that is configured to prevent a user from using the device to inject a dose of medicament while the device is connected to an external device is shown in FIGS. 34*a* and 34*b*. As illustrated, FIGS. 34*a* and 34*b* illustrate an electro-mechanical drug delivery device 850 that includes a main body 852 and a separable housing 854. Specifically, FIG. 34*a* shows a perspective view of the separable housing 854 attached to the main body 852, and FIG. 34*b* shows a perspective view of the separable housing 854 where this housing is not connected to the main body 852.

The drug delivery device 850 further includes a conduction element 856 disposed in the separable housing 854. In this example, the conduction element 856 is once again depicted as a USB port. The USB port 856 can communicate with an external corresponding electrical connector, shown in FIG. 34*a* as USB plug 857. As described above with respect to exemplary drug delivery devices, the conduction element 856 and electrical connector 857 may be any conduction element and connector now known in the art or later developed.

In this example, the USB port 856 is disposed in the distal end 858 of the separable housing 854. The USB port 856 is connected to a wire 860, and this wire 860 is also connected to connector 862. In this example, connector 862 is disposed near the proximal end 864 of separable housing 854. Connector 862 may be any connector that operates to connect the USB port 856 to an electronic control unit and/or battery of drug delivery device 850. In this example, connector 862 is depicted as a custom blade connector. Although not shown in FIG. 34*a*, the back 866 of main body 852 includes an electrical connector or connection corresponding to custom blade connector 862. This corresponding connection may be communicatively linked to the electronic control unit of drug delivery device 850.

When the separable housing 854 is connected to the main body 852, connector 862 may be in communication with the electronic control unit of the drug delivery device 850 and the USB port 856 may be in communication with the electronic control unit of the drug delivery device 850. The user can connect electrical connector 857 to USB port 856 in order to, for example, facilitate transfer of power or transfer of data to or from the external device to the drug delivery device 850. In this situation, since the separable housing 854 is located over the portion of the main body that a dispense interface can be attached to, a user cannot administer a dose while the USB plug 857 is connected to the drug delivery device 850. When the separable housing 854 is removed, the electrical connection between the external device and the drug delivery device 850 is disconnected. Therefore, a user can safely use the drug delivery device 850 for drug administration.

Yet another example of an electro-mechanical drug delivery device that is configured to prevent a user from using the device to administer a dose of medicament while the device is connected to an external device is shown in FIGS. 35*a* and 35*b*. This example is somewhat similar to the example depicted in FIGS. 34*a* and 34*b* and thus is not described in as great of detail. It should be understood, however, that any of the permutations and possibilities described with reference to FIGS. 34*a* and 34*b* may be possible as well in the example of FIGS. 35*a* and 35*b*. Similar to the example of FIGS. 34*a* and 34*b*, the example of FIG. 35 illustrates a conduction element disposed in the separable housing. However, in this example, a different example connection between the conduction element and the electronic control unit of the device is shown.

In particular, FIGS. 35*a* and 35*b* illustrate an electro-mechanical drug delivery device 900 that includes a main body 902 and a separable housing 904. Specifically, FIG. 35*a* shows separable housing 904 attached to the main body 902, and FIG. 35*b* shows a perspective view of the separable housing 904 that is not connected to the main body 902.

The drug delivery device 900 further includes a conduction element 906 disposed in the separable housing 904. In this example, the conduction element 906 is depicted as a USB port. The USB port 906 can communicate with an external corresponding electrical connector, shown in FIG. 35*a* as USB plug 907. As with the example described above with respect to FIGS. 34*a* and 34*b*, the conduction element and electrical connector may be any conduction element and connector now known in the art or later developed. Rather than including a blade connector as in FIGS. 34*a* and 34*b*, the conduction element 906 of drug delivery device 900 may comprise a custom or proprietary connector. In this example, the conduction element 906 may be disposed at a distal end 908 of the separable housing. The conduction element 906 is integrally formed with an electrical connector, which may be connected to the distal end 910 of the main body 902 when the separable housing 904 is coupled to the main body 902. Accordingly, the conduction element 906 and the electrical connector are configured as integral parts of a connector member.

Figure 36B:
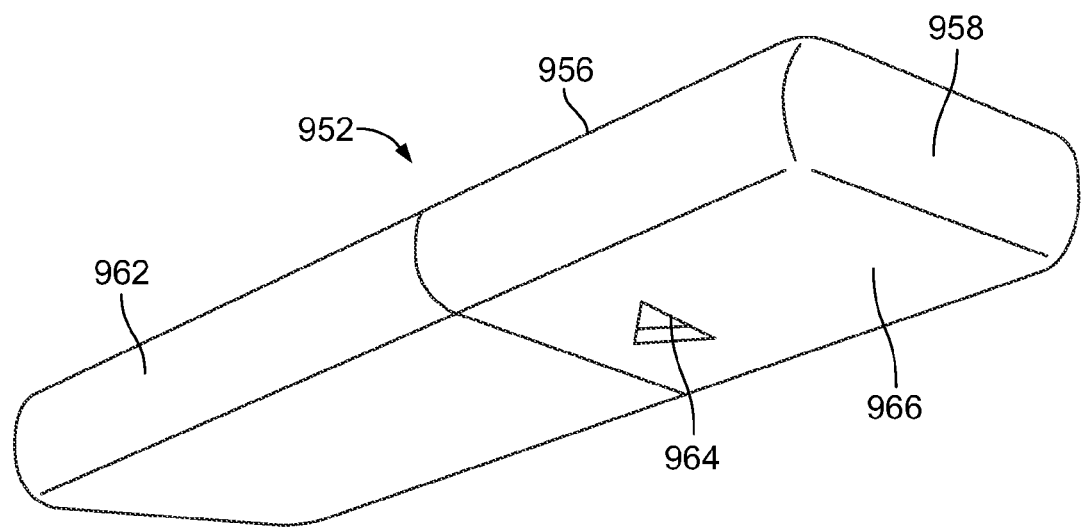

Yet another example of an electro-mechanical drug delivery device that can be configured to prevent a user from using the device to administer a dose of medicament while the device is connected to an external device is shown in FIGS. 36*a* and 36*b*. In this example, a user may connect the electro-mechanical drug delivery device to an external device via a docking station. Beneficially, the drug delivery device cannot be connected to the docking station when the drug delivery device has an attached dispense interface.

For example, FIG. 36*a* depicts a drug delivery system 950 that includes electro-mechanical drug delivery device 952 and docking station 954. In this docking station arrangement, the docking station comprises a horizontal docking station. The drug delivery device 952 includes a main body 956 having a proximal end 958 and a distal end. A digital display 960 along with a plurality of human interface elements is provided near the proximal end 958 of the device.

As can be seen from FIG. 36a, the distal end of the device may be covered by a separable housing 962. However, as with other drug delivery devices described herein, the distal end of the drug delivery device 952 is configured to attach to a dispense interface. Drug delivery device 952 further comprises a conduction element 964 (shown in FIG. 36b). For example, FIG. 36b illustrates a perspective view of an underside 966 of the drug delivery device 952. As illustrated, the conduction element 964 is disposed on the backside 966 of the drug delivery device 952. However, it should be understood that this conduction element may be disposed elsewhere on the drug delivery device 952. This conduction element is sized and shaped to properly connect to an electrical connector 968 of the docking station 954.

The docking station 954 illustrated in FIG. 36a includes an electrical connector 968 and a conduction element 970. The electrical connector 968 is configured for connecting to the conduction element 964 provided along the underside of the drug delivery device 952. Further, the conduction element 970 is configured for connecting to an external electrical connector 972, which may be a USB connector. USB connector 972 may in turn be connected to an external device such as a computer, charger, or a power source. Therefore, when the drug delivery device 952 is docked on docking station 954, the external device would be communicatively linked to the drug delivery device 952.

The docking station 954 may be configured so that when the drug delivery device is attached to a dispense interface, the drug delivery device is prevented from connecting to the docking station. Therefore, a user could not use the device to administer a dose when the drug delivery device 952 is connected to an external device. The docking station 954 and drug delivery device 952 may be configured so that when the drug delivery device 952 is attached to a dispense interface, the drug delivery device 952 is prevented from connecting to the docking station 954 in a variety of ways. One example is depicted in FIG. 36a. In this example, docking station 954 includes a recess 974 that is configured to receive a portion of drug delivery device 952 when the device is inserted. If a dispense interface were connected to the drug delivery device 952, the distal end 976 of the recess would encounter the dispense interface (e.g., a needle) before the drug delivery device is properly docked. Therefore, the user would be unable to properly connect the drug delivery device 952 to the docking station 954.

The conduction elements and electrical connectors of this example can take various forms. In one example, conduction element 966 is different than conduction element 970. Similarly, connector 968 is different than connector 972. As such, connector 972 will not be able to fit in or connect to conduction element 966 provided on the underside 966 of the device 952. In one exemplary arrangement, the conduction elements and connector are different types. In another exemplary arrangement, the conduction elements and connectors may comprise different shapes and/or sizes. In another example, the docking station connector and the drug delivery device conduction element may both be contactless means and such contactless systems may provide a heighted degree of electrical isolation and hence user safety. The contactless means may, for example, be conduction elements and connectors that are based on inductive charging principles.

As can be seen from FIG. 36a, when the drug delivery device is inserted into the docking station 954, the drug delivery device 950 will be seated within the recess 974 in a horizontal position. One potential disadvantage of having the device seated in this horizontal position is that it might be difficult for a user or patient care giver to view the digital display 960 provided on the top surface of the device. Alternatively, a docking station could be used that would make it easier to view and perhaps access the digital interface 960 provided on the drug delivery device.

Figure 37:
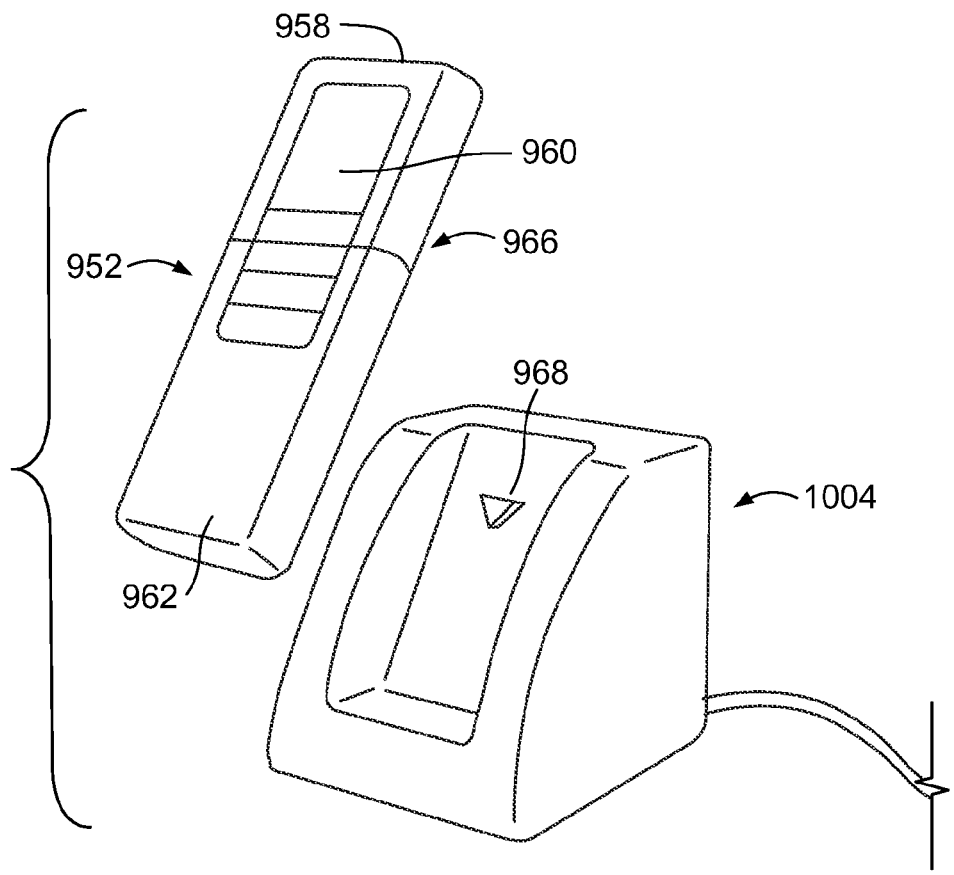
FIG. 37 illustrates a perspective view of yet another exemplary drug delivery system.

For example, FIG. 37 illustrates an alternative arrangement for a docking station 1004 that may be used with the drug delivery device 952 described with respect to FIGS. 36a and 36b. As illustrated, the docking station 1004 may take the form of a cradle where, once placed within the cradle, the drug delivery device will be seated in an upright position. One advantage of such an arrangement is that if the device is seated upright, it might be easier for a user or patient care giver to view the digital display 960.

The disclosed drug delivery devices and systems result in numerous advantages. For example, an electro-mechanical drug delivery device in accordance with this disclosure may prevent a user from administering a dose of a drug when the electro-mechanical drug delivery device is connected to an external device, such as an external power source. Beneficially, this may limit or prevent the risk of electrocution.

The disclosed electro-mechanical dose setting mechanism may be of particular benefit where a targeted therapeutic response can be optimized for a specific target patient group. This may be achieved by a microprocessor based drug delivery device that is programmed to control, define, and/or optimize at least one therapeutic dose profile. A plurality of potential dose profiles may be stored in a memory device operatively coupled to the microprocessor. For example, such stored therapeutic dose profiles may include, but are not limited to, a linear dose profile; a non-linear dose profile; a fixed ratio fixed dose profile; a fixed dose variable dose profile; a delayed fixed dose variable dose profile; or a multi-level, fixed dose variable dose profile as discussed and described in greater detail below. Alternatively, only one dose profile would be stored in a memory device operatively coupled to the microprocessor. In one dual medicament drug delivery device arrangement, the dose of the second medicament may be determined by way of a first therapeutic profile such as those identified above. In one drug delivery device comprising three medicaments, the dose of the second medicament may be determined by way of a first therapeutic profile while the dose of the third medicament may be determined by either the same first therapeutic profile or a second different therapeutic profile. As those of ordinary skill in the art will recognize, alternative therapeutic profile arrangements may also be used.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A drug delivery device comprising:
   a main body having a distal end and a proximal end, wherein the distal end is configured to attach to a dispense interface;
   a separable housing configured to couple to and to decouple from the main body, wherein the separable housing includes an electrical connector and a first conduction element in electrical connection with the electrical connector of the separable housing;
   a second conduction element provided by the main body, wherein the second conduction element is configured for establishing an electrical connection between the second conduction element and the electrical connector of the separable housing;

wherein the device is configured such that when the separable housing is coupled to the main body the administration of a drug by the drug delivery device is prevented, the separable housing covering at least a portion of the distal end of the main body, and establishment of the electrical connection between the second conduction element and an external electrical connector is allowed, and when the separable housing is decoupled from the main body the administration of a drug by the drug delivery device is enabled and the establishment of the electrical connection between the second conduction element and the external electrical connector is prevented.

2. The drug delivery device of claim 1, wherein the separable housing prevents the administration of the drug by the drug delivery device by preventing the main body from attaching to a dispense interface.

3. The drug delivery device of claim 1, wherein when the establishment of the electrical connection is allowed the electrical connector is enabled to be plugged in the second conduction element of the main body.

4. The drug delivery device of claim 1, wherein the conduction element of the main body or the conduction element of the separable housing comprises at least one of a Universal Serial Bus (USB) port, a Firewire port, a RS232 port or a proprietary port and wherein the electrical connector comprises at least a corresponding one of a USB plug, a Firewire plug, a RS232 plug or a proprietary plug.

5. The drug delivery device of claim 1, wherein the second conduction element of the main body or the conduction element of the separable housing is configured for establishing the electrical connection with the electrical connector for at least one of a transfer of power or a transfer of data.

6. The drug delivery device of claim 1, wherein the first conduction element of the separable housing and the electrical connector of the separable housing form integral parts of a connector member disposed in the separable housing, wherein the connector member is configured for establishing a first electrical connection with a corresponding electrical connector and a second electrical connection with the conduction element of the main body.

7. A drug delivery system comprising a drug delivery device according to claim 1 and a docking station configured such that the device can be seated in the docking station.

8. The drug delivery system of claim 7 wherein when the drug delivery device is seated within the docking station, the drug delivery device has an upright position.

9. The drug delivery device of any of claim 1, wherein the drug delivery device further comprises an electronic control unit, and wherein the first conduction element of the separable housing is communicatively linked to the electronic control unit when the separable housing is attached to the main body.

10. The drug delivery device of claim 9, wherein the first conduction element of the separable housing is not in communication with the electronic control unit of the drug delivery device when the separable housing is not connected to the main body.

11. The drug delivery device of claim 9, further comprising:

a blade connector disposed in the separable housing and configured to provide the electrical connection to the second conduction element of the main body, wherein the blade connector is in communication with the first conduction element of the separable housing, and wherein the blade connector communicates with the electronic control unit of the drug delivery device when the separable housing is attached to the main body.

12. The drug delivery device of claim 11, wherein the first conduction element of the separable housing is disposed on a distal end of the separable housing, and wherein the blade connector is disposed on a proximal end of the separable housing.

13. A drug delivery device comprising:

a main body having a distal end and a proximal end, wherein the distal end is configured to attach to a dispense interface;

a separable housing configured to couple to and to decouple from the main body;

a conduction element provided by the main body, wherein the device is configured for establishing an electrical connection between the conduction element and an external electrical connector;

a covering member provided by the main body, wherein the covering member covers the conduction element when the separable housing is not coupled to the main body;

wherein the device is configured such that when the separable housing is coupled to the main body the administration of a drug by the drug delivery device is prevented, the separable housing covering at least a portion of the distal end of the main body, and establishment of the electrical connection between the conduction element and an external electrical connector is allowed, the separable housing interacting with the covering member such that the conduction element gets uncovered, thereby enabling access of an external electrical connector to the conduction element and when the separable housing is decoupled from the main body the administration of a drug by the drug delivery device is enabled and the establishment of the electrical connection between the conduction element and an external electrical connector is prevented.

14. The drug delivery device of claim 13, wherein the covering member comprises a sliding door, wherein the sliding door does not cover the second conduction element in an open position and wherein the sliding door covers at least in part the second conduction element in a closed position.

15. The drug delivery device of claim 13, wherein the covering body comprises a pivoting member, wherein the pivoting member does not cover the second conduction element in an open position and wherein the pivoting member covers at least in part the second conduction element in a closed position.

* * * * *